United States Patent
Shah et al.

(10) Patent No.: US 10,633,636 B2
(45) Date of Patent: Apr. 28, 2020

(54) ONCOLYTIC VIRUS THERAPY FOR RESISTANT TUMORS

(71) Applicant: The General Hospital Corporation, Boston, MA (US)

(72) Inventors: Khalid Shah, Andover, MA (US); Kaoru Tamura, Tokyo (JP); Hiroaki Wakimoto, Newton, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/832,109

(22) Filed: Dec. 5, 2017

(65) Prior Publication Data

US 2018/0148694 A1  May 31, 2018

Related U.S. Application Data

(63) Continuation of application No. 14/416,754, filed as application No. PCT/US2013/031949 on Mar. 15, 2013, now Pat. No. 9,862,932.

(60) Provisional application No. 61/675,013, filed on Jul. 24, 2012.

(51) Int. Cl.
| | |
|---|---|
| *C12N 7/00* | (2006.01) |
| *C07K 14/525* | (2006.01) |
| *A61K 35/763* | (2015.01) |
| *A61K 38/19* | (2006.01) |

(52) U.S. Cl.
CPC .............. *C12N 7/00* (2013.01); *A61K 35/763* (2013.01); *A61K 38/19* (2013.01); *C07K 14/525* (2013.01); *C12N 2710/16632* (2013.01); *C12N 2710/16642* (2013.01); *C12N 2710/16671* (2013.01)

(58) Field of Classification Search
None
See application file for complete search history.

(56) References Cited

U.S. PATENT DOCUMENTS

| | | | |
|---|---|---|---|
| 5,037,743 A | 8/1991 | Welch et al. | |
| 5,143,830 A | 9/1992 | Holland et al. | |
| 5,288,641 A | 2/1994 | Roizman | |
| 5,501,979 A | 3/1996 | Geller | |
| 5,587,459 A | 12/1996 | Uckun | |
| 6,284,236 B1 | 9/2001 | Wiley et al. | |
| 6,444,640 B1 | 9/2002 | Nagane et al. | |
| 6,632,979 B2 | 10/2003 | Erickson et al. | |
| 6,743,625 B2 | 6/2004 | Ni et al. | |
| 6,998,116 B1 | 2/2006 | Ashkenazi | |
| 7,045,127 B2 | 5/2006 | Raisch et al. | |
| 7,052,834 B1 | 5/2006 | Kidd et al. | |
| 7,063,835 B2 | 6/2006 | Coffin | |
| 7,399,835 B2 | 7/2008 | Young et al. | |
| 7,538,195 B2 | 5/2009 | Singh et al. | |
| 7,598,350 B2 | 10/2009 | Liu et al. | |
| 7,754,859 B2 | 7/2010 | Liang et al. | |
| 7,790,164 B2 | 9/2010 | Cao | |
| 7,790,451 B2 | 9/2010 | Yazaki et al. | |
| 8,029,783 B2 | 10/2011 | Adams et al. | |
| 8,034,904 B2 | 10/2011 | Singh et al. | |
| 8,216,819 B2 | 7/2012 | Hermiston et al. | |
| 8,222,036 B2 | 7/2012 | Thompson et al. | |
| 8,236,941 B2 | 8/2012 | Yao | |
| 8,263,081 B2 | 9/2012 | Fu | |
| 8,313,896 B2 | 11/2012 | Martuza et al. | |
| 8,461,304 B2 | 6/2013 | Gunnarsson et al. | |
| 8,545,839 B2 | 10/2013 | Goetsch et al. | |
| 8,580,263 B2 | 11/2013 | Adams et al. | |
| 8,933,202 B2 | 1/2015 | Hettmann et al. | |
| 8,975,382 B2 | 3/2015 | Revets et al. | |
| 9,072,798 B2 | 7/2015 | Ritter et al. | |
| 9,862,932 B2 * | 1/2018 | Shah | A61K 35/763 |
| 2002/0128438 A1 | 9/2002 | Seol et al. | |
| 2004/0120928 A1 | 6/2004 | Frenkel | |
| 2005/0084960 A1 | 4/2005 | Goldstein | |
| 2005/0214266 A1 | 9/2005 | Morris et al. | |
| 2005/0276812 A1 | 12/2005 | Ebens et al. | |
| 2009/0155247 A1 | 6/2009 | Ashkenazi | |
| 2009/0175826 A1 | 7/2009 | Subbiah | |

(Continued)

FOREIGN PATENT DOCUMENTS

| | | |
|---|---|---|
| EP | 1909849 B1 | 8/2013 |
| WO | 2002/022175 A2 | 3/2002 |

(Continued)

OTHER PUBLICATIONS

Merino et al. TRAIL in cancer therapy: present and future challenges. Expert Opin Ther Targets. Oct. 2007; 11(10): 1299-1314. (Year: 2007).*

Ashkenazi et al., "Ligand-Based Targeting of Apoptosis in Cancer: The Potential of Recombinant Human Apoptosis Ligand 2/Tumor Necrosis Factor-Related Apoptosis-Inducing Ligand (rhApo2L/TRAIL)", J Clin Oncol 26(21): 3621-30.

(Continued)

*Primary Examiner* — Michelle S Horning

(74) *Attorney, Agent, or Firm* — Nixon Peabody LLP; David S. Resnick; Mark J. FitzGerald

(57) ABSTRACT

Disclosed herein is a recombinant oncolytic virus comprising a nucleic acid sequence encoding tumor necrosis factor-related apoptosis-inducing ligand (TRAIL). One such oncolytic virus is oHSV. One form of TRAIL contained within the oncolytic virus is a secreted form of TRAIL. Examples of various forms of oHSV and secreted TRAIL are disclosed therein. Also disclosed are host cells and therapeutic formulations comprising the recombinant oncolytic virus. Also disclosed are methods of treating cancer in a subject by administering a therapeutic formulation comprising the recombinant oncolytic virus to the subject.

9 Claims, 17 Drawing Sheets

Specification includes a Sequence Listing.

(56) References Cited

U.S. PATENT DOCUMENTS

| | | |
|---|---|---|
| 2009/0285860 A1 | 11/2009 | Martuza |
| 2009/0325867 A1 | 12/2009 | Cohen et al. |
| 2010/0240097 A1 | 9/2010 | Young et al. |
| 2010/0272686 A1 | 10/2010 | Kaur et al. |
| 2010/0305002 A1 | 12/2010 | Chenchik et al. |
| 2010/0305696 A1 | 12/2010 | Mao |
| 2010/0311948 A1 | 12/2010 | Hua et al. |
| 2010/0323399 A1 | 12/2010 | Wiley et al. |
| 2011/0014656 A1 | 1/2011 | Levin et al. |
| 2011/0177032 A1 | 7/2011 | Martuza et al. |
| 2013/0189189 A1 | 7/2013 | Chang |

FOREIGN PATENT DOCUMENTS

| | | |
|---|---|---|
| WO | 2004/087930 A2 | 10/2004 |
| WO | 2005/000220 A2 | 1/2005 |
| WO | 2009/028870 A2 | 3/2009 |
| WO | 2009/029601 A2 | 3/2009 |
| WO | 2009/148488 A2 | 12/2009 |
| WO | 2012/072815 A1 | 6/2012 |
| WO | 2012/106281 A2 | 8/2012 |
| WO | 2014/018113 A1 | 1/2014 |
| WO | 2014/035474 A1 | 3/2014 |

OTHER PUBLICATIONS

Aghi et al., "Oncolytic viral therapies—the clinical experience", Oncogene 24:7802-7816 (2005).

Allan et al., "Inhibition of caspase-9 through phosphorylation at Thr 125 by ERK MAPK", Nat Cell Biol 5(7):647-654 (2003).

An et al., "Drug Interactions between the Proteasome Inhibitor Bortezomib and Cytotoxic Chemotherapy, Tumor Necrosis Factor (TNF) beta, and TNF-Related Apoptosis-Inducing Ligand in Prostate Cancer", Clin. Ca. Res.9:4537-4545 (2003).

Badran et al., "Target cell-restricted apoptosis inducation by 528scFv-TRAIL fusion protein specific for human EGFR and expressed in *Escherichia coli*", International Journal of Oncology, 36(5):1229-1234 (2010).

Bagci-Onder et al., "A dual PI3K/mTOR Inhibitor, PI-103, Cooperates with Stem Cell-Delivered TRAIL in Experimental Glioma Models", Cancer Research, 71(1):154-63 (2011).

Barash et al., "Human secretory signal peptide description by hidden Markov model and generation of a strong artificial signal peptide for secreted protein expression", Biochem Biophys Res Commun, 294(4):835-842 (2002).

Breitbach et al., "Intravenous delivery of a multi-mechanistic cancer-targeted oncolytic poxvirus in humans", Nature, 477:99-102 (2011).

Bremer et al., "Exceptionally Potent Anti-Tumor Bystander Activity of an scFv:sTRAIL Fusion Protein with Specificity for EGP2 Toward Target Antigen-Negative Tumor Cells", Neoplasia, 6(5):636-645 (2004).

Bremer et al., "Potent Systemic Anticancer Activity of Adenovirally Expressed EGFR-Selective TRAIL Fusion Protein", Molecular Therapy 16(12):1919-1926 (2008).

Bremer et al., "Simultaneous Inhibition of Epidermal Growth Factor Receptor (EGFR) Signaling and Enhanced Activation of Tumor Necrosis Factor-related Apoptosis-inducing Ligand (TRAIL) Receptor-mediated Apoptosis Induction by an scFv:sTRAIL Fusion Protein with Specificity for Human EGFR", J. Biol. Chem., 280(11):10025-10033 (2005).

Bremer et al., "Target Cell-Restricted Apoptosis Induction of Acute Leukemic T Cells by a Recombinant Tumor Necrosis Factor-Related Apoptosis-Inducing Ligand Fusion Protein with Specificity for Human CD7", Cancer Res., 65(8):3380-3388 (2005).

Bremer et al., "Targeted delivery of a designed sTRAIL mutant results in superior apoptotic activity towards EGFR-positive tumor cells", J Mol Med., 86(8):909-924 (2008).

Choo et al., "SPdb—a signal peptide database", BMC Bioinformatics, 6:249 (2005).

Compte et al., "Tumor Immunotherapy Using Gene-Modified Human Mesenchymal Stem Cells Loaded into Synthetic Extracellular Matrix Scaffolds", Stem Cells, 27(3):753-760 (2009).

Corsten et al., "MicroRNA-21 Knockdown Disrupts Glioma Growth in vivo and Displays Synergistic Cytotoxicity with Neural Precursor Cell-Delivered S-TRAIL in Human Gliomas", Cancer Res., 67(19):8994-9000 (2007).

Corsten et al., "Therapeutic stem-cells for cancer treatment: hopes and hurdles in tactical warfare", Lancet Oncol., 9(4):376-384 (2008).

Ehtesham et al., "Induction of Glioblastoma Apoptosis Using Neural Stem Cell-mediated Delivery of Tumor Necrosis Factor-related Apoptosis-inducing Ligand", Cancer Res., 62(24):7170-7174 (2002).

Erhardt et al., "B-Raf Inhibits Programmed Cell Death Downstream of Cytochrome c Release from Mitochondria by Activating the MEK/Erk Pathway", Mol Cell Biol., 19(8):5308-5315 (1999).

Foley et al., "Mutations in the Elongation Factor 2 Gene Which Confer Resistance to Diphtheria Toxin and Pseudomonas Exotoxin A", The Journal of Biological Chemistry 270(39):23218-23225 (1995).

Fukuhara et al., "Triple Gene-Deleted Oncolytic Herpes Simplex Virus Vector Double-Armed with Interleukin 18 and Soluble B7-1 Constructed by Bacterial Artificial Chromosome-Mediated System", Cancer Res., 65(23):10663-10668 (2005).

Gibbons et al., "Adult human brain cell culture for neuroscience research", Int J Biochem Cell Biol 42(6) 844-856 (2010).

Han et al., "Development of a second-generation oncolytic Herpes simplex virus expressing TNF alpha for cancer therapy", J Gene Med., 9(2):99-106 (2007).

Hingtgen et al., "A Novel Molecule Integrating Therapeutic and Diagnostic Activities Reveals Multiple Aspects of Stem Cell-Based Therapy", Stem Cells, 28(4):832-841 (2010).

Hingtgen et al., "Targeting multiple pathways in gliomas with stem cell and viral delivered S-TRAIL and Temozolomide", Mol Cancer Ther., 7(11):3575-3585 (2008).

Hoffman et al., "Comparison of herpes simplex virus- and conditionally replicative adenovirus-based vectors for glioblastoma treatment", Cancer Gene Therapy, 14(7):627-639 (2007).

Holmstrom et al., "MAPK/ERK signaling in activated T cells inhibits CD95/Fas-mediated apoptosis downstream of DISC assembly", EMBO Journal, 19(20):5418-5428 (2000).

Jacobson et al., "Programmed Cell Death in Animal Development", Cell, 88: 347-354 (1997).

Jiang et al., "A new approach with less damage: intranasal delivery of tetracycline-inducible replication-defective herpes simplex virus type-1 vector to brain", Neuroscience 201;96-104 (2012).

Johnstone et al., "The TRAIL apoptotic pathway in cancer onset, progression and therapy", Nat Rev Cancer, 8(10): 782-798 (2008).

Kanai et al., "A Novel Oncolytic Herpes 1-15 Simplex Virus that Synergizes with Phosphoinositide 3-kinase/Akt Pathway Inhibitors to Target Glioblastoma Stem Cell", Clinical Cancer Research, 17(11):3686-3696 (2011).

Kauer et al. Encapsulated therapeutic stem cells implanted in the tumor resection cavity induce cell death in gliomas, Nat Neurosci. Dec. 25, 2011; 15(2): 197-204.

Kelley et al., "Preclinical Studies to Predict the Disposition of Apo2L/Tumor Necrosis Factor-Related Apoptosis-Inducing Ligand in Humans: Characterization of in Vivo Efficacy, Pharmacokinetics, and Safety", J Pharmacol Exp Ther., 299(1):31-38 (2001).

Kirn et al., "Replication-selective virotherapy for cancer: Biological principles, risk management and future directions", Nat Med 7(7):781-787 (2001).

Kirshner et al., "Identification of TRAIL as an Interferon Regulatory Factor 3 Transcriptional Target", Journal of Virology, 79(14):9320-9324 (2005).

Kock et al., "Tumor Therapy Mediated by Lentiviral Expression of shBcl-2 and S-TRAIL", Neoplasia, 9(5):435-442 (2007).

Kuijlen et al., "Review: on TRAIL for malignant glioma therapy?", Neuropathology and Applied Neurobiology, 36(3):168-182 (2010).

Kuroda et al., "Flip-Flop HSV-BAC: bacterial artificial chromosome based system for rapid generation of recombinant herpes simplex virus vectors using two independent site-specific recombinases", BMC Biotechnology, 6:40 (2006).

(56) References Cited

OTHER PUBLICATIONS

Kurozumi et al., "Effect of Tumor Microenvironment Modulation on the Efficacy of Oncolytic Virus Therapy", J Natl Cancer Inst., 99(23):1768-1781 (2007).
Leblanc et al., "Apo2L/TRAIL and its death and decoy receptors", Cell Death and Differentiation, 10(1):66-75 (2003).
Leopardi et al., "The herpes simplex virus 1 protein kinase US3 is required for protection from apoptosis induced by the virus" PNAS, 94(15):7891-7896 (1997).
Leopardi et al., "The herpes simplex virus major regulatory protein ICP4 blocks apoptosis induced by the virus or by hyperthermia", PNAS, 93(18):9583-9587 (1996).
Liu et al., "Clinical trial results with oncolytic virotherapy: a century of promise, a decade of progress", Nat Clin Pract Oncol., 4(2):101-117 (2007).
Liu et al., "Expression of an Anti-CD3 Single-Chain Immunotoxin with a Truncated Diphtheria Toxin in a Mutant CHO Cell Line", Protein Expression and Purification 19(2):304-311 (2000).
Lubkowski et al., "The structural basis of phage display elucidated by the crystal structure of the N-terminal domains of g3p", Nature Struct. Biol., 5(2):140-147 (1998).
Markert et al., "Conditionally replicating herpes simplex virus mutant G207 for the treatment of malingnt glioma: results of a phase I trial", Gene Therapy, 7(10):867-874 (2000).
Markert et al., "High diagnostic value of morphologic examination and molecular analysis of bone marrow biopsies in a case of BCR-ABL+ CML with clusters of blasts", Int J Hematol., 89(3):294-297 (2009).
Markert et al., "Phase Ib Trial of Mutant Herpes Simplex Virus G207 Inoculated Pre-and Post-tumor Resection for Recurrent GBM", Molecular Therapy, 17(1):199-207 (2009).
Martinelli et al., Clinical and Experimental Immunology 158(1):1-9 (2009). "Anti-epidermal growth factor receptor monoclonal antibodies in cancer therapy.".
Mineta et al., "Attenuated multi-mutated herpes simplex virus-1 for the treatment of malignant gliomas", Nature Medicine, 1(9):938-943 (1995).
Doshi et al., "In vitro nanobody discovery for integral membrane protein targets." Scientific Reports 4(6760):1-8 (2014).
Miyatake et al., "Transcriptional Targeting of Herpes Simplex Virus for Cell-Specific Replication", J Virol., 1(7):5124-5132 (1997).
Moehring et al., "Selection and Characterization of Cells Resistant to Diphtheria Toxin and Pseudonomas Exotoxin A: Presumptive Translation Mutants", Cell 11(12):447-454 (1977).
Oliveira et al., "Downregulation of EGFR by a novel multivalent nanobody-liposome platform", J. Control Release, 145(2):165-75 (2010).
Pan et al., "Synergistic induction of tumor cell death by combining cisplatin with an oncolytic adenovirus carrying TRAIL", Mol Cell Biochem., 304:315-323 (2007).
Parato et al., "Recent Progress in the Battle Between Oncolytic Viruses and Tumors", Nat Rev Cancer, 5:965-976 (2005).
Rieger et al., "Mechanisms of Resistance of Human Glioma Cells to Apo2 ligand/TNF-Related Apoptosis-Inducing Ligand", Cell Physiol Biochem., 20:23-34 (2007).
Roovers et al., "Efficient inhibition of EGFR signaling and of tumour growth by antagonistic anti-EFGR Nanobodies", Immunotherapy 56(3): 303-317, (2007).
Rozanov et al., "Engineering a leucine zipper-TRAIL homotrimer with improved cytotoxicity in tumor cells", Mol Cancer Ther., 8(6):1515-1525 (2009).
Saeki et al.,"Herpes Simplex Virus Type 1 DNA Amplified as Bacterial Artificial Chromosome in *Escherichia coli*: Rescue of Replication-Competent Virus Progeny and Packaging of Amplicon Vectors", Human Gene Therapy, 9:2787-2794 (1998).
Sasportas et al., "Assessment of therapeutic efficacy and fate of engineered human mesenchymal stem cells for cancer therapy", PNAS, 106(12):4822-48277 (2009).
Shah et al., "Bimodal Viral Vectors and In Vivo Imaging Reveal the Fate of Human Neural Stem Cells in Experimental Glioma Model", The Journal of Neuroscience, 28(17):4406-4413 (2008).
Shah et al., "In vivo Imaging of S-TRAIL-Medicated Tumor Regression and Apoptsis", Molecular Therapy, 11(6):926-931 (2005).
Shah et al., "Inducible release of TRAIL fusion proteins from a proapoptotic form for tumor therapy." Cancer Research 64(9):3236-3242 (2004).
Shah et al., "Real-time imaging of TRAIL-induced apoptosis of glioma tumors in vivo", Oncogene 22:6865-6872 (2003).
Shah et al., "Glioma Therapy and Real-Time Imaging of Neural Precursor Cell Migration and Tumor Regression", Ann Neurol., 57(1):34-41 (2005).
Shen et al., "Construction and characterization of two versions of bifunctional EGFP-sTRAIL fusion proteins", Appl Microbiol Biotechnol., 76:141-149 (2007).
Smith et al., "Human Bone Marrow-Derived Mesenchymal Stem Cells for Intranasal Delivery of Oncolytic Herpes Simplex Virus Type I to Human Gliomas", Molecular Therapy 21(Suppl 1) S246-S247 (2013).
Smith et al., "The TNF Receptor Superfamily of Cellular and Viral Proteins: Activation, Constimulation, and Death", Cell, 76:959-062 (1994).
Sprenger et al., "LOCATE: a mammalian protein subcellular localization database", Nucleic Acids Research, 36:D230-D233 (2008).
Stern et al., "Improving mammalian cell factories: The selection of signal peptide has a major impact on recombinant protein synthesis and secretion in mammalian cells", Cell and Molecular Biology, 2:1-17 (2007).
Stieglmaier et al., "Selective induction of apoptosis in leukemic B-lymphoid cells by a CD19-specific TRAI fusion protein", Cancer Immunol Immunother, 57:233-246 (2008).
Tamura et al., "Multimechanistic Tumor Targeted Oncolytic Virus Overcomes Resistance in Brain Tumor", Mol. Therapy, 21(1):68-77 (2013).
Tashker et al., "Post-Cytochrome C Protection from Apoptosis Conferred by a MAPK Pathway in Xenopus Egg Extracts", Mol Biol Cell, 13:393-401 (2002).
Theuer et al., "A Recombinant Form of Pseudomonas Exotoxin Directed at the Epidermal Growth Factor Receptor That Is Cytotoxic without Requiring Proteolytic Processing", The Journal of Biological Chemistry 267(24):16872-16877 (1992).
Todo et al., "Armed oncolytic herpes simplex viruses for brain tumor therapy", Cell Adhesion Migration, 2(3):208-213 (2008).
Todo et al., "Oncolytic herpes simplex virus vector with enhanced MHC class I presentation and tumor cell killing" PNAS, 98(11):6396-6401 (2001).
Varghese et al., "Oncolytic herpes simplex virus vectors for cancer virotherapy", Cancer Gene Therapy, 9:967-978 (2002).
Voss et al., "Delivery of Oncolytic Herpes Simplex Virus to Infiltrative Brain Tumor Sites Via Neuronal Stem Cells", Molecular Therapy 13(Suppl 1) S411 (2006).
Wakimoto et al., "Human Glioblastoma-Derived Cancer Stem Cells: Establishment of Invasive Glioma Models and Treatment with Oncolytic Herpes Simplex Virus Vectors", Cancer Research, 69(8):3472-3481 (2009).
Wang et al., "Development of a nonintegrating Rev-dependent lentiviral vector carrying diphtheria toxin A chain and human TRAF6 to target HIV reservoirs", Gene Therapy 17(9):1063-1076 (2010).
Wang et al., Cancer Biol Ther. 6(6):980-7 (2007). "In vitro efficacy of immuno-chemotherapy with anti-EGFR human Fab-Taxol conjugate on A431 epidermoid carcinoma cells."
Wen et al., "Malignant Gliomas in Adults", N Engl J Med., 359(5):492-507 (2008).
Wiezorek et al., "Death Receptor Agonists as a Targeted Therapy for Cancer", Clin Cancer Res., 16(6):1701-1708 (2010).
Wohlfahrt et al., "A Capsid-Modified, Conditionally Replicating Oncolytic Adenovirus Vector Expressing TRAIL Leads to Enhanced Cancer Cell Killing in Human Glioblastoma Models", Cancer Research, 67(8):8783-8790 (2007).
Xia et al., "Opposing effects of ERK and JNK-p38 MAP kinases on apoptosis", Science, 270.5240:1326-1331 (1995).

(56) References Cited

OTHER PUBLICATIONS

Yamamoto et al., "Imaging immediate-early and strict-late promoter activity during oncolytic herpes simplex virus type 1 infection and replication in tumors", Gene Therapy, 13:731-1736 (2006).
Yip et al., "Stem-cell based therapies for brain tumors", Current Opinion in Molecular Therapeutics, 10(4):334-342 (2008).
Ahmed et al., "Neural Stem Cell-based Cell Carriers Enhance Therapeutic Efficacy of an Oncolytic Adenovirus in an Orthotopic Mouse Model of Human Glioblastoma", Mol Ther, 19(9): 1714-1726 (2011).
Bexell et al., "Stem cell-based therapy for malignant glioma." Cancer Treatment Reviews 39(4): 358-365 (2013).
Carney et al., "Migration and fate of therapeutic stem cells in different brain disease models," Neuroscience 197: 37-47 (2011).
Garcia-Castro et al. "Treatment of metastatic neuroblastoma with systemic oncolytic virotherapy delivered by autologous mesenchymal stem cells: an exploratory study." Cancer Gene Therapy 17(7): 476-483 (2010).
Jacobs et al. "Immunological characteristics of human mesenchymal stem cells and multipotent adult progenitor cells." Immunology and Cell Biology 91(1): 32-39 (2013).
Lorusso et al. "Trastuzumab emtansine: a unique antibody-drug conjugate in development for human epidermal growth factor receptor 2—positive cancer." Clinical Cancer Research 17(20):6347-6447 (2011).
Mader et al. "Optimizing patient derived mesenchymal stem calls as virus carriers for a Phase I clinical trial in ovarian cancer." Journal of Translational Medicine 11(20): 1-14 (2013).
Martinez-Quintanilla et al., "Therapeutic efficacy and fate of bimodal engineered stem cells in malignant brain tumors." Stem Cells 31(8):1706-1714 (2013).
Naik et al. "A review on-glioblastoma multiform." Int. J. Pharm. Tech. Res 5(3): 873-878 (2013).
Nakamizo et al. "Human bone marrow—derived mesenchymal stem cells in the treatment of gliomas." Cancer research 65(8): 3307-3318 (2005).
Pasche et al., "Immunocytokines: a novel class of potent armed antibodies." Drug Discovery Today 17(11-12):583-590 (2012).
Pereboeva et al. "Approaches to Utilize Mesenchymal Progenitor Cells as Cellular Vehicles." Stem Cells 21(4):389-404 (2003).

* cited by examiner

FIG. 1B FIG. 1C

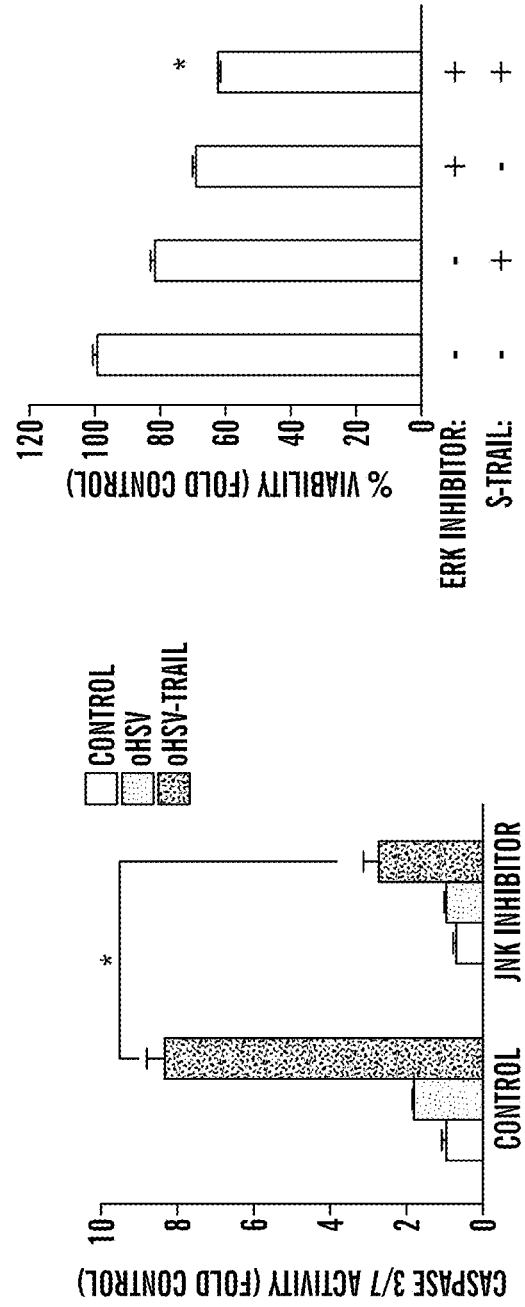
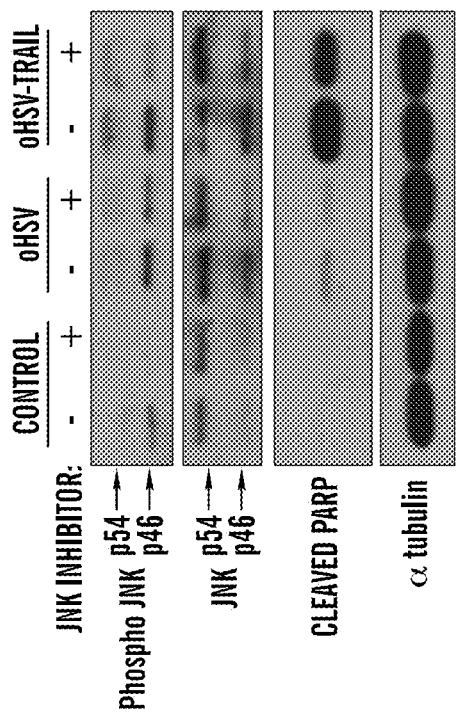
FIG. 4A
FIG. 4B
FIG. 4C
FIG. 4D

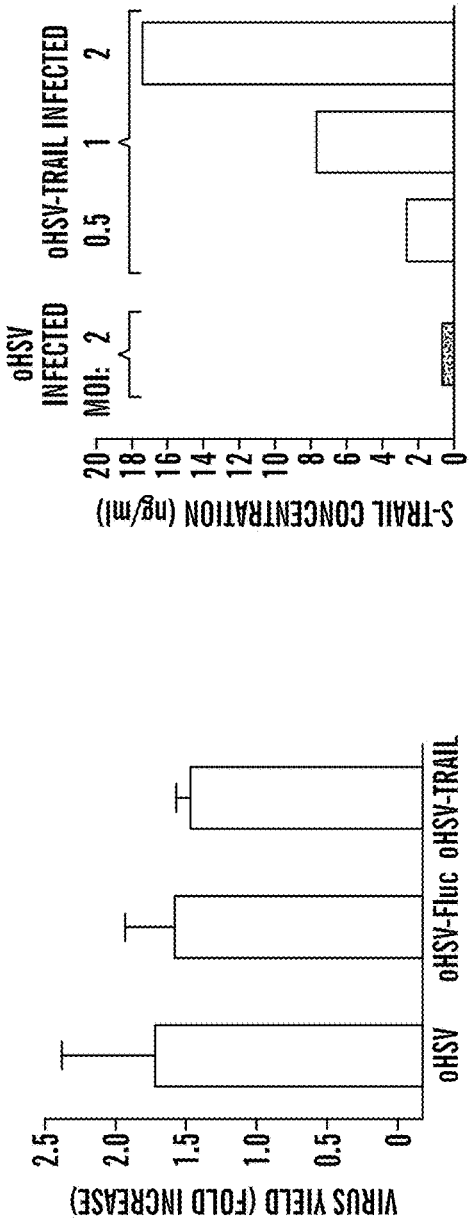
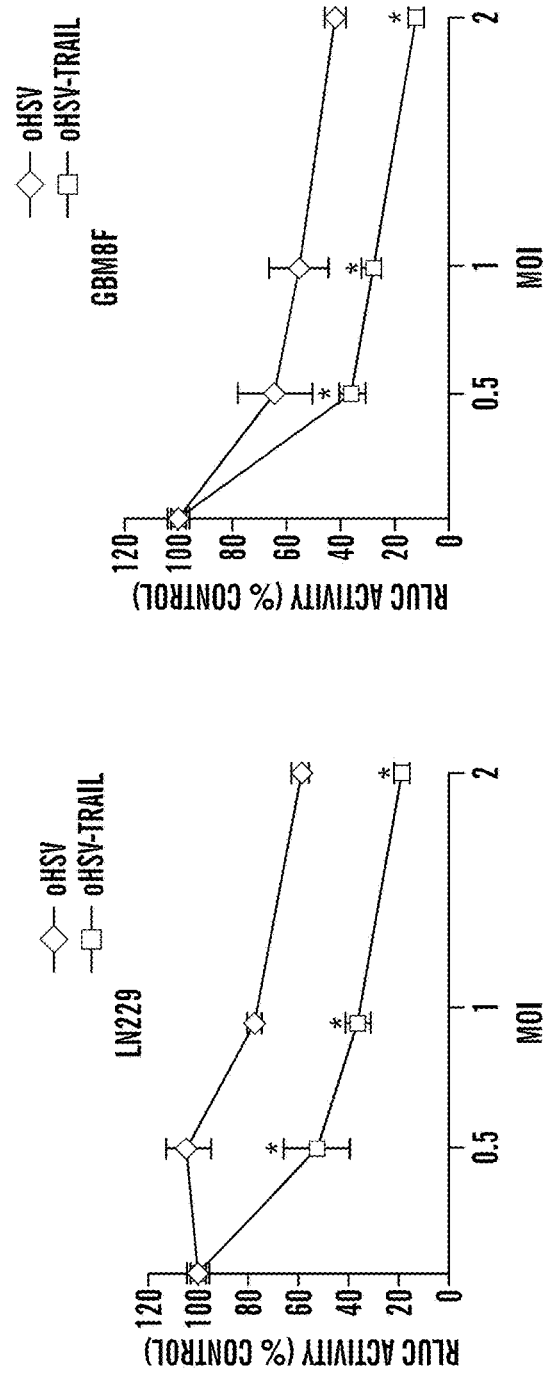
FIG. 10A
FIG. 10B
FIG. 10C
FIG. 10D

ONCOLYTIC VIRUS THERAPY FOR RESISTANT TUMORS

CROSS-REFERENCE TO RELATED APPLICATIONS

This application is a continuation application under 35 U.S.C § 120 of co-pending U.S. application Ser. No. 14/416,754, filed on Jan. 23, 2015, which is a 35 U.S.C. § 371 National Phase Entry Application of International Application No. PCT/US2013/031949 filed Mar. 15, 2013, which designates the U.S., and which claims benefit under 35 U.S.C. § 119(e) of U.S. Provisional Application No. 61/675,013, filed Jul. 24, 2012, the contents of each of which are incorporated herein by reference in their entirety.

GOVERNMENTAL SUPPORT

This invention was made with Government support under NS03677, CA138922-01, and NS076873 awarded by the National Institutes of Health. The Government has certain rights in the invention.

SEQUENCE LISTING

The instant application contains a Sequence Listing which has been submitted in ASCII format via EFS-Web and is hereby incorporated by reference in its entirety. Said ASCII copy, created on Dec. 3, 2017, is named 030258-073052-US_SL.txt and is 5,372 bytes in size.

FIELD OF THE INVENTION

The present invention relates to the field of cancer therapeutics.

BACKGROUND OF THE INVENTION

Glioblastoma multiforme (GBM) is a high-grade glioma and the most common primary malignant brain tumor.[1] GBMs are diffuse and infiltrating with no clear border between normal brain and tumor. Current treatment regimens that include temozolomide have significantly improved the median, 2- and 5-year survival compared to radiotherapy alone in patients with newly diagnosed GBM.[2,3] Nevertheless, GBM patients have a poor prognosis with a median survival of 14.6 months.[2] The inherent or acquired resistance of tumor cells to antitumor agents and the highly invasive nature of tumor cells are the major impediments to the currently employed anti-GBM therapies and pose an urgent need for novel therapeutics with substantial efficacy. Oncolytic herpes simplex virus (oHSV) and TRAIL (tumor necrosis factor-related apoptosis-inducing ligand) have recently shown promise in both preclinical and clinical trials.[4,5,6,7,8,9,10,11,12,13] Oncolytic viruses are genetically modified viruses that, upon infection, selectively replicate in and kill neoplastic cells while sparing normal cells.[4,8,14] Among them, oHSV type 1-derived virus is one of the most extensively studied and considered a promising agent for treating brain tumors as well as other types of cancer.[4,15] Recombinant oHSV vectors such as G207 and G47Δ have been previously investigated in both preclinical and clinical studies.[9,16,17,18] Unlike replication-incompetent vectors, replication-competent or conditional vectors can amplify to produce virus progeny that then infects surrounding tumor cells resulting in multiple waves of infection in situ, virus spread and extensive cell death. In a direct comparison between oncolytic adenovirus and oHSV in GBM cell lines, oHSV was shown to be more efficacious.[19] Mutations of specific HSV genes, namely γ34.5 and UL39, have been shown to confer selectivity to cancer cells, which has enabled translational studies to humans.[4,15] Although phase 1 and 1b clinical trials for oHSV proved its safety, the efficacy for human GBMs seems marginal as only a subset of patients showed decrease in tumor volume[9] which could in part be due to the insensitivity of a subset of GBM cells to HSV mediated oncolysis.

TRAIL has emerged as a promising antitumor agent due to its tumor-specific induction of apoptosis in a death receptor-dependent manner.[20] Both recombinant human TRAIL ligand and TRAIL receptor agonist monoclonal antibodies are currently being evaluated in clinical trials,[21] however, short half-life and off-target toxicity of systemically delivered TRAIL pose challenges in the clinic.[22] It has previously been established that a secreted form of TRAIL (S-TRAIL) exerts more potent apoptotic effects compared to TRAIL itself and when delivered by viruses or different stem cell types has significant antitumor effects as compared to systemically administered TRAIL in different mouse models of GBMs.[5,7,10,11,12,23] However, malignant GBMs show heterogeneity in their response to TRAIL; with ~50% showing sensitivity to TRAIL-mediated apoptosis and others showing varying resistance to TRAIL-mediated apoptosis.

SUMMARY OF THE INVENTION

Aspects of the invention relate to a recombinant oncolytic virus comprising a nucleic acid sequence encoding tumor necrosis factor-related apoptosis-inducing ligand (TRAIL) or a biologically active fragment thereof, in expressible form. In one embodiment, the oncolytic virus is an oncolytic herpes simplex virus (oHSV). In one embodiment, the oHSV is G207, G47Δ, HSV-R3616, 1716, R3616, or R4009. In one embodiment, the TRAIL is a secreted form of TRAIL (S-TRAIL). In one embodiment, the TRAIL is a TRAIL fusion protein. In one embodiment, the TRAIL is regulated by the HSV immediate early 4/5 promoter. In one embodiment, the oncolytic virus contains an additional exogenous nucleic acid in expressible form. In one embodiment, the virus contains no additional exogenous nucleic acids.

Another aspect of the invention relates to a nucleic acid comprising the genome of a recombinant oncolytic virus described herein. In one embodiment, the nucleic acid is a bacterial artificial chromosome (BAC), a P1-derived artificial chromosome (PAC), a yeast artificial chromosome (YAC) or a human artificial chromosome (HAC). Another aspect of the invention relates to a host cell comprising a recombinant oncolytic virus described herein or the nucleic acid comprising the genome of the recombinant oncolytic virus.

Another aspect of the invention relates to a pharmaceutical composition comprising the recombinant oncolytic virus described herein. Another aspect of the invention relates to a kit comprising the pharmaceutical composition described herein, and instructions for use.

Another aspect of the invention relates to a method of inhibiting tumor progression in a subject comprising contacting the tumor with an effective amount of a recombinant oncolytic virus described herein. In one embodiment, the tumor is a brain tumor. In one embodiment, the brain tumor is a glioma. In one embodiment the tumor is malignant. In one embodiment the tumor is selected from the group consisting of adenoma, angio-sarcoma, astrocytoma, epithelial carcinoma, germinoma, glioblastoma, glioma, hamartoma, hemangioendothelioma, hemangiosarcoma, hematoma, hepato-blastoma, leukemia, lymphoma, medulloblastoma, melanoma, neuroblastoma, osteosarcoma, retinoblastoma, rhabdomyosarcoma, sarcoma, and teratoma. The tumor can be chosen from acral lentiginous melanoma, actinic keratoses, adenocarcinoma, adenoid cycstic carcinoma, adenomas, adenosarcoma, adenosquamous carcinoma, astrocytic tumors, bartholin gland carcinoma, basal cell carcinoma, bronchial gland carcinomas, capillary, carcinoids, carcinoma, carcinosarcoma, cavernous, cholangiocarcinoma, chondosarcoma, choriod plexus papilloma/carcinoma, clear cell carcinoma, cystadenoma, endodermal sinus tumor, endometrial hyperplasia, endometrial stromal sarcoma, endometrioid adenocarcinoma, ependymal, epitheloid, Ewing's sarcoma, fibrolamellar, focal nodular hyperplasia, gastrinoma, germ cell tumors, glioblastoma, glucagonoma, hemangiblastomas, hemangioendothelioma, hemangiomas, hepatic adenoma, hepatic adenomatosis, epatocellular carcinoma, insulinoma, intaepithelial neoplasia, interepithelial squamous cell neoplasia, invasive squamous cell carcinoma, large cell carcinoma, leiomyosarcoma, lentigo maligna melanomas, malignant melanoma, malignant mesothelial tumors, medulloblastoma, medulloepithelioma, melanoma, meningeal, mesothelial, metastatic carcinoma, mucoepidermoid carcinoma, neuroblastoma, neuroepithelial adenocarcinoma nodular melanoma, oat cell carcinoma, oligodendroglial, osteosarcoma, pancreatic, papillary serous adeno-carcinoma, pineal cell, pituitary tumors, plasmacytoma, pseudo-sarcoma, pulmonary blastoma, renal cell carcinoma, retinoblastoma, rhabdomyosarcoma, sarcoma, serous carcinoma, small cell carcinoma, soft tissue carcinomas, somatostatin-secreting tumor, squamous carcinoma, squamous cell carcinoma, submesothelial, superficial spreading melanoma, undifferentiated carcinoma, uveal melanoma, verrucous carcinoma, vipoma, well differentiated carcinoma, and Wilm's tumor. In one embodiment contacting is by a method of administration to the subject is by a method selected from the group consisting of intravenous administration, intraperitoneal administration, intramuscular administration, intracoronary administration, intraarterial administration, subcutaneous administration, transdermal delivery, intratracheal administration, subcutaneous administration, intraarticular administration, intraventricular administration, inhalation, intracerebral, nasal, oral, pulmonary administration, impregnation of a catheter, and direct injection into a tissue or tumor.

Another aspect of the invention relates to a method of treating cancer in a subject comprising administering to the subject a therapeutically effective amount of a pharmaceutical composition comprising the recombinant oncolytic virus described herein to thereby treat the cancer. In one embodiment, the cancer is selected from the group consisting of basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma (GBM); hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NEIL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. In one embodiment, the cancer is brain cancer. In one embodiment, the brain cancer is glioma or glioblastoma. In one embodiment, administration is by a method selected from the group consisting of intravenous administration, intraperitoneal administration, intramuscular administration, intracoronary administration, intraarterial administration, subcutaneous administration, transdermal delivery, intratracheal administration, subcutaneous administration, intraarticular administration, intraventricular administration, inhalation, intracerebral, nasal, oral, pulmonary administration, impregnation of a catheter, and direct injection into a tissue or tumor.

Definitions

An "oncolytic virus" is any virus which typically is able to kill a tumor cell (non-resistant) by infecting the tumor cell.

An oncolytic virus is "replication-selective" if it is more capable of replicating or is capable of replicating to a greater extent (e.g. burst size) in a tumor cell of a subject than in a non-tumor cell of the subject.

The term "in expressible form" when used in the context of a DNA molecule means operably linked (e.g., located within functional distance) to sequences necessary for transcription of the DNA into RNA by the RNA polymerase transcription machinery found in eukaryotic cells (e.g., promoter sequences, and other 5' regulatory sequences). One example is a DNA molecule in the context of an expression vector. Expression can refer to transcription of DNA into RNA, and when protein coding sequences are involved, expression may also encompass translation of the mRNA into protein. Viral expression vectors may comprise the viral genome in the context of a virion that is used to infect a cell.

The term "operably linked" is used herein to refer to a functional relationship of one nucleic acid sequence to another nucleic acid sequence. Nucleic acid sequences are "operably linked" when placed into a functional relationship with one another. For example, a promoter or enhancer is operably linked to a coding sequence if it affects the transcription of the sequence; or a ribosome binding site is operably linked to a coding sequence if it is positioned so as to facilitate translation. The DNA sequences being linked may be contiguous, or separated by intervening sequences, and when necessary in the same reading phase and/or appropriate orientation. Linking is accomplished, for example, by ligation at convenient restriction sites. If such sites do not exist, the synthetic oligonucleotide adaptors or linkers are used in accordance with conventional practice.

The term "heterologous" is used herein to describe the relationship of one nucleic acid or amino acid sequence to one or more different nucleic acid or amino acid sequences, respectively. The term heterologous, in reference to two or more such sequences, indicates that the different sequences are found in nature within separate, different and distinct larger nucleic acids or polypeptides. The joining of heterologous sequences creates a non-naturally occurring juxtaposition of sequences. Such joining is the product of engineering performed in the laboratory. When such amino acid sequences are joined, the resulting protein is referred to herein as a fusion protein. The products of such joining are referred to as "recombinant".

The term "isolated" when used in reference to a nucleic acid sequence refers to the fact that the nucleic acid sequence is removed from the context of other nucleic acid sequences in which it is present in nature (e.g., in the context of a chromosome). The nucleic acids of the invention are typically present in isolated form.

The term "purified" when used in reference to a polypeptide or virus refers to the fact that it is removed from the majority of other cellular components from which it was generated or in which it is typically present in nature. The polypeptides and viruses described herein may be in a state where they are purified or semi-purified.

As the term is used herein, "transfection" refers to the introduction of nucleic acid into a cell (e.g, for the purpose of propagation and/or expression of the nucleic acid by the cell). Examples of methods of transfection are electroporation, calcium phosphate, lipofection, and viral infection utilizing a viral vector. Often nucleic acid is introduced into a cell in expressible form. That means that the nucleic acid is in the appropriate context of regulatory sequences such that the cellular machinery will recognize it and process it (e.g., transcribe RNA from DNA, translate protein from RNA). In one embodiment, a nucleic acid is in expressible form when it is inserted into an expression vector in the proper orientation to confer expression.

An "effective amount" as the term is used herein, is used to refer to an amount that is sufficient to produce at least a reproducibly detectable amount of the desired results. An effective amount will vary with the specific conditions and circumstances. Such an amount can be determined by the skilled practitioner for a given situation.

The term "therapeutically effective amount" refers to an amount that is sufficient to produce a therapeutically significant reduction in one or more symptoms of the condition when administered to a typical subject who has the condition. A therapeutically significant reduction in a symptom is, e.g. about 10%, about 20%, about 30%, about 40%, about 50%, about 60%, about 70%, about 80%, about 90%, about 100%, or more as compared to a control or non-treated subject.

The term "treat" or "treatment" refers to therapeutic treatment wherein the object is to eliminate or lessen symptoms. Beneficial or desired clinical results include, but are not limited to, elimination of symptoms, alleviation of symptoms, diminishment of extent of condition, stabilized (i.e., not worsening) state of condition, delay or slowing of progression of the condition.

The terms "patient", "subject" and "individual" are used interchangeably herein, and refer to an animal, particularly a human, to whom treatment including prophylaxic treatment is provided. This includes human and non-human animals. The term "non-human animals" and "non-human mammals" are used interchangeably herein includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model. Patient or subject includes any subset of the foregoing, e.g., all of the above, but excluding one or more groups or species such as humans, primates or rodents. A subject can be male or female. A subject can be a fully developed subject (e.g., an adult) or a subject undergoing the developmental process (e.g., a child, infant or fetus).

Preferably, the subject is a mammal. The mammal can be a human, non-human primate, mouse, rat, dog, cat, horse, or cow, but are not limited to these examples. Mammals other than humans can be advantageously used as subjects that represent animal models of disorders associated with unwanted neuronal activity. In addition, the methods and compositions described herein can be used to treat domesticated animals and/or pets.

The term "mammal" refers to any animal classified as a mammal, including humans, non-human primates, domestic and farm animals, and zoo, sports, or pet animals, such as dogs, cats, cattle, horses, sheep, pigs, goats, rabbits, etc.

The terms "cell proliferative disorder" and "proliferative disorder" refer to disorders that are associated with some degree of abnormal cell proliferation. In one embodiment, the cell proliferative disorder is a tumor. In one embodiment, the cell proliferative disorder is cancer.

The term "tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein. In one embodiment, tumors are benign. Examples of benign tumors include, without limitation, schwannomas, lipoma, chondroma, adenomas (e.g, hepatic adenoma), and benign brain tumors (e.g., glioma, astrocytoma, meningioma).

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

The term "inhibiting tumor cell growth or proliferation" means decreasing A tumor cell's growth or proliferation by at least 10%, 20%, 30%, 40%, 50%, 60%, 70%, 80%, 90%, 95%, or 100%, and includes inducing cell death in a cell or cells within a cell mass.

The term "tumor progression" refers to all stages of a tumor, including tumorigenesis, tumor growth and proliferation, invasion, and metastasis.

The term "inhibiting tumor progression" means inhibiting the development, growth, proliferation, or spreading of a tumor, including without limitation the following effects: inhibition of growth of cells in a tumor, (2) inhibition, to some extent, of tumor growth, including slowing down or complete growth arrest; (3) reduction in the number of tumor cells; (4) reduction in tumor size; (5) inhibition (i.e., reduction, slowing down or complete stopping) of tumor cell infiltration into adjacent peripheral organs and/or tissues; (6) inhibition (i.e. reduction, slowing down or complete stopping) of metastasis; (7) increase in the length of survival of a patient or patient population following treatment for a tumor; and/or (8) decreased mortality of a patient or patient population at a given timepoint following treatment for a tumor.

A tumor "responds" to a particular agent if tumor progression is inhibited as defined above.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, bacterial artificial chromosomes (BAC), P1-derived artificial chromosome (PAC), yeast artificial chromosome (YAC), human artificial chromosome (HAC), DNA or RNA expression vectors associated with cationic condensing agents, DNA or RNA expression vectors encapsulated in liposomes, and certain eukaryotic cells, such as producer cells. Expression may be achieved in any appropriate host cell that has been transformed, transfected or infected with the expression vector. Suitable host cells include prokaryotes, yeast and higher eukaryotic cells. Preferably the host cells employed are *E. coli*, yeast or a mammalian cell, such as a primary cell or cell line such as COS or CHO.

BRIEF DESCRIPTION OF THE DRAWINGS

FIGS. 1A-1D contain graphical representations of experimental results that indicate differential sensitivities of glioblastoma multiforme (GBM) cells to S-TRAIL-mediated apoptosis and oncolytic herpes simplex virus (oHSV)-mediated oncolysis. FIG. 1A Screening of different GBM lines reveals differential sensitivities to S-TRAIL-mediated apoptosis and oHSV-mediated oncolysis. Established GBM lines (U87, LN229, U251, and Gli36) and primary glioma stem cell (GSC) lines (BT74, GBM4, GBM6, and GBM8F) were treated with different concentrations of purified S-TRAIL and assayed for viability at 48 hours post-treatment (top row), and for caspase-3/7 activity at 18 hours post-treatment (second row). Established GBM lines and primary GSC lines were infected with oHSV at multiplicities of infection (MOIs) 0.2 and 1 and assayed for viability at 72 hours postinfection (third row), and virus titration on Vero cells using the supernatant of oHSV-infected GBM cell lines (MOI1, bottom row). FIGS. 1B, 1C. Pharmacodynamics of oHSV in vitro. LN229-RmC and GBM8F-RmC were infected with oHSV-Fluc at MOI=1. Viral replication indicated by (FIG. 1B) firefly luciferase (Fluc) activity and tumor cell viability indicated by (FIG. 1C) *Renilla* luciferase (Rluc) activity were monitored by dual Fluc and Rluc bioluminescence imaging, respectively at different time points. FIG. 1D. Pharmacodynamics of oHSV in vivo. Mice- (n=3 per line) bearing intracranial LN229-RmC (left) or GBM8F-RmC (right) GBMs were injected with oHSV-Fluc intratumorally and viral distribution was followed by Fluc bioluminescence imaging at different indicated times. One representative image of mice and the average Fluc bioluminescence intensities are shown. *$P<0.05$. Error bars indicate SD.

FIGS. 2A-Caspase-3/7 activity and cell viability of (FIGS. 2A, 2C) LN229 and (FIGS. 2B, 2D) GBM8F treated with purified S-TRAIL (100 ng/ml), oHSV (multiplicity of infection (MOI)=1) or both oHSV and S-TRAIL in the presence or absence of pan-caspase inhibitor, Z-VAD-FMK (20 µmol/l). *$P<0.05$ in the comparison of oHSV plus S-TRAIL treatment group with other groups. FIG. 2E, 2F. Immunoblot analysis using cleaved poly-ADP ribose polymerase (PARP) antibody on whole cell lysates prepared from LN229 and GBM8F cells treated with purified S-TRAIL (100 ng/ml), oHSV (MOI=1) or both oHSV and S-TRAIL in the presence or absence of pan-caspase inhibitor, Z-VAD-FMK (20 µmol/l). Cleaved PARP expression was normalized to α-tubulin expression. *$P<0.05$ in the comparison of oHSV plus tumor necrosis factor-related apoptosis-inducing ligand (TRAIL) to TRAIL. Error bars indicate SD.

FIGS. 3A, 3B. Cell viability of GBM cells assessed by *Renilla* luciferase (Rluc) bioluminescence at different time points. (FIG. 3A) LN229-RmC and (FIG. 3B) GBM8F-RmC were infected with oHSV or oHSV-TRAIL at multiplicity of infection (MOI)=1. *$P<0.05$ in the comparison of oHSV-TRAIL to control and to oHSV. Error bars indicate SD. FIG. 3C. Immunoblot analysis using antibodies against caspase-8, -9, cleaved poly-ADP ribose polymerase (PARP), Bcl2, phospho-ERK, ERK, phospho-c-Jun N-terminal kinase (JNK), JNK, phospho-p38, and p38 on whole cell lysates prepared from LN229 and GBM8F cells untreated, or treated with oHSV, oHSV-TRAIL (MOI=1) or S-TRAIL for 18 hours. α-Tubulin was used as a loading control.

FIGS. 4A-4D contain graphs and photographs of experimental results that indicate Oncolytic herpes simplex virus (oHSV)-tumor necrosis factor-related apoptosis-inducing ligand (TRAIL)-mediated apoptosis in resistant glioblastoma multiformes (GBMs) depends on c-Jun N-terminal kinase (JNK) activation and ERK inhibition. FIG. 4A. Immunoblot analysis using antibodies against JNK, phosho-JNK, and cleaved poly-ADP ribose polymerase (PARP), on whole cell lysate prepared from LN229 cells treated with oHSV, oHSV-TRAIL (multiplicity of infection (MOI)=1) or control in the absence (−) and presence (+) of JNK inhibitor (SP600125, 20 µmol/l) for 18 hours. FIG. 4B. Caspase 3/7 activity of LN229 cells treated with oHSV, oHSV-TRAIL (MOI=1), or control for 20 hours in the absence (−) and presence (+) of JNK inhibitor. *$P<0.05$ in the comparison of oHSV-TRAIL treated cells in the absence and presence of JNK. FIG. 4C. Immunoblot analysis using antibodies against ERK, phosho ERK, and cleaved PARP on whole cell lysate prepared from LN229 cells treated with S-TRAIL (100 ng/ml) in the absence (−) and presence (+) of ERK inhibitor (U0126, 20 µmol/l) for 18 hours. α-Tubulin was used as a loading control. FIG. 4D. Cell viability assay showing the % viable LN229 cells after treatment with different combinations of U0126 (20 µmol/l) and TRAIL (100 ng/ml) for 48 hours. *P<0.05 JNK inhibitor group in the comparison with control (in FIG. 4B) and ERK inhibitor and S-TRAIL treatment group in the comparison with other treatment groups (in FIG. 4D). Error bars indicate SD.

FIG. 5A. Timeline and survival curves of LN229-FmC GBM-bearing mice treated with oHSV, oHSV-TRAIL, or control (phosphate-buffered saline (PBS)). P=0.038 in oHSV and oHSV-TRAIL comparison, log-rank test. FIG. 5B. X-gal staining revealing virus-infected areas. oHSV-injected (left) and oHSV-TRAIL-injected (right) tumor sections. Original magnification ×20. FIG. 5C. Immunofluorescence of cleaved caspase-3 staining on brain sections from LN229-FmC GBM-bearing mice injected with oHSV, oHSV-TRAIL, or PBS (control). Original magnification ×20. FIG. 5D. Plot showing the percentage of cleaved caspase-3 positive LN229-FmC GBM cells on brain sections. *P<0.05 in the comparison of oHSV-TRAIL to control and to oHSV. n=3 in each group. Error bars indicate SD.

FIG. 6A. In vitro invasion assay. Photomicrographs and graph showing the change in cell invasion after treatment with oHSV or oHSV-TRAIL in GBM8F glioma line. Multiplicity of infection (MOI)=1. *P<0.05 in the comparison of oHSV-TRAIL to control and to oHSV. FIG. 6B. In vivo invasion assay. Mice-bearing intracranial GBM8-FmC gliomas were injected with oHSV, oHSV-TRAIL, or phosphate-buffered saline (PBS) (control) and mice were sacrificed on day 14 and invasion of the GBM cells on brain sections was evaluated. Photomicrograph of hematoxylin and eosin (H&E) staining of GBM8F tumor cell invasion towards adjacent normal brain tissue and illustration of brain revealing GBM8F implantation-site and pictured-site. n=3 per group. *P<0.05 in the comparison of oHSV-TRAIL to control and to oHSV. Error bars indicate SD.

FIG. 9A. Viral replication monitored by Fluc bioluminescence imaging in LN229-Rluc-mCherry and GBM8F-Rluc-mCherry cells infected with oHSV-Fluc at various MOIs (0-2). Imaging was performed 48 hours post infection. FIG. 9B. Tumor cell viability monitored by Rluc bioluminescence imaging in LN229-Rluc-mCherry and GBM8F-Rluc-mCherry cells infected with oHSV-Fluc at various MOIs (0-2). Imaging was performed 48 hours post infection. Error bars indicate standard deviation. *, P<0.05.

FIGS. 10A-10E contain graphs of experimental results that indicate oHSV-TRAIL virus yield is similar to oHSV yield and mediates potent cytotoxicity in resistant GBM cells. FIG. 10A. oHSV, oHSV-Fluc and oHSV-TRAIL infected GBM cells at MOI=0.8 were harvested 24 hours after infection and the virus yield was quantified using plaque assay on Vero cells. FIG. 10B. The concentrations of S-TRAIL determined by ELISA in conditioned media of LN229 GBM cells infected with oHSV-TRAIL at different MOIs. FIGS. 10C-10D. Cell viability of LN229-Rluc-mCherry cells (FIG. 10C) and GBM8F-Rluc-mCherry cells (FIG. 10D) infected with oHSV or oHSV-TRAIL assessed by Rluc bioluminescence imaging 48 hours post infection. Error bars indicate standard deviation. *, p<0.05. FIG. 10E. FACS analysis showing the percentage of apoptotic cells (Annexin V positive, PI negative) following infection with oHSV or oHSV-TRAIL for 24 hours.

DETAILED DESCRIPTION OF THE INVENTION

Figure 1A:
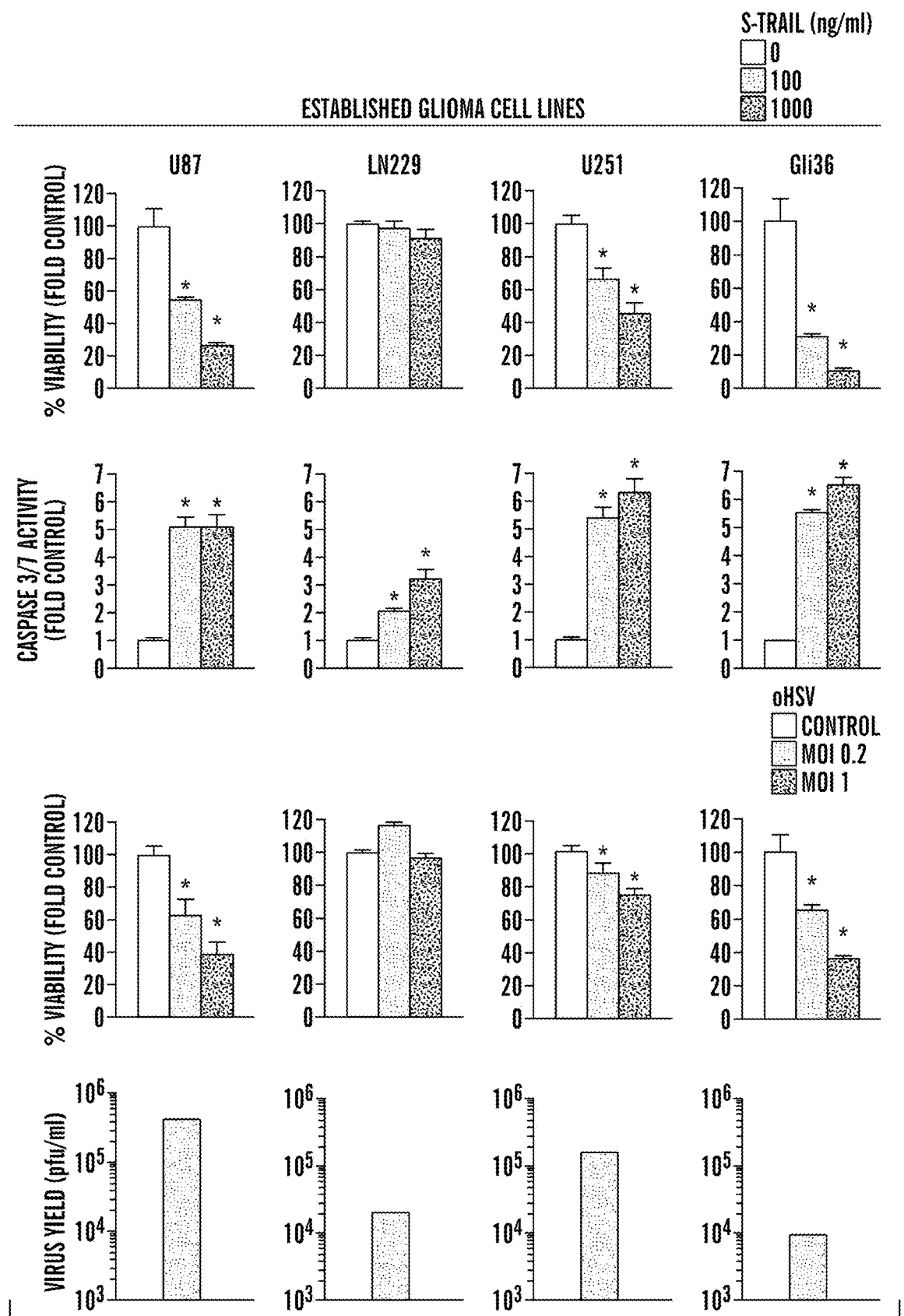
Figure 1A:
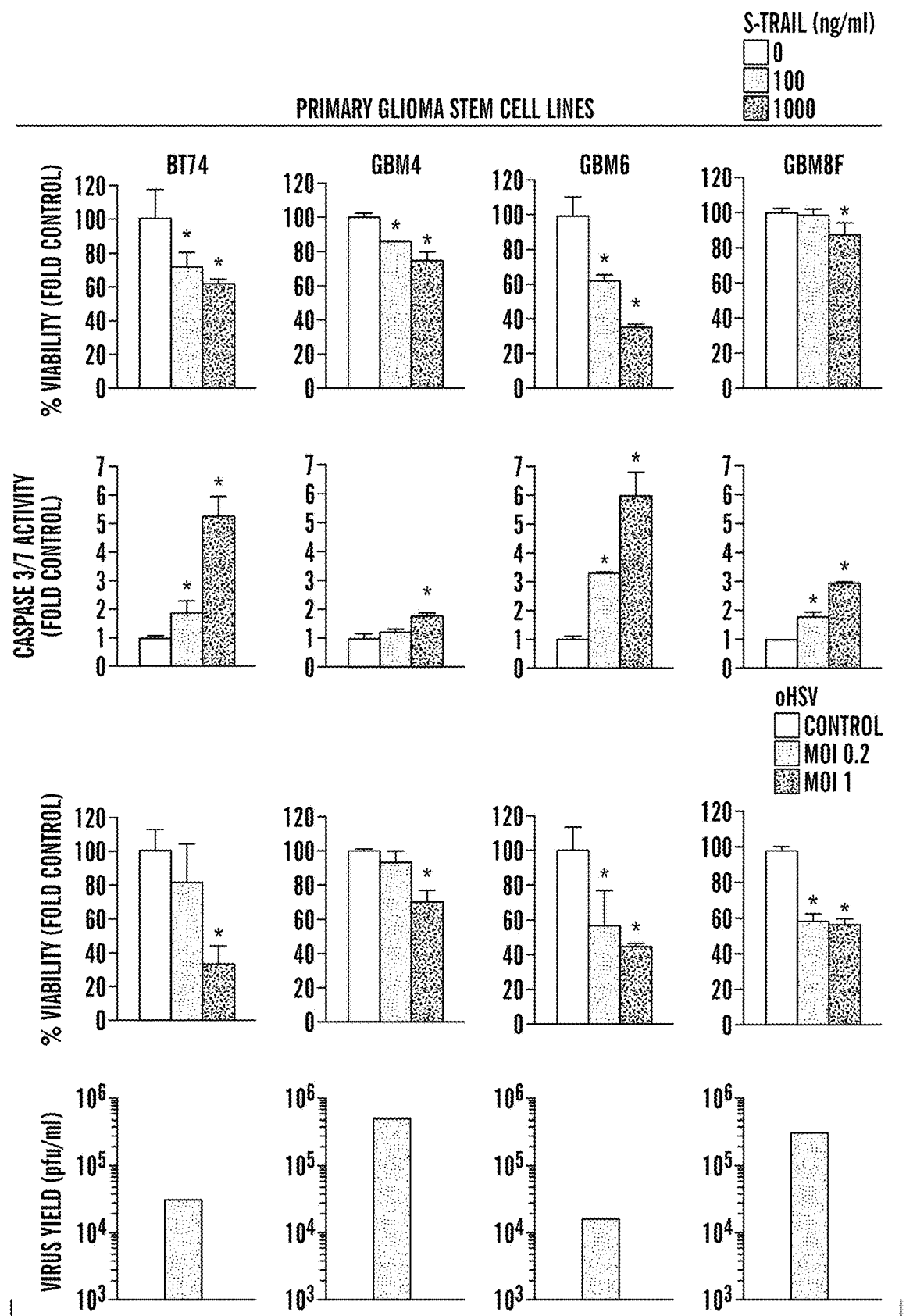
Figure 1D:
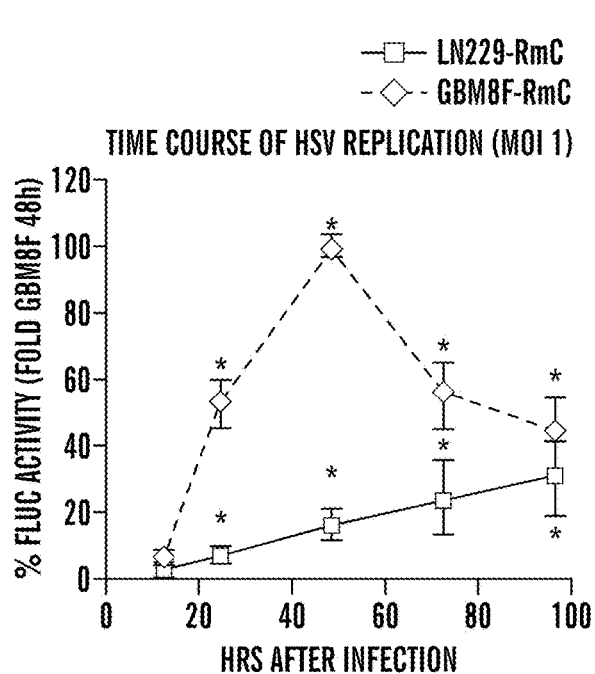
Figure 1D:
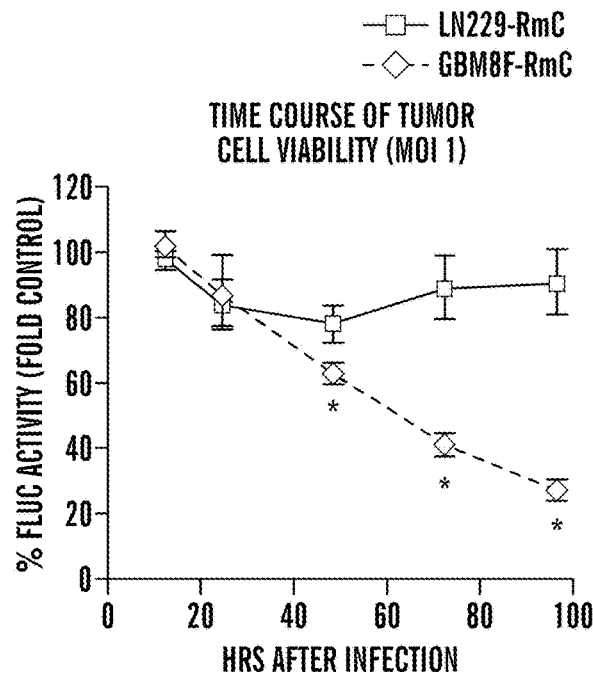
Figure 1D:
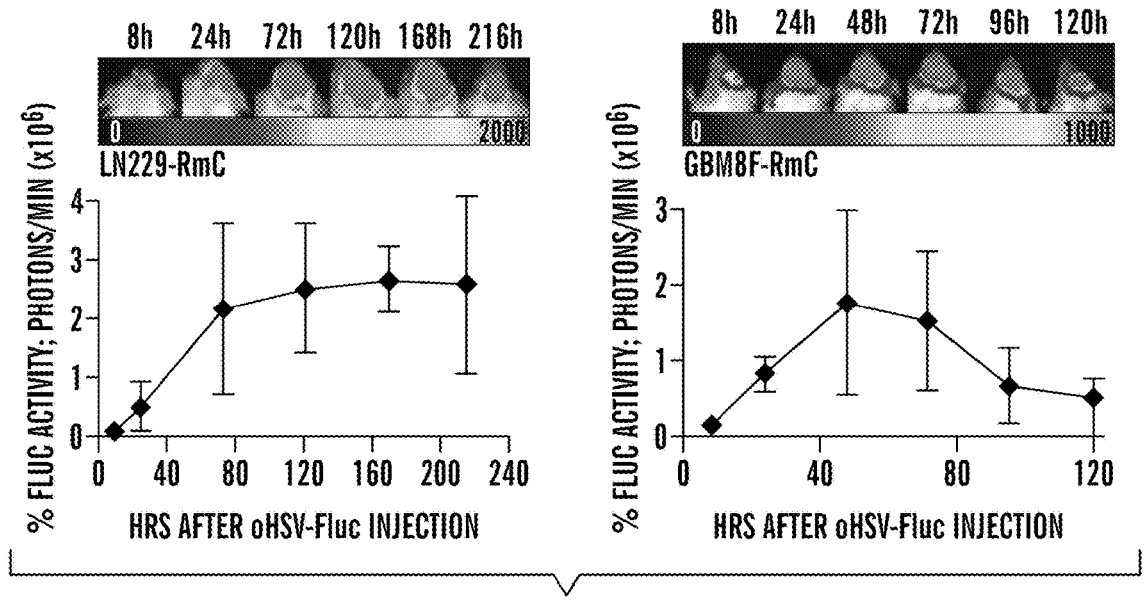

Only a subset of cancer patients inoculated with oncolytic herpes simplex virus (oHSV) type-1 has shown objective response in phase 1 and 2 clinical trials. This has raised speculations whether resistance of tumor cells to oHSV therapy may be a limiting factor. In the experiments disclosed herein, established and patient derived primary glioblastoma multiforme (GBM) stem cell lines (GSC) resistant to oHSV and also to tumor necrosis factor-related apoptosis-inducing ligand (TRAIL) were identified that had recently shown promise in preclinical and initial clinical studies. A recombinant oHSV bearing a secretable TRAIL (oHSV-TRAIL) was created and used to test the hypothesis that oHSV-TRAIL could be used as a cancer therapeutic to target a broad spectrum of resistant tumors in a mechanism-based manner. Using the identified resistant GBM lines, oHSV- TRAIL was shown to downregulate extracellular signal-regulated protein kinase (ERK)-mitogen-activated protein kinase (MAPK) and upregulate c-Jun N-terminal kinase (JNK) and p38-MAPK signaling, which primed resistant GBM cells to apoptosis via activation of caspase-8, -9, and -3. Further, it was shown that oHSV-TRAIL inhibited tumor growth and invasiveness and increased survival of mice bearing resistant intracerebral tumors without affecting the normal tissues. This study sheds new light on the mechanism by which oHSV and TRAIL function in concert to overcome therapeutic-resistance, and provides an oncolytic virus based platform to target a broad spectrum of different cancer types. Aspects of the invention relate to the discovery of this oncolytic virus based platform.

One aspect of the invention relates to a recombinant oncolytic virus that comprises a heterologous nucleic acid sequence encoding TRAIL, or a biologically active fragment thereof, in expressible form. Another aspect of the invention relates to a nucleic acid comprising the genome of the oncolytic virus. Such a nucleic acid may be in the form of an artificial chromasome, such as a bacterial artificial chromosome (BAC), a P1-derived artificial chromosome (PAC), a yeast artificial chromosome (YAC), or a human artificial chromosome (HAC). The invention also encompasses a host cell or population thereof, comprising the oncolytic virus and/or the nucleic acid comprising the genome of the oncolytic virus.

Oncolytic Viruses

Numerous oncolytic viruses are known in the art and are described, for example, in Kirn et al. (1999, In: Gene Therapy of Cancer, Academic Press, San Diego, Calif., pp. 235-248), any of which is envisioned for use in the invention. By way of example, appropriate oncolytic viruses include type 1 herpes simplex viruses, type 2 herpes simplex viruses, vesicular stomatitis viruses, oncolytic adenovirus (U.S. Pat. No. 8,216,819), Newcastle disease viruses, vaccinia viruses, and mutant strains of these viruses. In one embodiment, the oncolytic virus is replication-selective or replication-competent. In one embodiment, the oncolytic virus is replication-incompetent.

The oncolytic viruses useful in the present methods and compositions are, in some embodiments, replication-selective. It is understood that an oncolytic virus may be made replication-selective if replication of the virus is placed under the control of a regulator of gene expression such as, for example, the enhancer/promoter region derived from the 5'-flank of the albumin gene (e.g. see Miyatake et al., 1997, J. Virol. 71:5124-5132). By way of example, the main transcriptional unit of an HSV may be placed under transcriptional control of the tumor growth factor-beta (TGF-β) promoter by operably linking HSV genes to the TGF-β promoter. It is known that certain tumor cells overexpress TGF-β, relative to non-tumor cells of the same type. Thus, an oncolytic virus wherein replication is subject to transcriptional control of the TGF-β promoter is replication-selective, in that it is more capable of replicating in the certain tumor cells than in non-tumor cells of the same type. Similar replication-selective oncolytic viruses may be made using any regulator of gene expression which is known to selectively cause overexpression in an affected cell. The replication-selective oncolytic virus may, for example, be an HSV-1 mutant in which a gene encoding ICP34.5 is mutated or deleted.

An oncolytic virus in accordance with the present invention can further comprise other modifications in its genome. For example, it can comprise additional DNA inserted into the UL44 gene. This insertion can produce functional inactivation of the UL44 gene and the resulting lytic phenotype, or it may be inserted into an already inactivated gene, or substituted for a deleted gene.

The oncolytic virus may also have incorporated therein one or more promoters that impart to the virus an enhanced level of tumor cell specificity. In this way, the oncolytic virus may be targeted to specific tumor types using tumor cell-specific promoters. The term "tumor cell-specific promoter" or "tumor cell-specific transcriptional regulatory sequence" or "tumor-specific promoter" or "tumor-specific transcriptional regulatory sequence" indicates a transcriptional regulatory sequence, promoter and/or enhancer that is present at a higher level in the target tumor cell than in a normal cell. For example, the oncolytic virus for use in the invention may be under the control of an exogenously added regulator such as tetracycline (U.S. Pat. No. 8,2366,941).

In one embodiment, the oncolytic virus (e.g, oHSV) vector of the invention is engineered to place at least one viral protein necessary for viral replication under the control of a tumor-specific promoter. Or, alternatively a gene (a viral gene or exogenous gene) that encodes a cytotoxic agent can be put under the control of a tumor-specific promoter. By cytotoxic agent as used here is meant any protein that causes cell death. For example, such would include ricin toxin, diphtheria toxin, or truncated versions thereof. Also, included would be genes that encode prodrugs, cytokines, or chemokines. Such viral vectors may utilize promoters from genes that are highly expressed in the targeted tumor such as the epidermal growth factor receptor promoter (EGFr) or the basic fibroblast growth factor (bFGF) promoter, or other tumor associated promoters or enhancer elements.

Oncolytic Herpes Simplex Virus (oHSV)

One such oncolytic virus for use in the present invention is oncolytic herpes simplex virus (oHSV). The oHSV will comprise one or more exogenous nucleic acids encoding for one or more of the polypeptides described herein. Methods of generating an oHSV comprising such an exogenous nucleic acid are known in the art. The specific position of insertion of the nucleic acid into the oHSV genome can be determined by the skilled practitioner.

Oncolytic herpes simplex viruses (oHSV) are known in the art and are described, for example, in Kim et al. (1999, In: Gene Therapy of Cancer, Academic Press, San Diego, Calif., pp. 235-248), and include type 1 herpes simplex viruses and type 2 herpes simplex viruses. In one embodiment, the oHSV used in the methods, compositions, and kits of the invention is replication-selective or replication-competent such as one of the examples described herein. In one embodiment, the oHSV is replication-incompetent.

Herpes simplex 1 type viruses are among the preferred viruses, for example the variant of HSV-1 viruses that do not express functional ICP34.5 and thus exhibit significantly less neurotoxicity than their wild type counterparts. Such variants include without limitation oHSV-R3616, one of the HSV-1 viruses described in Coukos et al., Gene Ther. Mol. Biol. 3:79-89 (1998), and Varghese and Rabkin, Cancer Gene Therapy 9:967-978 (2002). Other exemplary HSV-1 viruses include 1716, R3616, and R4009. Other replication selective HSV-1 virus strains that can be used include, e.g., R47Δ (wherein genes encoding proteins ICP34.5 and ICP47 are deleted), G207 (genes encoding ICP34.5 and ribonucleotide reductase are deleted), NV1020 (genes encoding UL24, UL56 and the internal repeat are deleted), NV1023 (genes encoding UL24, UL56, ICP47 and the internal repeat are deleted), 3616-UB (genes encoding ICP34.5 and uracil DNA glycosylase are deleted), G92Δ (in which the albumin promoter drives transcription of the essential ICP4 gene), hrR3 (the gene encoding ribonucleotide reductase is deleted), and R7041 (Us3 gene is deleted) and HSV strains that do not express functional ICP34.5.

oHSV for use in the methods and compositions described herein is not limited to one of the HSV-1 mutant strains described herein. Any replication-selective strain of a herpes simplex virus may be used. In addition to the HSV-1 mutant strains described herein, other HSV-1 mutant strains that are replication selective have been described in the art. Furthermore, HSV-2, mutant strains such as, by way of example, HSV-2 strains 2701 (RL gene deleted), Delta RR (ICP10PK gene is deleted), and FusOn-H2 (ICP10 PK gene deleted) can also be used in the methods and compositions described herein.

Non-laboratory strains of HSV can also be isolated and adapted for use in the invention (U.S. Pat. No. 7,063,835). Furthermore, HSV-2 mutant strains such as, by way of example, HSV-2 strains HSV-2701, HSV-2616, and HSV-2604 may be used in the methods of the invention.

In a one embodiment, the oHSV is G47Δ. G47Δ is a third generation virus, which contains 1) a mutation of ICP6, which targets viral deletion to tumor cells, 2) a deletion of γ34.5, which encodes ICP34.5 and blocks eIF2a phosphorylation and is the major viral determinant of neuropathogenicity, and 3) an additional deletion of the ICP47 gene and US11 promoter, so that the late gene US11 is now expressed as an immediate-early gene and able to suppress the growth inhibited properties of γ34.5 mutants. Deletion of ICP47 also abrogates HSV-1 inhibition of the transporter associated with antigen presentation and MEW class 1 downregulation (Todo et al., Proc. Natl. Acad. Sci. USA, 98:6396-6401 (2001)).

TRAIL

The oncolytic virus described herein comprises a nucleic acid sequence that encodes TRAIL, or a biologically active fragment thereof, incorporated into the virus genome in expressible form. As such the oncolytic virus serves as a vector for delivery of TRAIL to the infected cells. The invention envisions the use of various forms of TRAIL, such as those described herein, including without limitation, a secreted form of TRAIL or a functional domain thereof (e.g., a secreted form of the extracellular domain), multimodal TRAIL, or a therapeutic TRAIL module, therapeutic TRAIL domain (e.g., the extracellular domain) or therapeutic TRAIL variant (examples of each of which are described in WO2012/106281), and also fragments, variants and derivatives of these, and fusion proteins comprising one of these TRAIL forms such as described herein.

TRAIL is normally expressed on both normal and tumor cells as a non covalent homotrimeric type-II transmembrane protein (memTRAIL). In addition, a naturally occurring soluble form of TRAIL (solTRAIL) can be generated due to alternative mRNA splicing or proteolytic cleavage of the extracellular domain of memTRAIL and thereby still retaining tumor-selective pro-apoptotic activity. TRAIL utilizes an intricate receptor system comprising four distinct membrane receptors, designated TRAIL-R1, TRAIL-R2, TRAIL-R3 and TRAIL-R4. Of these receptors, only TRAIL-R1 and TRAIL-2 transmit an apoptotic signal. These two receptors belong to a subgroup of the TNF receptor family, the so-called death receptors (DRs), and contain the hallmark intracellular death domain (DD). This DD is critical for apoptotic signaling by death receptors (J. M. A. Kuijlen et al., Neuropathology and Applied Neurobiology, 2010 Vol. 36 (3), pp. 168-182).

Apoptosis is integral to normal, physiologic processes that regulate cell number and results in the removal of unnecessary or damaged cells. Apoptosis is frequently dysregulated in human cancers, and recent advancements in the understanding of the regulation of programmed cell death pathways has led to the development of agents to reactivate or activate apoptosis in malignant cells. This evolutionarily conserved pathway can be triggered in response to damage to key intracellular structures or the presence or absence of extracellular signals that provide normal cells within a multicellular organism with contextual information.

Without meaning to be bound by theory, TRAIL activates the "extrinsic pathway" of apoptosis by binding to TRAIL-R1 and/or TRAIL-R2, whereupon the adaptor protein Fas-associated death domain and initiator caspase-8 are recruited to the DD of these receptors. Assembly of this "death-inducing signaling complex" (DISC) leads to the sequential activation of initiator and effector caspases, and ultimately results in apoptotic cell death. The extrinsic apoptosis pathway triggers apoptosis independently of p53 in response to pro-apoptotic ligands, such as TRAIL. TRAIL-R1 can induce apoptosis after binding non-cross-linked and cross-linked sTRAIL. TRAIL-R2 can only be activated by cross-linked sTRAIL. Death receptor binding leads to the recruitment of the adaptor FADD and initiator procaspase-8 and 10 to rapidly form the DISC. Procaspase-8 and 10 are cleaved into its activated configuration caspase-8 and 10. Caspase-8 and 10 in turn activate the effector caspase-3, 6 and 7, thus triggering apoptosis.

In certain cells, the execution of apoptosis by TRAIL further relies on an amplification loop via the "intrinsic mitochondrial pathway" of apoptosis. The mitochondrial pathway of apoptosis is a stress-activated pathway, e.g., upon radiation, and hinges on the depolarization of the mitochondria, leading to release of a variety of pro-apoptotic factors into the cytosol. Ultimately, this also triggers effector caspase activation and apoptotic cell death. This mitochondrial release of pro-apoptotic factors is tightly controlled by the Bcl-2 family of pro- and anti-apoptotic proteins. In the case of TRAIL receptor signaling, the Bcl-2 homology (BH3) only protein 'Bid' is cleaved into a truncated form (tBid) by active caspase-8. Truncated Bid subsequently activates the mitochondrial pathway.

TRAIL-R3 is a glycosylphosphatidylinositol-linked receptor that lacks an intracellular domain, whereas TRAIL-R4 only has a truncated and non-functional DD. The latter two receptors are thought, without wishing to be bound or limited by theory, to function as decoy receptors that modulate TRAIL sensitivity. Evidence suggests that TRAIL-R3 binds and sequesters TRAIL in lipid membrane microdomains. TRAIL-R4 appears to form heterotrimers with TRAIL-R2, whereby TRAIL-R2-mediated apoptotic signaling is disrupted. TRAIL also interacts with the soluble protein osteoprotegerin Diffuse expression of TRAIL has been detected on liver cells, bile ducts, convoluted tubules of the kidney, cardiomyocytes, lung epithelia, Leydig cells, normal odontogenic epithelium, megakaryocytic cells and erythroid cells. In contrast, none or weak expression of TRAIL was observed in colon, glomeruli, Henle's loop, germ and Sertoli cells of the testis, endothelia in several organs, smooth muscle cells in lung, spleen and in follicular cells in the thyroid gland. TRAIL protein expression was demonstrated in glial cells of the cerebellum in one study. Vascular brain endothelium appears to be negative for TRAIL-R1 and weakly positive for TRAIL-R2. With regard to the decoy receptors, TRAIL-R4 and TRAIL-R3 have been detected on oligodendrocytes and neurones.

TRAIL-R1 and TRAIL-R2 are ubiquitously expressed on a variety of tumor types. In a study on 62 primary GBM tumor specimens, TRAIL-R1 and TRAIL-R2 were expressed in 75% and 95% of the tumors, respectively. Of note, a statistically significant positive association was identified between agonistic TRAIL receptor expression and survival. Highly malignant tumors express a higher amount of TRAIL receptors in comparison with less malignant tumors or normal tissue. In general TRAIL-R2 is more frequently expressed on tumor cells than TRAIL-R1.

"Tumor necrosis factor-related apoptosis-inducing ligand" or "TRAIL" as used herein refers to the 281 amino acid polypeptide having the amino acid sequence of: MAMMEVQGGPSLGQTCVLIVIFTVLLQSLCVAVTYVYFTNELKQMQDKYSKSGIAC FLKEDDSYWDPNDEESMNSPCWQVKWQLRQLVRKMILRT SEETISTVQEKQQNISPL VRERGPQRVAAHITGTRGRSNTLSSPNSKNEKALGRKINSWESSRSGHSFLSNLHLRN GELVIHEKGFYYIYSQTYFRFQEEIKENTKNDKQMVQYIYKYTSYPDPILLMKSARNS CWSKDAEYGLYSIYQGGIFELKENDRIFVSVTNEHLIDMDHEASFFGAFLVG (SEQ ID NO: 1), as described by, e.g., NP_003801.1, together with any naturally occurring allelic, splice variants, and processed forms thereof. Typically, TRAIL refers to human TRAIL. The term TRAIL, in some embodiments of the aspects described herein, is also used to refer to truncated forms or fragments of the TRAIL polypeptide, comprising, for example, specific TRAIL domains or residues thereof. The amino acid sequence of the human TRAIL molecule as presented in SEQ ID NO: 1 comprises an N-terminal cytoplasmic domain (amino acids 1-18), a transmembrane region (amino acids 19-38), and an extracellular domain (amino acids 39-281). The extracellular domain comprises the TRAIL receptor-binding region. TRAIL also has a spacer region between the C-terminus of the transmembrane domain and a portion of the extracellular domain This spacer region, located at the N-terminus of the extracellular domain, consists of amino acids 39 through 94 of SEQ ID NO: 1. Amino acids 138 through 153 of SEQ ID NO: 1 correspond to a loop between the sheets of the folded (three dimensional) human TRAIL protein.

In one embodiment, the TRAIL comprises the extracellular domain of TRAIL (e.g., human trial). In one embodiment, the TRAIL is a fusion protein comprising one or more domains of TRAIL (e.g., the extracellular domain) fused to a heterologous sequence. In one embodiment, the TRAIL fusion protein further comprises a signal for secretion.

Preferably, the TRAIL protein and the nucleic acids encoding it, are derived from the same species as will be administered in the therapeutic methods described herein. In one embodiment, the nucleotide sequence encoding TRAIL and the TRAIL amino acid sequence is derived from a mammal. In one embodiment, the mammal is a human (human TRAIL). In one embodiment, the mammal is a non-human primate.

Fragments, Variants and Derivatives of TRAIL

Fragments, variants and derivatives of native TRAIL proteins for use in the invention that retain a desired biological activity of TRAIL, such as TRAIL apoptotic activity are also envisioned for delivery by the oncolytic virus vector. In one embodiment, the biological or apoptotic activity of a fragment, variant or derivative of TRAIL is essentially equivalent to the biological activity of the corresponding native TRAIL protein. In one embodiment, the biological activity for use in determining the activity is apoptotic activity. In one embodiment, 100% of the apoptotic activity is retained by the fragment, variant or derivative. In one embodiment less than 100%, activity is retained (e.g., 95%, 90%, 85%, 80%, 75%, 70%, 65%, 60%, 55%, 50%, 45%, 40%) as compared to the full length native TRAIL. Fragments, variants or derivatives which retain less activity (e.g., 34%, 30%, 25%, 20%, 10%, etc.) may also be of value in the therapeutic methods described herein and as such are also encompassed in the invention. One measurement of TRAIL apoptotic activity by a TRAIL variant or TRAIL domain is the ability to induce apoptotic death of Jurkat cells. Assay procedures for identifying biological activity of TRAIL variants by detecting apoptosis of target cells, such as Jurkat cells, are well known in the art. DNA laddering is among the characteristics of cell death via apoptosis, and is recognized as one of the observable phenomena that distinguish apoptotic cell death from necrotic cell death. Apoptotic cells can also be identified using markers specific for apoptotic cells, such as Annexin V, in combination with flow cytometric techniques, as known to one of skill in the art. Further examples of assay techniques suitable for detecting death or apoptosis of target cells include those described in WO2012/106281.

A variety of TRAIL fragments that retain the apoptotic activity of TRAIL are known in the art, and include biologically active domains and fragments disclosed in Wiley et al. (U.S. Patent Publication 20100323399).

TRAIL variants can be obtained by mutations of native TRAIL nucleotide sequences, for example. A "TRAIL variant," as referred to herein, is a polypeptide substantially homologous to a native TRAIL, but which has an amino acid sequence different from that of native TRAIL because of one or a plurality of deletions, insertions or substitutions. "TRAIL encoding DNA sequences" encompass sequences that comprise one or more additions, deletions, or substitutions of nucleotides when compared to a native TRAIL DNA sequence, but that encode a TRAIL protein or fragment thereof that is essentially biologically equivalent to a native TRAIL protein, i.e., has the same apoptosis inducing activity.

The variant amino acid or DNA sequence preferably is at least 70%, at least 75%, at least 80%, at least 85%, at least 90%, at least 91%, at least 92%, at least 93%, at least 94%, at least 95%, at least 96%, at least 97%, at least 98%, at least 99%, or more, identical to a native TRAIL sequence. The degree of homology or percent identity) between a native and a mutant sequence can be determined, for example, by comparing the two sequences using freely available computer programs commonly employed for this purpose on the world wide web.

Alterations of the native amino acid sequence can be accomplished by any of a number of known techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations include those disclosed by Walder et al. (Gene 42:133, 1986); Bauer et al. (Gene 37:73, 1985); Craik (BioTechniques, Jan. 1985, 12-19); Smith et al. (Genetic Engineering: Principles and Methods, Plenum Press, 1981); and U.S. Pat. Nos. 4,518,584 and 4,737,462, which are herein incorporated by reference in their entireties.

TRAIL variants can, in some embodiments, comprise conservatively substituted sequences, meaning that one or more amino acid residues of a native TRAIL polypeptide are replaced by different residues, and that the conservatively substituted TRAIL polypeptide retains a desired biological activity, i.e., apoptosis inducing activity or TRAIL apoptotic activity, that is essentially equivalent to that of the native TRAIL polypeptide. Examples of conservative substitutions include substitution of amino acids that do not alter the secondary and/or tertiary structure of TRAIL.

In other embodiments, TRAIL variants can comprise substitution of amino acids that have not been evolutionarily conserved. Conserved amino acids located in the C-terminal portion of proteins in the TNF family, and believed to be important for biological activity, have been identified. These conserved sequences are discussed in Smith et al. (Cell, 73:1349, 1993); Suda et al. (Cell, 75:1169, 1993); Smith et al. (Cell, 76:959, 1994); and Goodwin et al. (Eur. J. Immunol., 23:2631, 1993). Advantageously, in some embodiments, these conserved amino acids are not altered when generating conservatively substituted sequences. In some embodiments, if altered, amino acids found at equivalent positions in other members of the TNF family are substituted. Among the amino acids in the human TRAIL protein of SEQ ID NO:1 that are conserved are those at positions 124-125 (AH), 136 (L), 154 (W), 169 (L), 174 (L), 180 (G), 182 (Y), 187 (Q), 190 (F), 193 (Q), and 275-276 (FG) of SEQ ID NO:1. Another structural feature of TRAIL is a spacer region (i.e., TRAIL (39-94)) between the C-terminus of the transmembrane region and the portion of the extracellular domain that is believed to be important for biological apoptotic activity. In some embodiments, when the desired biological activity of TRAIL domain is the ability to bind to a receptor on target cells and induce apoptosis of the target cells substitution of amino acids occurs outside of the receptor-binding domain.

A given amino acid of a TRAIL domain can, in some embodiments, be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. TRAIL polypeptides comprising conservative amino acid substitutions can be tested in any one of the assays described herein to confirm that a desired TRAIL apoptotic activity of a native TRAIL molecule is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H).

Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class.

Particularly preferred conservative substitutions for use in the TRAIL variants described herein are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

Any cysteine residue not involved in maintaining the proper conformation of the multimodal TRAIL agent also can be substituted, generally with serine, to improve the oxidative stability of the molecule and prevent aberrant crosslinking. Conversely, cysteine bond(s) can be added to the multimodal TRAIL agent to improve its stability or facilitate oligomerization.

Secreted TRAIL

In one embodiment, a form of TRAIL that is secreted (secreted TRAIL or sol TRAIL) is expressed by the oncolytic virus described herein. Various forms of secreted TRAIL can be used in the methods and compositions described herein. In one embodiment, the secreted TRAIL is the naturally occurring soluble TRAIL. (Ashkenazi A. et al., J Clin Oncol 2008; 26: 3621-30, and Kelley S K et al., J Pharmacol Exp Ther 2001; 299: 31-8). In one embodiment the naturally occurring soluble TRAIL is fused with an antibody derivative, such as scFv245 (Bremer E. et al., J Mol Med 2008; 86: 909-24; Bremer E, et al., Cancer Res 2005; 65: 3380-88; Bremer E, et al., J Biol Chem 2005; 280: 10025-33, and Stieglmaier J, et al., Cancer Immunol Immunother 2008; 57: 233-46).

Alternatively, the endogenous secretion sequence of TRAIL present on the N terminus can be replaced with the signal sequence (otherwise referred to as the extracellular domain) from Flt3 ligand and an isoleucine zipper (Shah et al., Cancer Research 64: 3236-3242 (2004); WO 2012/106281; Shah et al. Mol Ther. 2005 June; 11(6):926-31). Other secretion signal sequences can be added to TRAIL in turn to generate a secreted TRAIL for use in the invention. For example, SEC2 signal sequence and SEC(CV) signal sequence can be fused to TRAIL (see for example U.S. Patent Publication 2002/0128438). Other secretion signal sequences may also be used and nucleotides including restriction enzyme sites can be added to the 5' or 3' terminal of respective secretion signal sequence, to facilitate the incorporation of such sequences into the DNA cassette. Such secretion signal sequences can be fused to the N-terminus or to the C-terminus.

Additionally, a linker sequence may be inserted between heterologous sequence and the TRAIL in order to preserve function of either portion of the generated fusion protein. Such linker sequences known in the art include a linker domain having the 7 amino acids (EASGGPE; SEQ ID NO: 3), a linker domain having 18 amino acids (GSTGGSGK-PGSGEGSTGG; SEQ ID NO: 4). As used herein, a "linker sequence" refers to a peptide, or a nucleotide sequence encoding such a peptide, of at least 8 amino acids in length. In some embodiments of the aspects described herein, the linker module comprises at least 9 amino acids, at least 10 amino acids, at least 11 amino acids, at least 12 amino acids, at least 13 amino acids, at least 14 amino acids, at least 15 amino acids, at least 16 amino acids, at least 17 amino acids, at least 18 amino acids, at least 19 amino acids, at least 20 amino acids, at least 21 amino acids, at least 22 amino acids, at least 23 amino acids, at least 24 amino acids, at least 25 amino acids, at least 30 amino acids, at least 35 amino acids, at least 40 amino acids, at least 45 amino acids, at least 50 amino acids, at least 55 amino acids, at least 56 amino acids, at least 60 amino acids, or least 65 amino acids. In some embodiments of the aspects described herein, a linker module comprises a peptide of 18 amino acids in length. In some embodiments of the aspects described herein, a linker module comprises a peptide of at least 8 amino acids in length but less than or equal to 56 amino acids in length, i.e., the length of the spacer sequence in the native TRAIL molecule of SEQ ID NO: 1. In some embodiments, the linker sequence comprises the spacer sequence of human TRAIL, i.e., amino acids 39-94 of SEQ ID NO: 1, or a sequence having at least 80%, at least 85%, at least 90%, at least 95%, at least 99% identity to amino acids 39-94 of SEQ ID NO: 1.

Signal Sequences

Secreted TRAIL may be generated by incorporation of a secretion signal sequence into the TRAIL or TRAIL fragment or derivative. As used herein, the terms "secretion signal sequence," "secretion sequence," "secretion signal peptide," or "signal sequence," refer to a sequence that is usually about 3-60 amino acids long and that directs the transport of a propeptide to the endoplasmic reticulum and through the secretory pathway during protein translation. As used herein, a signal sequence, which can also be known as a signal peptide, a leader sequence, a prepro sequence or a pre sequence, does not refer to a sequence that targets a protein to the nucleus or other organelles, such as mitochondria, chloroplasts and apicoplasts. In one embodiment, the secretion signal sequence comprises 5 to 15 amino acids with hydrophobic side chains that are recognized by a cytosolic protein, SRP (Signal Recognition Particle), which stops translation and aids in the transport of an mRNA-ribosome complex to a translocon in the membrane of the endoplasmic reticulum. In one embodiment, the secretion signal peptide comprises at least three regions: an amino-terminal polar region (N region), where frequently positive charged amino acid residues are observed, a central hydrophobic region (H region) of 7-8 amino acid residues and a carboxy-terminal region (C region) that includes the cleavage site. Commonly, the signal peptide is cleaved from the mature protein with cleavage occurring at this cleavage site.

The secretory signal sequence is operably linked to the TRAIL or TRAIL fragment or derivative such that the two sequences are joined in the correct reading frame and positioned to direct the newly synthesized polypeptide into the secretory pathway of the host cell. Secretory signal sequences are commonly positioned 5' to the nucleotide sequence encoding the polypeptide of interest, although certain secretory signal sequences can be positioned elsewhere in the nucleotide sequence of interest (see, e.g., Welch et al., U.S. Pat. No. 5,037,743; Holland et al., U.S. Pat. No. 5,143,830).

In one embodiment, the secretory sequence comprises amino acids 1-81 of the following Flt3L amino acid sequence: MTVLAPAWSP NSSLLLLLLL LSPCLRGTPD CYFSHSPISS NFKVKFRELT DHLLKDYPVT VAVNLQDEKH CKALWSLFLA QRWIEQLKTV AGSKMQTLLE DVNTEIHFVT SCTFQPLPEC LRFVQTNISH LLKDTCTQLL ALKPCIGKAC QNFSRCLEVQ CQPDSSTLLP PRSPIALEAT ELPEPRPRQL LLLLLLLPL TLVLLAAAWG LRWQRARRRG ELHPGVPLPS HP (SEQ ID NO: 2, GenBank Accession P49772), or a functional fragment thereof. In one embodiment, the signal peptide comprises amino acids 1-81 of SEQ ID NO: 2. In one embodiment, the secretory signal sequence comprises a sequence having at least 90% identity to amino acids 1-81 of SEQ ID NO: 2. In one embodiment, the secretory signal sequence consists essentially of amino acids 1-81 of SEQ ID NO: 2. In one embodiment, the secretory signal sequence consists of amino acids 1-81 of SEQ ID NO: 2.

While the secretory signal sequence can be derived from Flt3L, in other embodiments a suitable signal sequence can also be derived from another secreted protein or synthesized de novo. Other secretory signal sequences which can be substituted for the Flt3L signal sequence for expression in eukaryotic cells include, for example, naturally-occurring or modified versions of the human IL-17RC signal sequence, otPA pre-pro signal sequence, human growth hormone signal sequence, human CD33 signal sequence Ecdysteroid Glucosyltransferase (EGT) signal sequence, honey bee Melittin (Invitrogen Corporation; Carlsbad, Calif.), baculovirus gp67 (PharMingen: San Diego, Calif.) (US Pub. No. 20110014656). Additional secretory sequences include secreted alkaline phosphatase signal sequence, interleukin-1 signal sequence, CD-14 signal sequence and variants thereof (US Pub. No. 20100305002) as well as the following peptides and derivatives thereof: Sandfly Yellow related protein signal peptide, silkworm friboin LC signal peptide, snake PLA2, *Cyrpidina noctiluca* luciferase signal peptide, and pinemoth fibroin LC signal peptide (US Pub. No. 20100240097). Further signal sequences can be selected from databases of protein domains, such as SPdb, a signal peptide database described in Choo et al., BMC Bioinformatics 2005, 6:249, LOCATE, a mammalian protein localization database described in Sprenger et al. Nuc Acids Res, 2008, 36:D230D233, or identified using computer modeling by those skilled in the art (Ladunga, Curr Opin Biotech 2000, 1:13-18).

Selection of appropriate signal sequences and optimization or engineering of signal sequences is known to those skilled in the art (Stern et al., Trends in Cell & Molecular Biology 2007 2:1-17; Barash et al., Biochem Biophys Res Comm 2002, 294:835-842). In one embodiment, a signal sequence can be used that comprise a protease cleavage site for a site-specific protease (e.g., Factor IX or Enterokinase). This cleavage site can be included between the pro sequence and the bioactive secreted peptide sequence, e.g., TRAIL domain, and the pro-peptide can be activated by the treatment of cells with the site-specific protease (US Pub. No. 20100305002).

Leucine Zippers

The TRAIL or TRAIL fragment, derivative or variant, described herein can, in some embodiments, further comprise a leucine zipper domain sequence. As used herein, "leucine zipper domains" refer to naturally occurring or synthetic peptides that promote oligomerization of the proteins in which they are found. The leucine zipper is a super-secondary structure that functions as a dimerization domain, and its presence generates adhesion forces in parallel alpha helices. A single leucine zipper comprises multiple leucine residues at approximately 7-residue intervals, which forms an amphipathic alpha helix with a hydrophobic region running along one side. The dimer formed by a zipper domain is stabilized by the heptan repeat, designated (abcdefg)$_n$ according to the notation of McLachlan and Stewart (J. Mol. Biol. 98:293; 1975), in which residues a and d are generally hydrophobic residues, with d being a leucine, which line up on the same face of a helix. Oppositely-charged residues commonly occur at positions g and e. Thus, in a parallel coiled coil formed from two helical zipper domains, the "knobs" formed by the hydrophobic side chains of the first helix are packed into the "holes" formed between the side chains of the second helix. The residues at position d (often leucine) contribute large hydrophobic stabilization energies, and are important for oligomer formation (Krystek et al., Int. J. Peptide Res. 38:229, 1991). This hydrophobic region provides an area for dimerization, allowing the motifs to "zip" together. Furthermore, the hydrophobic leucine region is absolutely required for DNA binding. Leucine zippers were originally identified in several DNA-binding proteins (Landschulz et al., Science 240: 1759, 1988), and have since been found in a variety of different proteins. Among the known leucine zippers are naturally occurring peptides and derivatives thereof that dimerize or trimerize.

Examples of zipper domains are those found in the yeast transcription factor GCN4 and a heat-stable DNA-binding protein found in rat liver (C/EBP; Landschulz et al., Science 243:1681, 1989). The nuclear transforming proteins, fos and jun, also exhibit zipper domains, as does the gene product of the murine proto-oncogene, c-myc (Landschulz et al., Science 240:1759, 1988). The fusogenic proteins of several different viruses, including paramyxovirus, coronavirus, measles virus and many retroviruses, also possess zipper domains (Buckland and Wild, Nature 338:547, 1989; Britton, Nature 353:394, 1991; Delwart and Mosialos, AIDS Research and Human Retrovirtises 6:703, 1990). The zipper domains in these fusogenic viral proteins are near the transmembrane region of the protein. Oligomerization of fusogenic viral proteins is involved in fusion pore formation (Spruce et al, Proc. Natl. Acad. Sci. U.S.A. 88:3523, 1991). Zipper domains have also been reported to play a role in oligomerization of heat-shock transcription factors (Rabindran et al., Science 259:230, 1993).

Examples of leucine zipper domains suitable for producing multimodal TRAIL agents include, but are not limited to, those described in PCT application WO 94/10308; U.S. Pat. No. 5,716,805; the leucine zipper derived from lung surfactant protein D (SPD) described in Hoppe et al., 1994, FEBS Letters 344:191; and Fanslow et al., 1994, Semin. Immunol. 6:267-278, the contents of each of which are hereby incorporated by reference in their entireties. In one embodiment, leucine residues in a leucine zipper domain are replaced by isoleucine residues. Such peptides comprising isoleucine can also be referred to as isoleucine zippers, but are encompassed by the term "leucine zippers" as used herein.

Additional Nucleic Acids

The recombinant oncolytic virus comprising TRAIL nucleic acid may further contain additional heterologous nucleic acid sequences (e.g., in expressible form), referred to herein as a second heterologous nucleic acid sequence, a third heterologous nucleic acid sequence, etc. Alternatively, the recombinant oncolytic virus may contain no additional heterologous nucleic acid sequences.

Any desired DNA can be inserted, including DNA that encodes selectable markers, or preferably genes coding for a therapeutic, biologically active protein, such as interferons, cytokines, chemokines, or more preferably DNA coding for a prodrug converting enzyme, including thymidine kinase (Martuza et al., Science, 252:854, 1991), cytosine deamindase (U.S. Pat. No. 5,358,866), cyp450 (U.S. Pat. No. 5,688,773), and others. In one embodiment, the nucleic acid encodes a protein that inhibits tumor growth (e.g., a chemotherapeutic, growth regulatory agent) or modifies an immune response. An example of a chemotherapeutic agent is mitomicin C. In one embodiment, the nucleic acid encodes a growth regulatory molecule (e.g., one that has been lost in tumorigenesis of the tumor). Examples of such molecules without limitation proteins from the caspase family such as Caspase-9 (P55211(CASP9_HUMAN); HGNC: 15111; Entrez Gene: 8422; Ensembl: ENSG000001329067; OMIM: 6022345; UniProtKB: P552113), Caspase-8 (Q14790 (CASP8_HUMAN); 9606 [NCBI]), Caspase-7 (P55210 (CASP7_HUMAN); 9606 [NCBI]), and Caspase-3 (HCGN: 1504; Ensembl: ENSG00000164305; HPRD:02799; MIM:600636; Vega: OTTHUMG00000133681), pro-apoptotic proteins such as Bax (HGNC: 9591; Entrez Gene: 5812; Ensembl: ENSG000000870887; OMIM: 6000405; UniProtKB: Q078123), Bid (HGNC: 10501; Entrez Gene: 6372; Ensembl: ENSG000000154757; OMIM: 6019975; UniProtKB: P559573), Bad (HGNC: 9361; Entrez Gene: 5722; Ensembl: ENSG000000023307; OMIM: 6031675; UniProtKB: Q92934), Bak (HGNC: 9491; Entrez Gene: 5782; Ensembl: ENSG000000301107; OMIM: 6005165; UniProtKB: Q166113), BCL2L11 (HGNC: 9941; Entrez Gene: 100182; Ensembl: ENSG000001530947; OMIM: 6038275; UniProtKB: 0435213), p53 (HGNC: 119981; Entrez Gene: 71572; Ensembl: ENSG000001415107; OMIM: 1911705; UniProtKB: P046373), PUMA (HGNC: 178681; Entrez Gene: 271132; Ensembl: ENSG000001053277; OMIM: 6058545; UniProtKB: Q96PG83; UniProtKB: Q9BXH13), Diablo/SMAC (HGNC: 215281; Entrez Gene: 566162; Ensembl: ENSG000001840477; OMIM: 6052195; UniProtKB: Q9NR283). In one embodiment, the nucleic acid encodes an immunomodulatory agent (e.g, immunostimulatory transgenes), including, without limitation, Flt-3 ligand, HMBG1, calreticulin, GITR ligand, interleukin-12, interleukin-15, interleukin-18, or CCL17.

The exogenous nucleic acids can be inserted into the oncolytic virus by the skilled practitioner. In one embodiment, the oncolytic virus is HSV and the exogenous nucleic acid is inserted into the thymidine kinase (TK) gene of the viral genome, or replacing the deleted TK gene (see for example, U.S. Pat. No. 5,288,641 for insertion of exogenous nucleic acid into HSV). When the oncolytic virus comprises a second exogenous nucleic acid, the nucleic acid preferably encodes an anti-oncogenic or oncolytic gene product. The gene product may be one (e.g. an antisense oligonucleotide) which inhibits growth or replication of only the cell infected by the virus, or it may be one (e.g. thymidine kinase) which exerts a significant bystander effect upon lysis of the cell infected by the virus.

Methods of Treatment

Another aspect of the invention relates to a method of treating a proliferative disorder in a subject. The method comprises administering a recombinant oncolytic virus comprising the TRAIL nucleic acid sequences (herein referred to as recombinant oncolytic virus-TRAIL) described herein to the subject to thereby contact cells exhibiting undesired proliferation with an effective amount of the recombinant oncolytic virus-TRAIL. In one embodiment, the subject is diagnosed with a tumor that is resistant to an oncolytic virus (e.g, oHSV), to TRAIL or secreted TRAIL, or a combination thereof.

In one embodiment, the proliferative disorder is a tumor and the method of the invention relates to a method for inhibiting tumor progression. An effective amount of the recombinant oncolytic virus-TRAIL is contacted to the tumor to thereby deliver the molecule to the tumor cells.

The term "tumor" refers to the tissue mass or tissue type or cell type that is undergoing uncontrolled proliferation. A tumor can be benign or malignant. A benign tumor is characterized as not undergoing metastasis. A malignant cell is a cancer cell and can undergo metastasis. Tumors on which the method can be performed include, without limitation, adenoma, angio-sarcoma, astrocytoma, epithelial carcinoma, germinoma, glioblastoma, glioma, hamartoma, hemangioendothelioma, hemangiosarcoma, hematoma, hepato-blastoma, leukemia, lymphoma, medulloblastoma, melanoma, neuroblastoma, osteosarcoma, retinoblastoma, rhabdomyosarcoma, sarcoma, and teratoma. The tumor can be chosen from acral lentiginous melanoma, actinic keratoses, adenocarcinoma, adenoid cycstic carcinoma, adenomas, adenosarcoma, adenosquamous carcinoma, astrocytic tumors, bartholin gland carcinoma, basal cell carcinoma, bronchial gland carcinomas, capillary, carcinoids, carcinoma, carcinosarcoma, cavernous, cholangio-carcinoma, chondosarcoma, choriod plexus papilloma/carcinoma, clear cell carcinoma, cystadenoma, endodermal sinus tumor, endometrial hyperplasia, endometrial stromal sarcoma, endometrioid adenocarcinoma, ependymal, epitheloid, Ewing's sarcoma, fibrolamellar, focal nodular hyperplasia, gastrinoma, germ cell tumors, glioblastoma, glucagonoma, hemangiblastomas, hemangioendothelioma, hemangiomas, hepatic adenoma, hepatic adenomatosis, hepatocellular carcinoma, insulinoma, intaepithelial neoplasia, interepithelial squamous cell neoplasia, invasive squamous cell carcinoma, large cell carcinoma, leiomyosarcoma, lentigo maligna melanomas, malignant melanoma, malignant mesothelial tumors, medulloblastoma, medulloepithelioma, melanoma, meningeal, mesothelial, metastatic carcinoma, mucoepidermoid carcinoma, neuroblastoma, neuroepithelial adenocarcinoma nodular melanoma, oat cell carcinoma, oligodendroglial, osteosarcoma, pancreatic, papillary serous adeno-carcinoma, pineal cell, pituitary tumors, plasmacytoma, pseudo-sarcoma, pulmonary blastoma, renal cell carcinoma, retinoblastoma, rhabdomyosarcoma, sarcoma, serous carcinoma, small cell carcinoma, soft tissue carcinomas, somatostatin-secreting tumor, squamous carcinoma, squamous cell carcinoma, submesothelial, superficial spreading melanoma, undifferentiated carcinoma, uveal melanoma, verrucous carcinoma, vipoma, well differentiated carcinoma, and Wilm's tumor. In one embodiment, the tumor expresses one or more receptors for TRAIL.

Another aspect of the invention relates to a method of treating a subject for a cell proliferative disorder such as cancer. The method comprises administering a therapeutically effective amount of recombinant oncolytic virus-TRAIL to the subject in the form of a pharmaceutical composition. Examples of cancer include but are not limited to, carcinoma, lymphoma, blastoma, sarcoma, and leukemia. More particular examples of such cancers include, but are not limited to, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma (GBM); hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

In one embodiment the cancer is a brain cancer, brain tumor, or intracranial neoplasm. Intracranial neoplasms or cancers can arise from any of the structures or cell types present in the CNS, including the brain, meninges, pituitary gland, skull, and even residual embryonic tissue. The overall annual incidence of primary brain tumors in the United States is 14 cases per 100,000. The most common primary brain tumors are meningiomas, representing 27% of all primary brain tumors, and glioblastomas, representing 23% of all primary brain tumors (whereas glioblastomas account for 40% of malignant brain tumor in adults). Many of these tumors are aggressive and of high grade. Primary brain tumors are the most common solid tumors in children and the second most frequent cause of cancer death after leukemia in children.

Pharmaceutical Compositions

The pharmaceutically acceptable vehicle for delivery of the recombinant oncolytic virus-TRAIL can be selected from known pharmaceutically acceptable vehicles, and should be one in which the virus is stable. For example, it can be a diluent, solvent, buffer, and/or preservative. An example of a pharmaceutically acceptable vehicle is phosphate buffer containing NaCl. Other pharmaceutically acceptable vehicles aqueous solutions, non-toxic excipients, including salts, preservatives, buffers and the like are described in REMINGTON'S PHARMACEUTICAL SCIENCES, 15th Ed. Easton: Mack Publishing Co. pp 1405-1412 and 1461-1487 (1975) and THE NATIONAL FORMULARY XIV., 14th Ed. Washington: American Pharmaceutical Association (1975), the contents of which are hereby incorporated by reference.

Pharmaceutical compositions and formulations for specified modes of administration, described herein are also encompassed by the present invention. In one embodiment, the oncolytic virus-TRAIL described herein is an active ingredient in a composition comprising a pharmaceutically acceptable carrier. Such a composition is referred to herein as a pharmaceutical composition. A "pharmaceutically acceptable carrier" means any pharmaceutically acceptable means to mix and/or deliver the targeted delivery composition to a subject. The term "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the composition and is compatible with administration to a subject, for example a human. Such compositions can be specifically formulated for administration via one or more of a number of routes, such as the routes of administration described herein. Supplementary active ingredients also can be incorporated into the compositions. When an agent, formulation or pharmaceutical composition described herein, is administered to a subject, preferably, a therapeutically effective amount is administered. As used herein, the term "therapeutically effective amount" refers to an amount that results in an improvement or remediation of the condition.

Administration

Administration of the pharmaceutical composition to a subject is by means which the recombinant oncolytic virus-TRAIL contained therein will contact the target cell. The specific route will depend upon certain variables such as the target cell, and can be determined by the skilled practitioner. Suitable methods of administering a composition comprising a pharmaceutical composition of the present invention to a patient include any route of in vivo administration that is suitable for delivering a viral vector, recombinant nucleic acid molecule or protein to a patient. The preferred routes of administration will be apparent to those of skill in the art, depending on the type of viral vector used, the target cell population, and the disease or condition experienced by the subject. Preferred methods of in vivo administration include, but are not limited to, intravenous administration, intraperitoneal administration, intramuscular administration, intracoronary administration, intraarterial administration (e.g., into a carotid artery), subcutaneous administration, transdermal delivery, intratracheal administration, subcutaneous administration, intraarticular administration, intraventricular administration, inhalation (e.g., aerosol), intracerebral, nasal, oral, pulmonary administration, impregnation of a catheter, and direct injection into a tissue. In an embodiment where the target cells are in or near a tumor, a preferred route of administration is by direct injection into the tumor or tissue surrounding the tumor. For example, when the tumor is a breast tumor, the preferred methods of administration include impregnation of a catheter, and direct injection into the tumor.

Intravenous, intraperitoneal, and intramuscular administrations can be performed using methods standard in the art. Aerosol (inhalation) delivery can also be performed using methods standard in the art (see, for example, Stribling et al., Proc. Natl. Acad. Sci. USA 189:11277-11281, 1992, which is incorporated herein by reference in its entirety). Oral delivery can be performed by complexing a therapeutic composition of the present invention to a carrier capable of withstanding degradation by digestive enzymes in the gut of an animal. Examples of such carriers, include plastic capsules or tablets, such as those known in the art.

One method of local administration is by direct injection. Direct injection techniques are particularly useful for administering a recombinant nucleic acid molecule to a cell or tissue that is accessible by surgery, and particularly, on or near the surface of the body. Administration of a composition locally within the area of a target cell refers to injecting the composition centimeters and preferably, millimeters from the target cell or tissue.

Dosage and Treatment Regimen

The appropriate dosage and treatment regimen for the methods of treatment described herein will vary with respect to the particular disease being treated, the molecules being delivered, and the specific condition of the subject. The skilled practitioner is to determine the amounts and frequency of administration on a case by case basis. In one embodiment, the administration is over a period of time until the desired effect (e.g., reduction in symptoms is achieved). In one embodiment, administration is 1, 2, 3, 4, 5, 6, or 7 times per week. In one embodiment, administration is over a period of 1, 2, 3, 4, 5, 6, 7, 8, 9, or 10 weeks. In one embodiment, administration is over a period of 2, 3, 4, 5, 6 or more months. In one embodiment, treatment is resumed following a period of remission.

Kits

Another aspect of the invention relates to a kit comprising one or more of the compositions described herein. Optionally the kit can include the compositions distributed in single or multiple dosages units. The kit may comprise the composition packaged in a device for administration. The kit may optionally comprise directions for use, dosage, and/or administration of the composition contained within.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to described the present invention, in connection with percentages means±1%.

In one respect, the present invention relates to the herein described compositions, methods, and respective component(s) thereof, as essential to the invention, yet open to the inclusion of unspecified elements, essential or not ("comprising). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The present invention may be as defined in any one of the following numbered paragraphs.

1. A recombinant oncolytic virus comprising a nucleic acid sequence encoding tumor necrosis factor-related apoptosis-inducing ligand (TRAIL) or a biologically active fragment thereof, in expressible form.
2. The recombinant oncolytic virus of paragraph 1, wherein the oncolytic virus is an oncolytic herpes simplex virus (oHSV).

3. The recombinant oncolytic virus of paragraph 2, wherein the oHSV is selected from the group consisting of G207, G47Δ HSV-R3616, 1716, R3616, and R4009.
4. The recombinant oncolytic virus of any one of paragraphs 1-3, wherein the TRAIL is a secreted form of TRAIL (S-TRAIL).
5. The recombinant oncolytic virus of any one of paragraphs 1-3, wherein the TRAIL is a TRAIL fusion protein.
6. The recombinant oncolytic virus of any one of paragraphs 2-5, wherein the TRAIL is regulated by the HSV immediate early 4/5 promoter.
7. The recombinant oncolytic virus of any one of paragraphs 1-6, wherein the virus contains an additional exogenous nucleic acid in expressible form.
8. The recombinant oncolytic virus of any one of paragraphs 1-6 wherein the virus contains no additional exogenous nucleic acids.
9. A nucleic acid comprising the genome of a recombinant oncolytic virus of any one of paragraphs 1-8.
10. A host cell comprising an oncolytic virus of any one of paragraphs 1-8 or the nucleic acid of paragraph 9.
11. The nucleic acid of paragraph 9 that is selected from the group consisting of a bacterial artificial chromosome (BAC), a P1-derived artificial chromosome (PAC), a yeast artificial chromosome (YAC) and a human artificial chromosome (HAC).
12. A pharmaceutical composition comprising a recombinant oncolytic virus of any one of paragraphs 1-8.
13. A kit comprising the pharmaceutical composition of paragraph 12 and instructions for use.
14. A method of inhibiting tumor progression in a subject comprising contacting the tumor with an effective amount of a recombinant oncolytic virus of any one of paragraphs 1-8.
15. The method of paragraph 14, wherein the tumor is a brain tumor.
16. The method of paragraph 15, wherein the brain tumor is a glioma.
17. The method of paragraph 14, wherein the tumor is malignant.
18. The method of paragraph 17, wherein the tumor is selected from the group consisting of adenoma, angiosarcoma, astrocytoma, epithelial carcinoma, germinoma, glioblastoma, glioma, hamartoma, hemangioendothelioma, hemangiosarcoma, hematoma, hepato-blastoma, leukemia, lymphoma, medulloblastoma, melanoma, neuroblastoma, osteosarcoma, retinoblastoma, rhabdomyosarcoma, sarcoma, and teratoma. The tumor can be chosen from acral lentiginous melanoma, actinic keratoses, adenocarcinoma, adenoid cycstic carcinoma, adenomas, adenosarcoma, adenosquamous carcinoma, astrocytic tumors, bartholin gland carcinoma, basal cell carcinoma, bronchial gland carcinomas, capillary, carcinoids, carcinoma, carcinosarcoma, cavernous, cholangio-carcinoma, chondosarcoma, choriod plexus papilloma/carcinoma, clear cell carcinoma, cystadenoma, endodermal sinus tumor, endometrial hyperplasia, endometrial stromal sarcoma, endometrioid adenocarcinoma, ependymal, epitheloid, Ewing's sarcoma, fibrolamellar, focal nodular hyperplasia, gastrinoma, germ cell tumors, glioblastoma, glucagonoma, hemangiblastomas, hemangioendothelioma, hemangiomas, hepatic adenoma, hepatic adenomatosis, hepatocellular carcinoma, insulinoma, intaepithelial neoplasia, interepithelial squamous cell neoplasia, invasive squamous cell carcinoma, large cell carcinoma, leiomyosarcoma, lentigo maligna melanomas, malignant melanoma, malignant mesothelial tumors, medulloblastoma, medulloepithelioma, melanoma, meningeal, mesothelial, metastatic carcinoma, mucoepidermoid carcinoma, neuroblastoma, neuroepithelial adenocarcinoma nodular melanoma, oat cell carcinoma, oligodendroglial, osteosarcoma, pancreatic, papillary serous adeno-carcinoma, pineal cell, pituitary tumors, plasmacytoma, pseudo-sarcoma, pulmonary blastoma, renal cell carcinoma, retinoblastoma, rhabdomyosarcoma, sarcoma, serous carcinoma, small cell carcinoma, soft tissue carcinomas, somatostatin-secreting tumor, squamous carcinoma, squamous cell carcinoma, submesothelial, superficial spreading melanoma, undifferentiated carcinoma, uveal melanoma, verrucous carcinoma, vipoma, well differentiated carcinoma, and Wilm's tumor.
19. The method of any one of paragraphs 14-18, wherein contacting is by a method of administration to the subject is by a method selected from the group consisting of intravenous administration, intraperitoneal administration, intramuscular administration, intracoronary administration, intraarterial administration, subcutaneous administration, transdermal delivery, intratracheal administration, subcutaneous administration, intraarticular administration, intraventricular administration, inhalation, intracerebral, nasal, oral, pulmonary administration, impregnation of a catheter, and direct injection into a tissue or tumor.
20. A method of treating cancer in a subject comprising administering to the subject a therapeutically effective amount of the pharmaceutical composition of paragraph 12, to thereby treat the cancer.
21. The method of paragraph 20, wherein the cancer is selected from the group consisting of basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma (GBM); hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema, and Meigs' syndrome.

22. The method of any one of paragraphs 20-21, wherein the cancer is brain cancer.
23. The method of paragraph 22, wherein the brain cancer is glioma or glioblastoma.
24. The method of any one of paragraphs 20-23, wherein administration is by a method selected from the group consisting of intravenous administration, intraperitoneal administration, intramuscular administration, intracoronary administration, intraarterial administration, subcutaneous administration, transdermal delivery, intratracheal administration, subcutaneous administration, intraarticular administration, intraventricular administration, inhalation, intracerebral, nasal, oral, pulmonary administration, impregnation of a catheter, and direct injection into a tissue or tumor.

The invention is further illustrated by the following examples, which should not be construed as further limiting.

EXAMPLES

In this study, a panel of established and patient derived primary GBM stem cell lines were screened for their sensitivity to a recombinant version of G47Δ (referred to herein as oHSV) and TRAIL. In an effort to develop anti-GBM therapies that target a broad spectrum of GBMs that are either resistant to TRAIL-mediated apoptosis or resistant to both oHSV-mediated oncolysis and TRAIL, oHSV-bearing secretable-TRAIL (oHSV-TRAIL) was engineered and a mechanism-based therapeutic approach to target resistant GBMs in vitro and in malignant and invasive GBM models in mice was extensively studied.

Results

Screening of different GBM lines reveals differential sensitivities to oHSV mediated oncolysis and S-TRAIL-mediated apoptosis. We screened a cohort of both established GBM cell lines (Gli36, U87, U251, and LN229) and primary glioma stem cell (GSC) lines obtained from surgical specimens (GBM4, GBM6, BT74, and GBM8F) for their sensitivity to purified S-TRAIL- or oHSV-mediated cell death. While three established lines had varying sensitivity to TRAIL-induced apoptosis-mediated by caspase-3 and -7, one established line (LN229) was fully resistant to TRAIL-mediated apoptosis. Among the primary GSC, GBM8F was fully resistant to TRAIL whereas other GSC lines had varying sensitivity to TRAIL-induced apoptosis. Next, we evaluated the sensitivity of established GBM lines and GSC lines to oHSV (G47Δ empty) mediated oncolysis. Among the established lines, TRAIL resistant LN229 line was also resistant to oHSV-mediated oncolysis whereas all the GSC lines were sensitive to oHSV-mediated oncolysis. The amounts of virus released by the oHSV-infected cells greatly varied among the GBM cell lines tested, and did not necessarily correspond to the sensitivity to oHSV-mediated oncolysis. These results reveal the identification of GBM lines that are either resistant to TRAIL-mediated apoptosis (LN229, GBM8F) or resistant to both oHSV-mediated oncolysis and TRAIL (LN229). Based on these results, we used LN229 and GBM8F GSC for further therapeutic evaluation (FIG. 1a).

To evaluate oHSV replication and spread in oHSV and TRAIL resistant GBM cells and corresponding changes in cell viability, LN229 and GBM8F cells engineered to express Renilla luciferase (Rluc)-mCherry (LN229-RmC, GBM8F-RmC) were infected with oHSV-bearing firefly luciferase (oHSV-Fluc, FIG. 8), and monitored by in vitro and in vivo dual bioluminescence imaging. In vitro, oHSV-Fluc replicates in both LN229 and GBM8F cells as indicated by firefly luciferase (Fluc) expression, but oHSV replication was more robust and peaked earlier in GBM8F cells than LN229 cells (FIG. 1B and FIG. 9). Accordingly, while oHSV killed GBM8F cells efficiently (indicated by Rluc expression), LN229 cells exhibited apparent resistance to the killing effect by oHSV (FIG. 1C). In vivo monitoring of virus infection demonstrated the ability of intratumorally injected oHSV-Fluc to replicate in intracerebral tumors generated with these GBM cells, and revealed patterns of virus replication similar to the ones observed in vitro (FIGS. 1B and D). These data reveal that although oHSV replicates in both oHSV resistant and sensitive lines but results in killing only the sensitive GBM8F line and suggest that GBMs might be heterogeneous in the responses to oHSV.

Figure 2A:
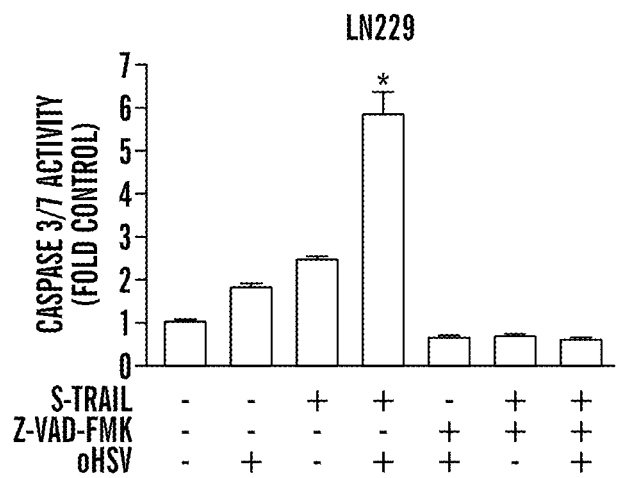
FIGS. 2A-2F contain graphical representations of experimental results that indicate Combination of oncolytic herpes simplex virus (oHSV) and S-TRAIL leads to caspase-3/7-mediated apoptosis in resistant glioblastoma multiforme (GBM) cells.
Figure 2B:
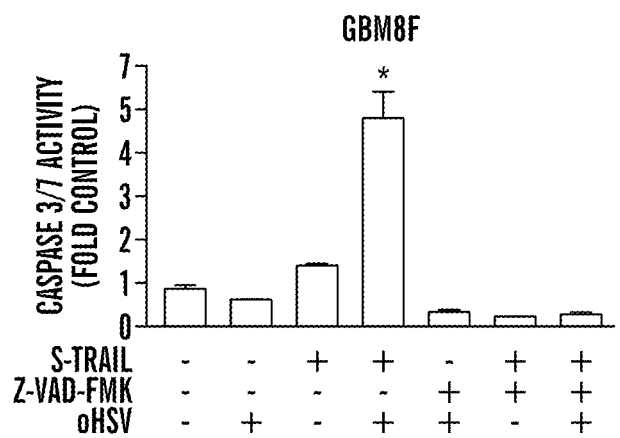
Figure 2C:
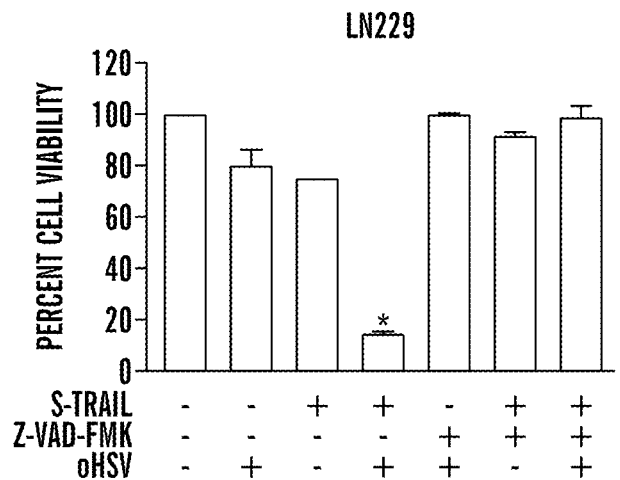
Figure 2D:
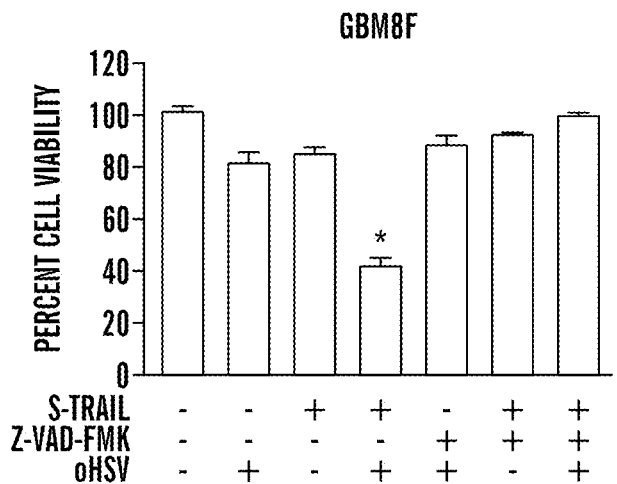
Figure 2E:
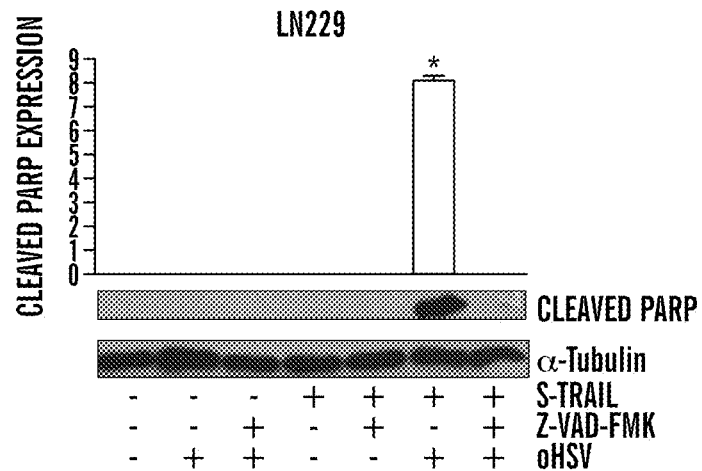
Figure 2F:
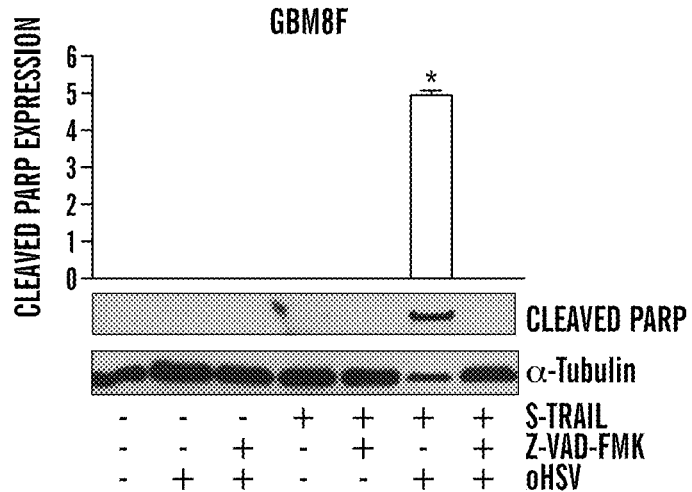
Figure 3A:
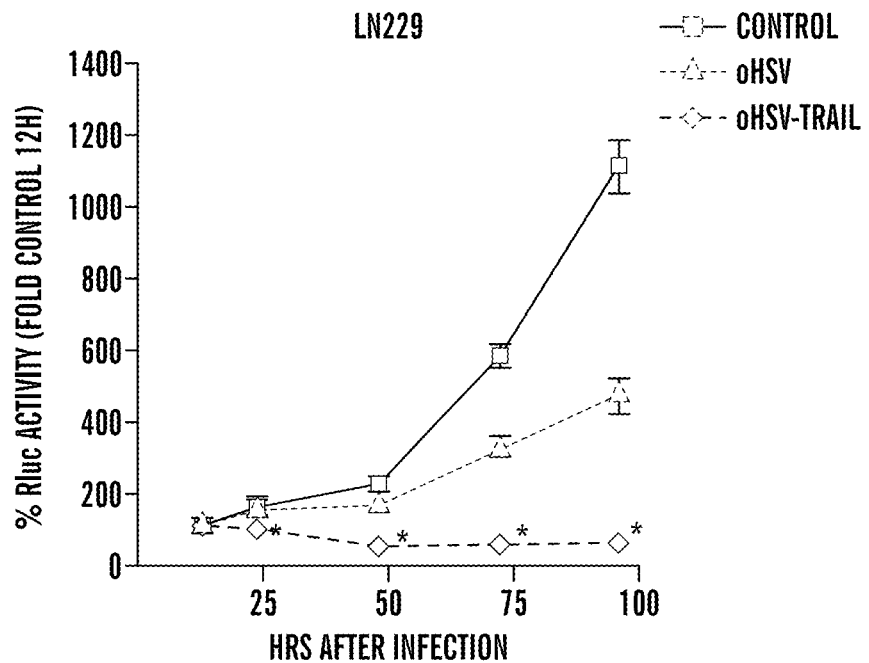
FIGS. 3A-3C contain graphical representations of experimental results that indicate Oncolytic herpes simplex virus (oHSV)-tumor necrosis factor-related apoptosis-inducing ligand (TRAIL) mediates potent cytotoxicity in resistant glioblastoma multiforme (GBM) cells by altering both cell proliferation and death pathways in vitro.
Figure 3B:
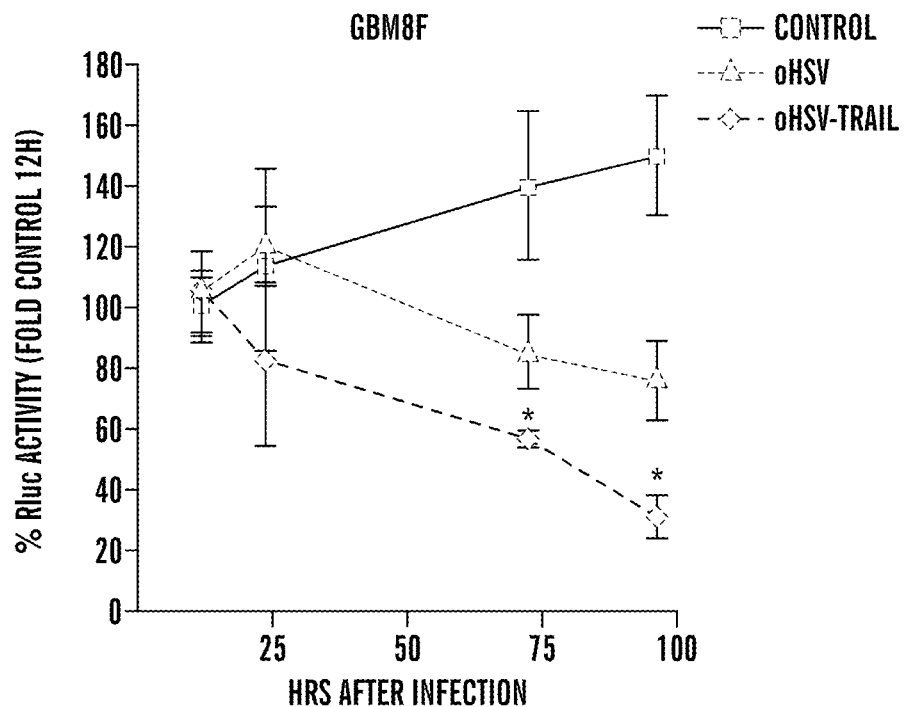
Figure 8:
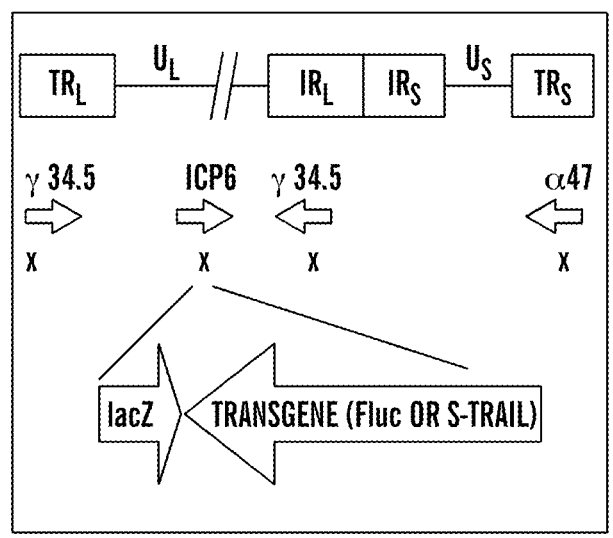
FIG. 8 is a schematic of oHSV bearing Fluc or S-TRAIL transgene. The HSV-1 genome consists of long and short unique regions (UL and Us) each bounded by terminal (T) and internal (I) repeat regions ($R_L$ and $R_S$). G47Δ-TRAIL (oHSV-TRAIL), and G47Δ-Fluc (oHSV-Fluc) were generated from G47ΔBAC, which is derived from the third-generation oncolytic HSV-1 (G47Δ) with triple mutations (γ34.5, ICP6, α47). The transgene Fluc or S-TRAIL as well as lacZ are located in the ICP6 locus in respective recombinants.
Figure 9B:
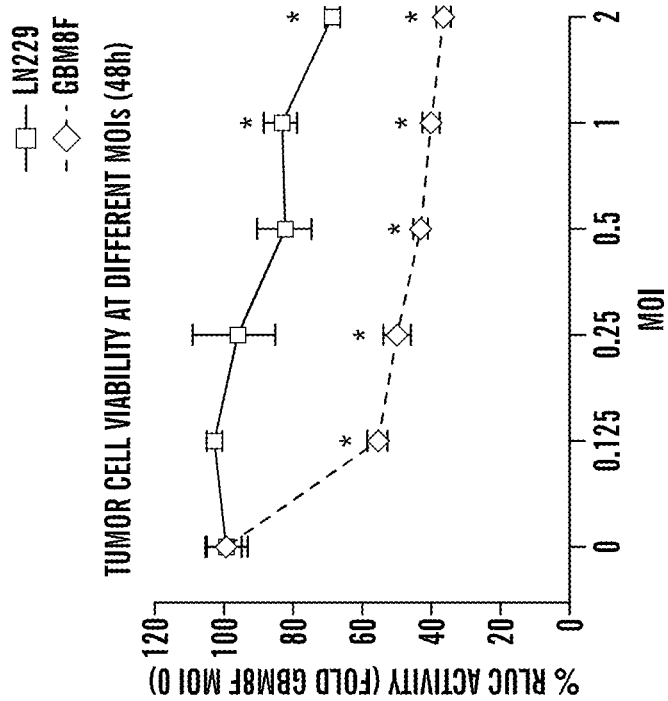
FIGS. 9A-9B contain graphs of experimental results that indicate Pharmacodynamics of oHSV in vitro at different MOIs.
Figure 9A:
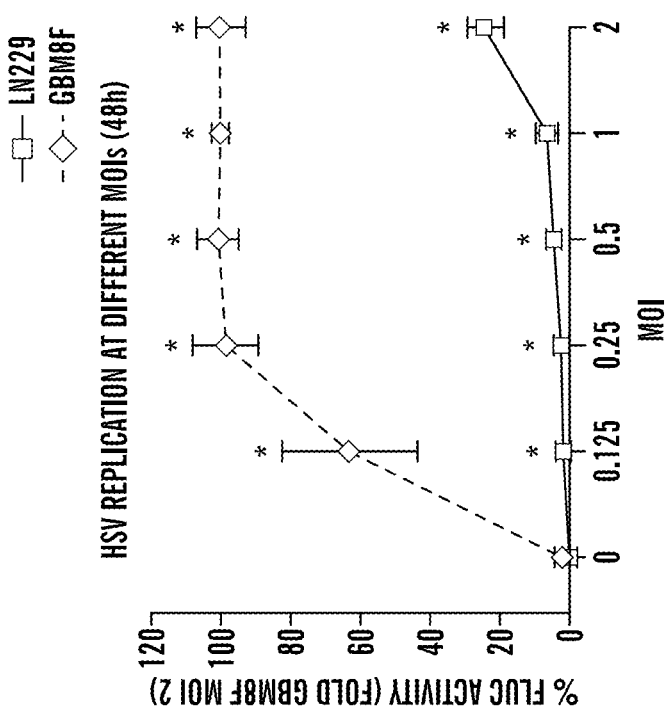
Figure 10E:
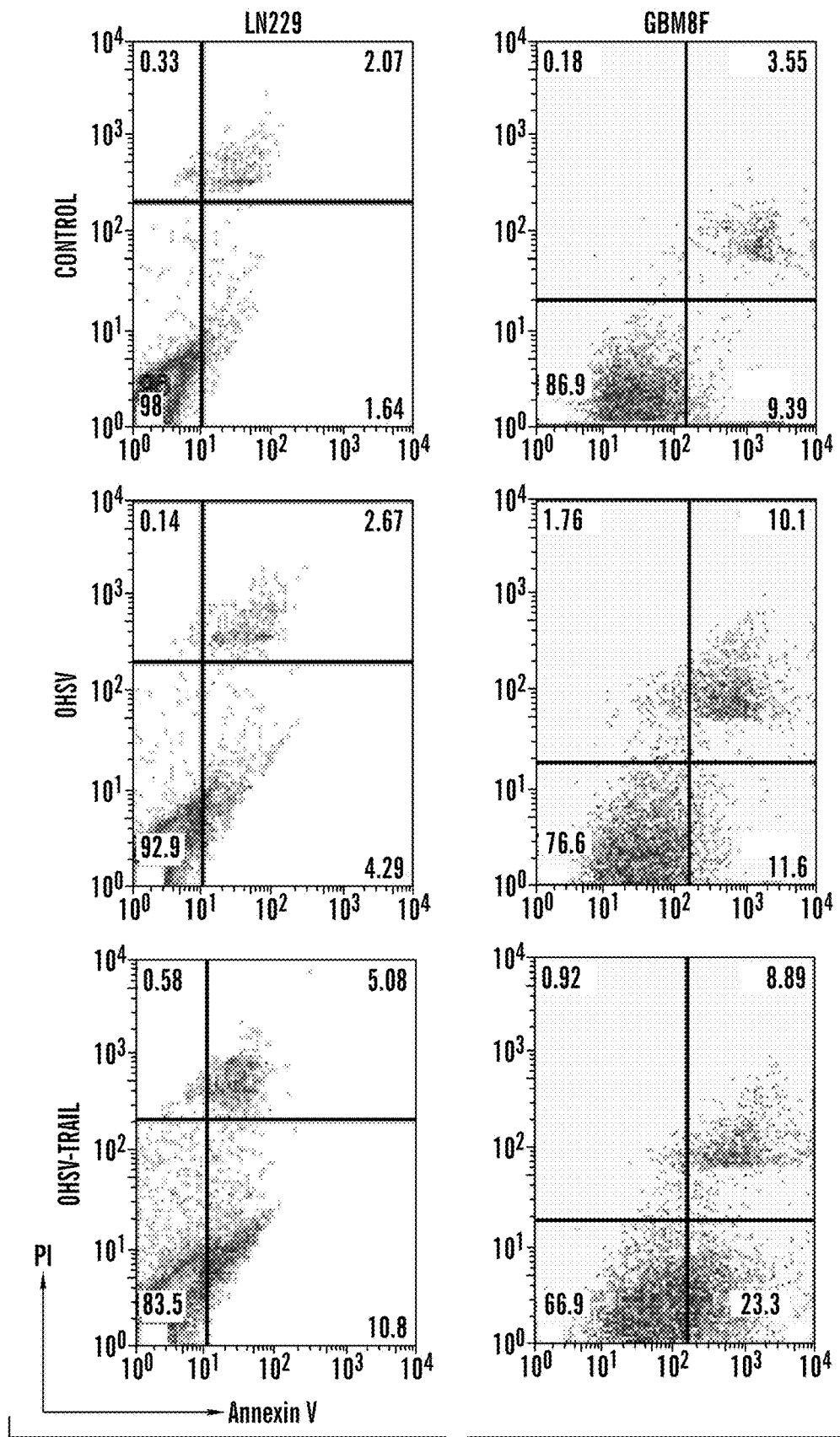
Figure 11:
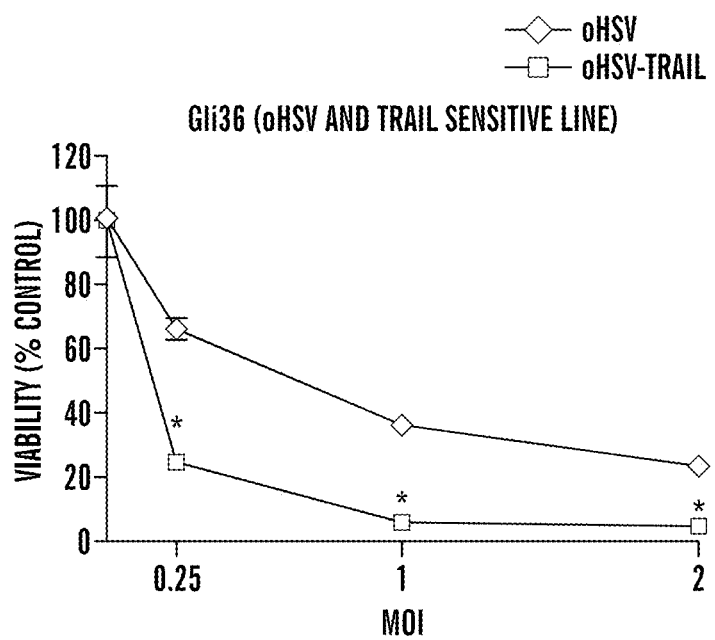
FIG. 11 is a graph of experimental results that indicate oHSV-TRAIL mediates potent cytotoxicity in sensitive GBM cells. Gli36 cells infected with oHSV or oHSV-TRAIL were assayed for viability at 48 hours post infection. Error bars indicate standard deviation. *, p<0.05
Figure 12:
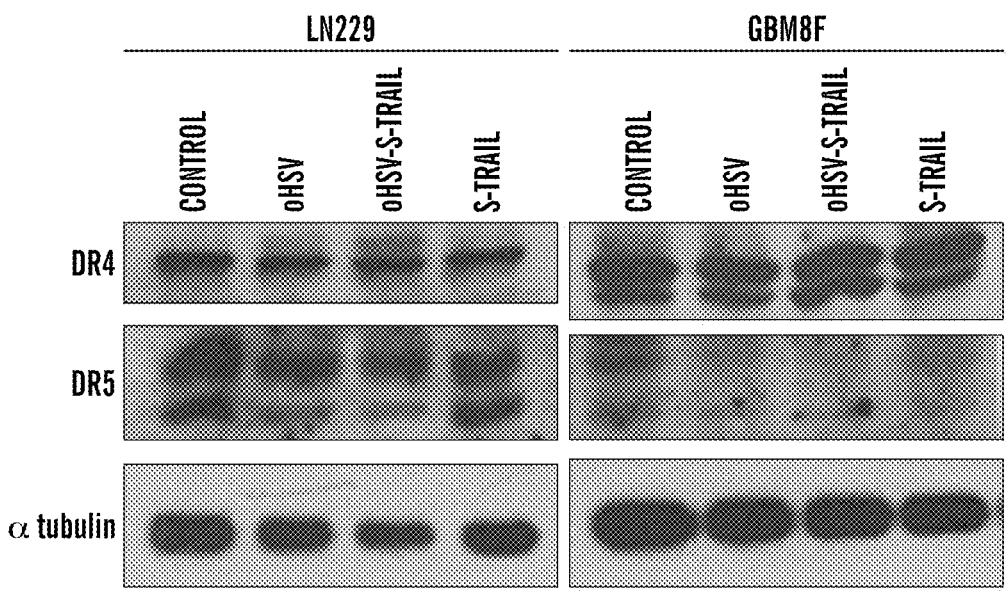
FIG. 12 contains photographs of experimental results that indicate oHSV TRAIL mediated potent cytotoxicity is independent of DR4/DR5 expression: Immunoblot analysis using antibodies against DR4 and DR5 on whole cell lysates prepared from LN229 and GBM8F cells untreated, or treated with oHSV, oHSV-TRAIL (MOI=1) or S-TRAIL for 18 hours. α-tubulin was used as a loading control.

Combination of oHSV and S-TRAIL Leads to Apoptosis in TRAIL Resistant GBM Cells In Vitro In order to evaluate the therapeutic potential of oHSV and S-TRAIL in resistant GBMs, established LN229 GBM cells and primary GBM8F (TRAIL resistant) GBM cells were infected with oHSV and treated with purified S-TRAIL 6 hours post-infection. oHSV infection and subsequent S-TRAIL treatment resulted in significant decrease in viability of LN229 and GBM8F cells in culture, which was associated with increased caspase-3/7 activation (FIGS. 2A-D). A significantly impaired activation of caspase-3/7 activity was observed when LN229 and GBM8F cells were infected with oHSV and treated with S-TRAIL in the presence of pan-caspase inhibitor, Z-VAD-FMK (FIGS. 2A, B). This resulted in complete reversal of both LN229 and GBM8F cell death in oHSV-infected and S-TRAIL-treated cells (FIGS. 2C-D). Western blotting revealed that cleavage of poly-ADP ribose polymerase (PARP), one of the main downstream targets of caspase-3, was undetectable by either S-TRAIL or oHSV treatment in both LN229 and GBM8F cells, indicating that oHSV-mediated cell death is primarily not dependent on caspase/PARP activation. However, cleaved PARP was increased in cells treated with combined oHSV and S-TRAIL (FIG. 2E, F). A significant reduction in PARP cleavage was observed when LN229 and GBM8F cells were infected with oHSV and treated with S-TRAIL in the presence of pan-caspase inhibitor, Z-VAD-FMK (FIG. 2E, F). These results revealed that oHSV and TRAIL combination leads to caspase-mediated apoptosis in TRAIL resistant and both TRAIL and oHSV resistant GBM cells.

oHSV-TRAIL Targets Both Cell Proliferation and Death Pathways in Resistant GBM Cells In order to target both TRAIL resistant and oHSV resistant cell lines, we engineered an oHSV-bearing S-TRAIL (oHSV-TRAIL) using a BAC containing the backbone structure of G47Δ, G47Δ-BAC[25,26,27] (FIG. 8). The replicating ability of oHSV-TRAIL was similar to that of oHSV as revealed by the virus yield quantified using plaque assay on Vero cells (FIG. 10A). The secretion of TRAIL in oHSV-TRAIL infected LN229 GBM cells was confirmed by ELISA (FIG. 10B). To evaluate the effect of oHSV-TRAIL, LN229-RmC cells and GBM8F-RmC cells were infected with oHSV or oHSV-TRAIL at multiplicity of infection (MOI)=1 for 24, 48, 72, and 96 hours. The changes in cell viability (Rluc activity) revealed that oHSV-TRAIL infection resulted in significantly more potent cell killing in both LN229 and GBM8F cells as compared to oHSV infection (FIGS. 3A and B and FIG. 10C, D). Annexin V staining analysis revealed that the number of apoptotic cells (Annexin V positive, propidium iodide negative) was considerably increased in both LN229 and GBM8F cell populations post-oHSV-TRAIL infection (FIG. 10E). oHSV-TRAIL also resulted in significantly greater killing in oHSV and TRAIL sensitive human Gli36 GBM line as compared to oHSV infection (FIG. 11). Western blot analysis of oHSV-TRAIL-infected LN229 and GBM8F cell lysates showed cleavage of caspases-8, -9 and PARP and no significant difference was observed in Bcl2 expression (FIG. 3C) and death receptor (DR)4/5 expression (FIG. 12). These results reveal that oHSV-TRAIL infection induces caspase-mediated apoptosis in both TRAIL resistant LN229 and GBM8F glioma lines.

Figure 3C:
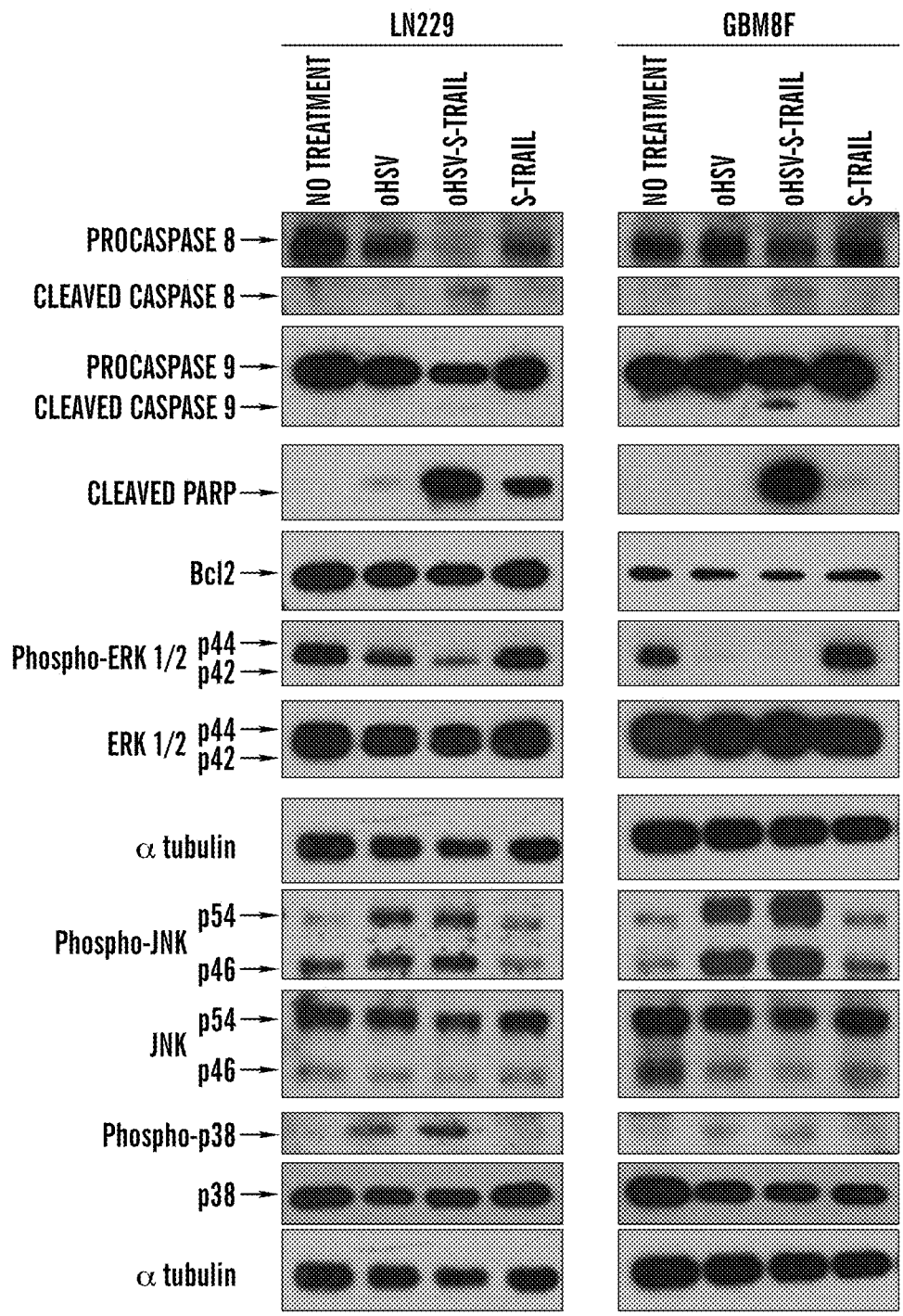

We next examined the mechanism of oHSV-TRAIL induced apoptosis in resistant GBM cells. As such, we assessed the activation of molecules involved in the cell proliferation pathways, mitogen-activated protein kinases (MAPKs) including extracellular signal-regulated protein kinase 1 and 2 (ERK 1/2), c-Jun N-terminal kinase (JNK) and p38 in both LN229 and GBM8F. A significantly impaired activation of ERK 1/2 was observed in LN229 cells infected with oHSV, which was further impaired by oHSV-TRAIL (FIG. 3C). There was a complete shutdown of ERK 1/2 phosphorylation in both oHSV and oHSV-TRAIL infected GBM8F cells. JNK and p38 were activated in LN229 and GBM8F cells after oHSV and oHSV-TRAIL infection.

Figure 5A:
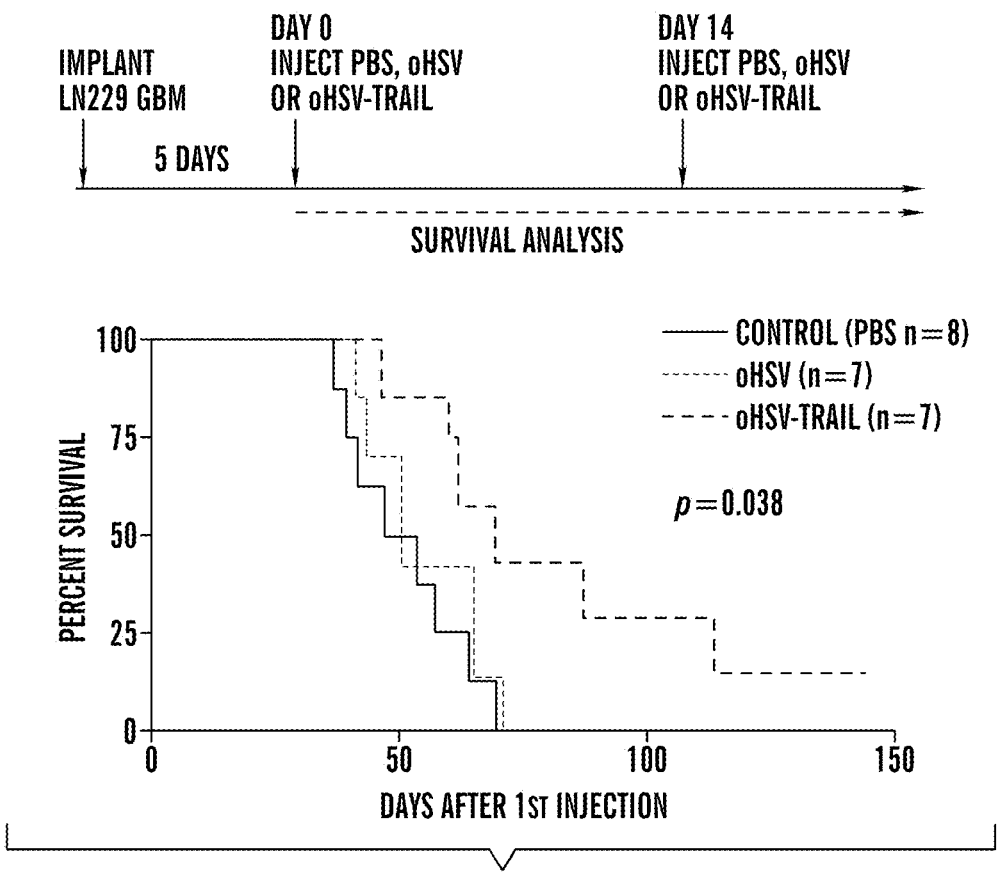
FIGS. 5A-5D contain graphs and photographs of experimental results that indicate Oncolytic herpes simplex virus (oHSV)-tumor necrosis factor-related apoptosis-inducing ligand (TRAIL) prolongs survival of mice-bearing both TRAIL and oHSV resistant glioblastoma multiforme (GBM).
Figure 5B:
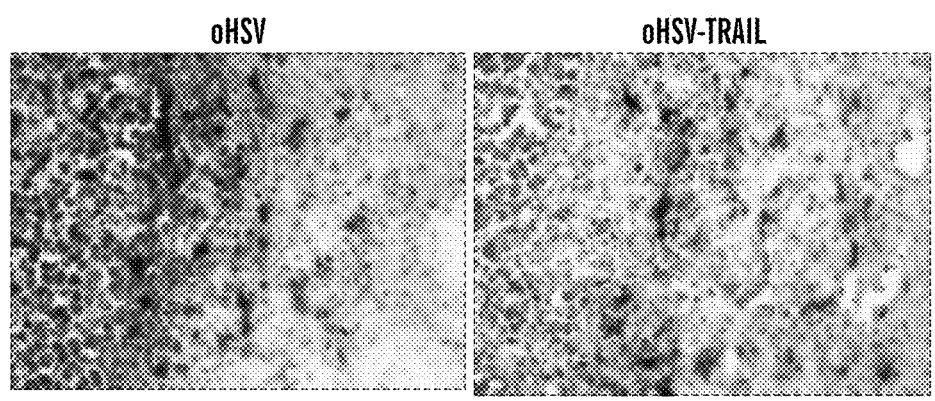
Figure 5C:
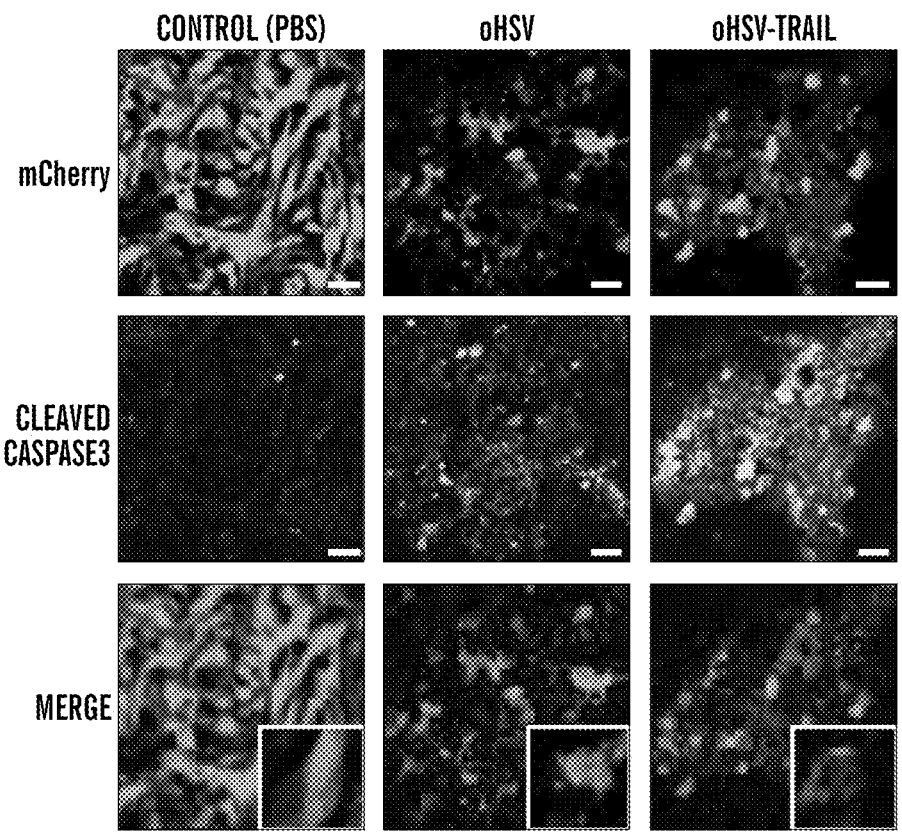
Figure 5D:
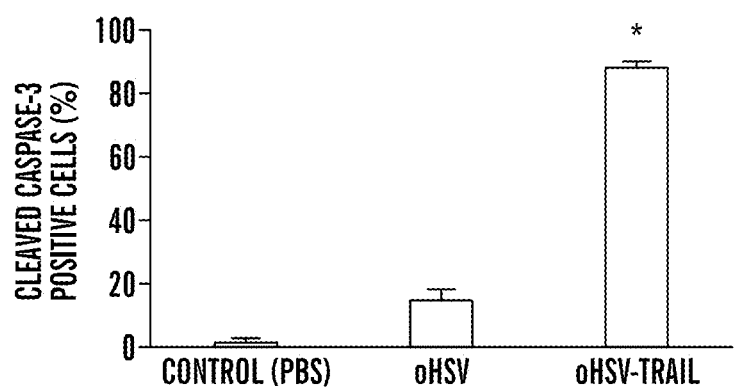
Figure 13:
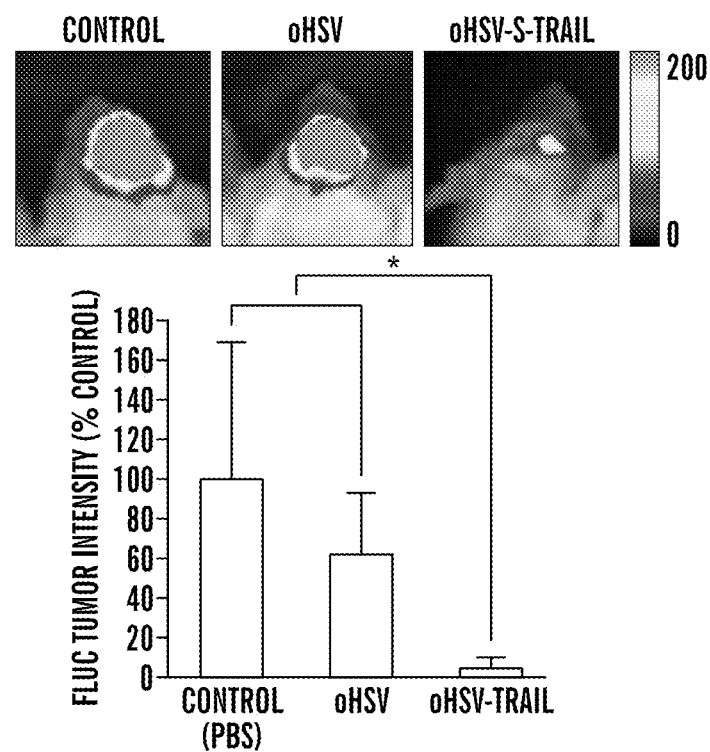
FIG. 13 contains graphs and photographs of experimental results that indicate oHSV-TRAIL inhibits growth of both TRAIL and oHSV resistant LN229-Fluc-mCherry GBMs in vivo: Mice bearing LN229-Fluc-mCherry GBMs treated with oHSV, oHSV-STRAIL or PBS (control) were followed for changes in tumor volumes by Fluc bioluminescence intensities. One representative image of mice and the average tumor volume of each group on 7 days after treatment are shown. The average tumor volumes were normalized to the control (PBS) group. n=5 in each group. * p<0.05 in the comparison of oHSV-TRAIL to control and to oHSV. Error bars indicate standard deviation.

We next sought to determine the significance of the JNK/ERK MAP kinase signaling alterations in oHSV-TRAIL-mediated cytotoxicity of both TRAIL and oHSV resistant GBM cells. To examine the role of JNK upregulation, we treated resistant GBM cells with JNK inhibitor, SP600125. LN229 were infected with oHSV or oHSV-TRAIL in the absence and presence of SP600125. Western blotting analysis showed SP600125 treatment resulted in the inhibition of JNK phosphorylation in oHSV and oHSV-TRAIL-infected cells and also a significant reduction in the cleavage of PARP in oHSV-TRAIL-infected cells (FIG. 4A). Caspase-3/7 activity assays showed a significant decrease in the caspase-3/7 activation in oHSV-TRAIL-infected cells in the presence of SP600125 as compared to the infected cells in the absence of SP600125 (FIG. 4B). We also investigated whether inhibition of ERK1/2 with MEK-ERK inhibitor, U0126, could mimic oHSV-mediated inhibition of ERK1/2 and sensitize TRAIL resistant GBM cells to TRAIL-induced apoptosis. Western blotting analysis showed that U0126 treatment of LN229 cells inhibited ERK phosphorylation and subsequent addition of purified S-TRAIL markedly increased PARP cleavage (FIG. 4C). Combined treatment with U0126 and S-TRAIL decreased cell viability in resistant LN229 GBM cells compared with single treatment (FIG. 4D). These results thus suggest that oHSV-mediated downregulation of the ERK-MAPK and upregulation of JNK signaling may contribute to apoptotic cell death in oHSV-TRAIL-infected resistant GBM cells.

oHSV-TRAIL Inhibits GBM Growth and Invasion In Vivo and Prolongs Survival of Mice Bearing Both TRAIL and oHSV Resistant GBM We assessed the therapeutic efficacy of oHSV-TRAIL in intracranial GBMs, using LN229 and GBM8F glioma lines which were engineered to express Fluc-mCherry (LN229-FmC, GBM8F-FmC). Mice bearing established intracranial LN229-FmC GBMs were administered intratumorally with oHSV, oHSV-TRAIL, or phosphate-buffered saline (PBS) and followed for changes in tumor volumes by Fluc imaging. As expected, oHSV injection had no impact on both tumor burden (FIG. 13A) and survival (FIG. 5A, PBS: 50.5 days, oHSV: 49 days) in this resistant GBM model. In contrast, oHSV-TRAIL injection resulted in significant decrease in tumor volumes compared to both control (PBS) and oHSV treated mice (FIG. 13A) and prolonged survival of mice-bearing intracranial GBMs (FIG. 5A). The median survival of oHSV-TRAIL-treated mice was 69 days, which was significantly longer than PBS- and oHSV-treated mice (FIG. 5A; P=0.038 oHSV and oHSV-TRAIL comparison, log-rank test). X-gal staining of the brain sections collected 48 hours post oHSV or oHSV-TRAIL injection showed an extensive distribution of reporter β-galactosidase positivity, which overlapped with the tumor area, suggesting that the spread of virus infection was comparable between oHSV and oHSV-TRAIL (FIG. 5B). Immunohistochemical analysis and confocal microscopy showed significantly increased cleaved caspase-3 staining in sections from oHSV-TRAIL-treated tumors as compared to oHSV and PBS treated tumors. Furthermore, no cleaved caspase-3 staining was seen in normal brain cells in all treated groups revealing the tumor specificity of oHSV-TRAIL treatment (FIG. 5C, D).

Figure 6A:
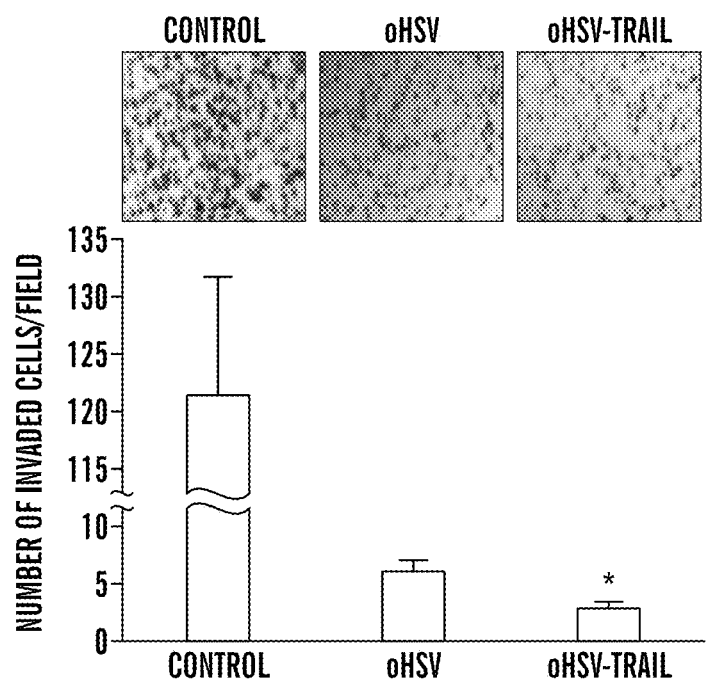
FIGS. 6A-6B contain graphs and photographs of experimental results that indicate Oncolytic herpes simplex virus (oHSV)-tumor necrosis factor-related apoptosis-inducing ligand (TRAIL) inhibits glioblastoma multiforme (GBM) invasion in vitro and in vivo in TRAIL resistant GBM.
Figure 6B:
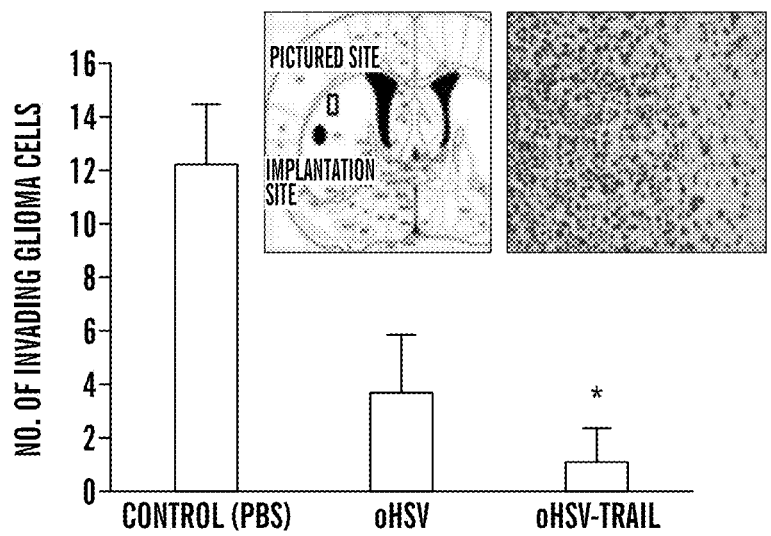
Figure 14:
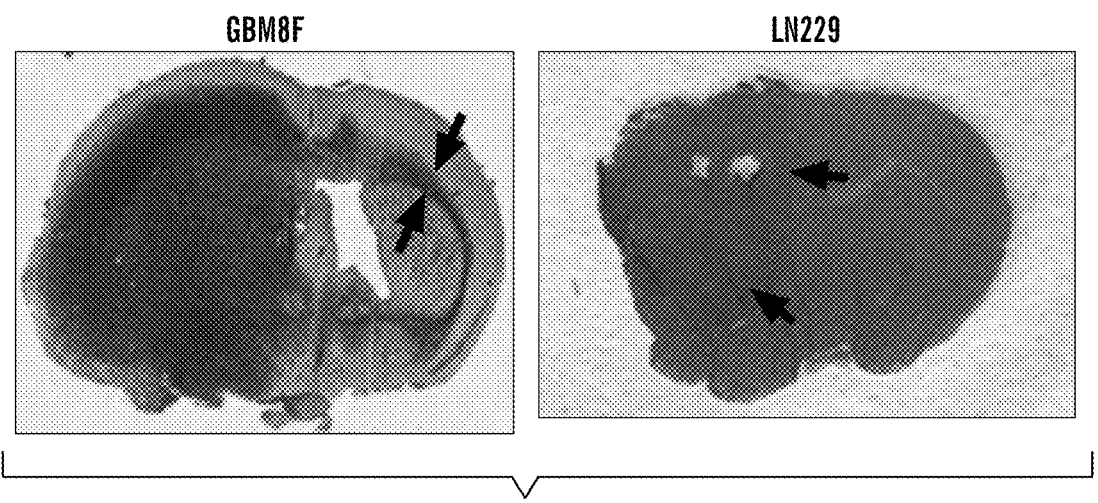
FIG. 14 contains photographs of experimental results that indicate H&E stained mouse brain sections harboring intracerebral tumors. Left panel, GBM8F with arrows showing contralateral tumor extension. Right panel, LN229. Arrows show discrete tumor brain borders.

To examine the effect on GBM cell invasion, we used matrigel-coated assays in vitro and intracranial mouse GBM model using invasive GBM8F as opposed to LN229 GBM line which is a noninvasive line (FIG. 14). oHSV and oHSV-TRAIL treatment reduced the number of GBM8F cells that had invaded in matrigel-coated invasion assay, with oHSV-TRAIL having a stronger inhibitory effect than oHSV (FIG. 6A). In vivo, both oHSV and oHSV-TRAIL injection into intracranial GBM8F tumors reduced the number of invading GBM8F cells as compared to the control, with oHSV-TRAIL having a stronger inhibitory effect than oHSV (FIG. 6B). These results demonstrate that oHSV-TRAIL induces apoptosis in TRAIL and oHSV resistant intracranial GBM, inhibits GBM growth and invasiveness and significantly increases survival in mice.

Discussion

In this study, we identified GBM lines that are either resistant to TRAIL mediated apoptosis or resistant to both oHSV-mediated oncolysis and TRAIL, and created a novel oHSV-bearing secretable-TRAIL (oHSV-TRAIL) to study the mechanism-based targeted therapy in resistant GBM lines in vitro and in vivo. We show that oHSV-TRAIL induces apoptosis in TRAIL and oHSV resistant GBMs by targeting both cell proliferation and death pathways. Furthermore, oHSV-TRAIL inhibits GBM growth and invasion and prolongs survival of mice-bearing intracranial brain tumors.

GBMs are molecularly heterogeneous tumors usually containing a subset of tumor cells that are resistant to a number of currently used anti-GBM therapies.[1] These cells rapidly take over and ultimately result in tumor progression. oHSV as a single agent has been tested in preclinical studies and shown to result in oncolysis in most GBM cells including GBM stem cells.[13,28,29] However, while phase I clinical trials using intracranial oHSV inoculation demonstrated safety in GBM patients, they showed only partial radiologic responses.[9,30,31] These results suggest that GBMs might be heterogeneous in the responses to oHSV and contain a subset of cells resistant to oHSV-mediated oncolysis. In this study, we screened a panel of eight GBM cell lines that covers established GBM cell lines and patient derived primary GSCs. We found that GBM cells have differential sensitivities to oHSV-mediated oncolysis as well as TRAIL-mediated apoptosis. To our knowledge, this is the first study which identifies GBM lines resistant to oHSV. Interestingly, our screening indicated that the yields of oHSV do not always parallel the efficiency of oHSV-mediated cell killing, implicating a presence of cell death mode other than oncolysis that affects oHSV efficacy.

A number of previous studies by others and our laboratory have shown that dual bioluminescence imaging of tumor cells and therapeutics enables rapid and noninvasive measurement of both tumor load and fate of therapeutics in vitro and in mice-bearing intracranial tumors.[10,12,32,33,34] Utilizing oHSV-Fluc, GBM cells expressing Rluc and dual bioluminescence imaging, our studies reveal that two distinct biological events, oHSV replication and its effects on cell viability can be monitored. Our results indicate that oHSV can replicate in a GBM line which is resistant to oHSV, even though the viral replication and spread is greatly decreased and slow when compared to the GBM lines which are sensitive to oHSV. The ability of oHSV to replicate in GBM lines resistant to oHSV provides a great rationale of using oHSV to deliver cytotoxic agents like TRAIL and studying both the molecular mechanism and therapeutic effect of oHSV and TRAIL treatments in GBMs that are resistant to oHSV-mediated oncolysis and TRAIL-mediated apoptosis.

Various strategies have been employed to overcome resistance of tumor cells to different drug regimens. The ability of TRAIL to selectively target tumor cells while remaining harmless to most normal cells makes it an attractive candidate for an apoptotic therapy for highly malignant brain tumors. However, a large percentage of primary GBM lines are resistant to TRAIL-induced apoptosis.[35] Our results reveal that oHSV infection and subsequent S-TRAIL treatment results in a caspase-3/7-mediated cell killing in a line that is resistant to both oHSV and TRAIL. Although TRAIL is a potent tumor-specific agent, its short biological half-life and limited delivery across the blood-brain barrier limit its applicability in treating brain tumors when delivered systemically. oHSV can replicate in situ, spread and exhibit oncolytic activity via a direct cytocidal effect, and at the same time can deliver substantial quantities of therapeutic molecules in situ. As compared to the other oncolytic viruses, the capacity to incorporate large transgenes into its genome is one of the advantages of HSV-1.[36] The intratumoral delivery of oHSV-TRAIL can overcome the limitations posed by systemic administration of TRAIL as it remedies the short half-life of drugs, the use of multiple drug regimens to target resistant GBMs, in addition to circumventing the restrictions posed by the blood-brain barrier to deliver drugs to brain.

Figure 7:
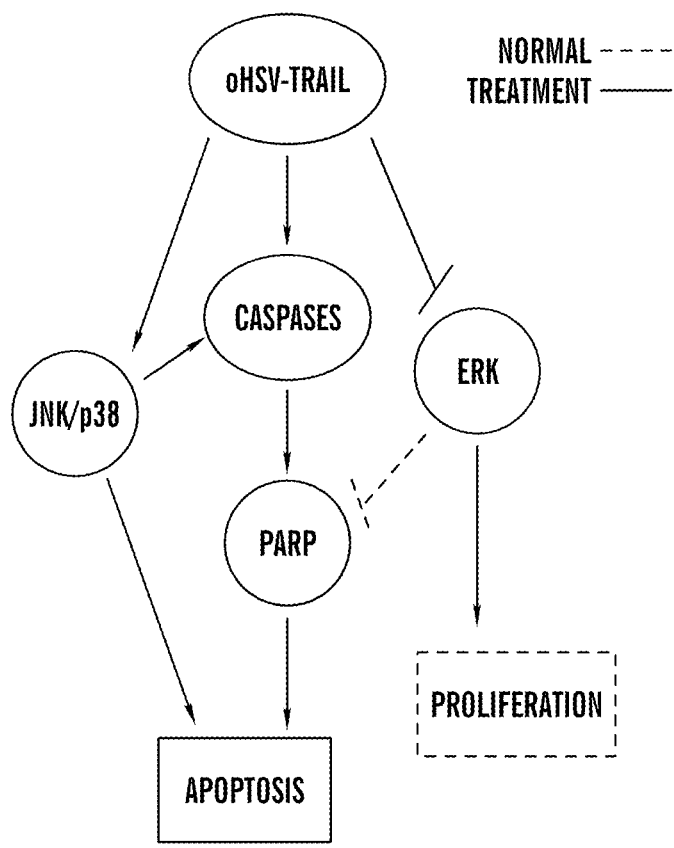
FIG. 7 is a Schematic presentation showing the mechanism underlying the efficacy of oncolytic herpes simplex virus (oHSV)-tumor necrosis factor-related apoptosis-inducing ligand (TRAIL) on resistant glioblastoma multiforme (GBM) cells.

HSV like other viruses have genes such as Us3 and Rs1 (ICP4) whose products have an anti-apoptotic function.[37,38] These genes appear to facilitate HSV replication by preventing premature cell death. Therefore, it is possible that combining proapoptotic molecule with oHSV dampens viral replication and reduces oHSV potency. Our data, however, showed that replication of oHSV and oHSV-TRAIL in glioma cells is comparable (FIG. 10A), indicating that expression of TRAIL does not suppress viral replication. We show that oHSV-TRAIL downregulates ERK phosphorylation, upregulates p38 and JNK phosphorylation and induces cleavage of caspases in two GBM cell lines either TRAIL or TRAIL and oHSV resistant. Downregulation of ERK phosphorylation and upregulation of P38 and JNK phosphorylation have been previously reported following infection with HSV-1.[39,40] ERK1/2, members of the MAPK super family, can mediate cell proliferation and apoptosis[41] while activation of ERK is primarily associated with promoting cellular proliferation. Activation of cell proliferation signals that block apoptosis is associated with tumorigenesis and resistance to chemotherapeutic drugs.[42] Activation of ERK is reported to prevent Fas-induced apoptosis in activated T cells[43] and inhibit activation of caspases despite the release of cytochrome c from mitochondria.[44,45,46] In contrast to ERK, the JNK and p38-MAPK signaling is activated by proinflammatory cytokines and a variety of cellular stresses, and is typically linked to differentiation and apoptosis. Xia et al. reported that activation of JNK and p38 and concurrent inhibition of ERK are critical for induction of apoptosis.[47] We show that: (i) the inhibition of JNK activation suppresses oHSV-TRAIL-mediated activation of caspase pathway, and (ii) a small-molecule inhibitor of MEK/ERK sensitizes resistant cells to TRAIL-mediated apoptosis. Therefore, our results suggest that oHSV-mediated downregulation of the ERK signaling and upregulation of the JNK and p38 signaling play a vital role in priming resistant cells so that S-TRAIL expressed in oHSV-TRAIL infected GBM cells promotes activation of caspase-3, -8, and -9, leading to apoptotic cell death (FIG. 7). Our studies thus underscore targeting both cell proliferation and death pathways as a crucial mechanism underlying oHSV-TRAIL-mediated robust induction of apoptosis in resistant GBMs.

Our in vivo studies reveal that oHSV-TRAIL results in marked attenuation of intracranial tumor growth and survival prolongation in mice-bearing TRAIL and oHSV resistant GBM. This makes a clear contrast to the lack of long-lasting antitumor efficacy mediated by an oncolytic adenovirus-expressing TRAIL.[48] Although established GBM lines are the most commonly used models in vitro and in vivo, they fail to recapitulate the clinical properties of tumors. Given this limitation of GBM lines as a representative GBM model, recent studies have focused on primary GBM lines and indicated a role for tumor-initiating cells in these lines. In an effort to test the effect of oHSV-TRAIL in such models, we used GBM8F primary GBM line that contains a subpopulation of CD133$^+$ cells[13] and exhibits highly invasive behavior in vivo. Our in vitro studies showed that despite resistance to TRAIL, oHSV-TRAIL is significantly more effective in killing and inhibiting invasiveness of GBM8F cells than oHSV. Furthermore, the number of invading cells in vivo was strongly reduced by a single inoculation of oHSV-TRAIL into GBM8F-generated tumors. This suggests that the oHSV spread in migrating tumor cells combined with in situ release of S-TRAIL can cooperate to block invasiveness of these cells. Future studies will need to address whether this is solely due to oHSV-TRAIL-mediated increased cell death or its additional but unknown functions that inhibit cellular migratory or invasive machineries.

In conclusion, our findings shed a new light on targeting oHSV and TRAIL resistant GBMs and pave the way for how oHSV and TRAIL can function in concert to target both cell proliferation and death pathways in heterogeneous GBM cells. A recent promising report on oncolytic virus targeting of metastatic cancer cells of multiple cancer types in humans highlighted the feasibility of achieving high concentrations of anticancer molecules in situ in the context of oncolytic virus therapy Therefore, this study may provide the key to ultimately develop novel oHSV-based therapies for patients with different tumors presenting different molecular profiles.

Materials and Methods

Parental and Engineered Cell Lines.

Established human GBM lines (Gli36, U87, U251, and LN229) and GBM8F were grown in Dulbecco's modified Eagle's medium supplemented with 10% fetal bovine serum and penicillin/streptomycin. GBM stem cells (GBM4, GBM6, and BT74) were cultured in Neurobasal medium (Invitrogen, Carlsbad, Calif.) supplemented with 3 mmol/l L-glutamine (Mediatech, Manassas, Va.), B27 (Invitrogen, Carlsbad, Calif.), 2 µg/ml heparin (Sigma-Aldrich, St Louis, Minn.), 20 ng/ml human EGF (R&D Systems, Minneapolis, Minn.), and 20 ng/ml human FGF-2 (Peprotech, Rocky Hills, N.J.) as described previously.[13] Two lentiviral vectors were used: (i) Pico2-Fluc-mCherry, a kind gift from Dr Andrew Kung (Dana Farber Cancer Institute; Boston, Mass.), (ii) Pico2-Rluc-mCherry, which is created by ligating Rluc fragment (the cDNA sequences encoding Rluc were amplified by PCR) into BamH1/BstB1-digested Pico2-Fluc-mcherry. Lentiviral packaging was performed by transfection of 293T cells as previously described.[33] LN229 and GBM8F were transduced with LV-Pico2-Fluc-mCherry and LV-Pico2-Rluc-mCherry at a MOI of 2 in medium-containing protamine sulfate (2 µg/ml) and LN229-Fluc-mCherry (LN229-FmC); GBM8-Fluc-mCherry (GBM8-FmC) LN229-Rluc-mCherry (LN229-RmC); GBM8-Rluc-mCherry (GBM8-FmC) lines were obtained after puromycin (1 ug/ml) selection in culture.

Recombinant oHSVs and Viral Growth Assay.

G47ΔBAC contains the genome of G47Δ (γ34.5−, ICP6−, ICP47−) and a cytomegalovirus promoter driven enhanced green fluorescent protein (EGFP) in place of lacZ in G47Δ.[17] Recombinant oHSV vectors, G47Δ-empty (oHSV; referred to oHSV in this study), G47Δ-TRAIL (oHSV-TRAIL), and G47Δ-Fluc (oHSV-Fluc), were generated using the methods described previously.[25,26,27,50] Briefly, the respective shuttle plasmids were integrated into G47ΔBAC using Cre-mediated recombination in DH10B *Escherichia coli*, and proper recombination confirmed by restriction analysis of BAC clones. Next, the resulting BAC and an Flpe-expressing plasmid were cotransfected to Vero cells, to remove the BAC-derived sequences and the EGFP gene, and allow virus to be produced. Each recombinant virus was plaque purified and expanded. All the recombinant oHSVs, oHSV, oHSV-TRAIL, and oHSV-Fluc, express *E. coli* lacZ driven by endogenous ICP6 promoter (FIG. 8A). oHSV bears no additional transgene sequences, and oHSV-TRAIL carries S-TRAIL driven by herpes simplex virus immediate early 4/5 promoter. Cytomegalovirus immediate early promoter was used to express Fluc-by oHSV-Fluc. For the viral growth assay, cells plated on 96-well plates were infected with oHSV at MOI=1. After virus adsorption, media was replaced and culture continued. Forty eight hours after infection, culture supernatant was harvested. Titers of infectious virus were determined by plaque assay on Vero cells (American Type Culture Collection, Manassas, Va.). The concentrations of TRAIL in conditioned media of GBM cells infected with oHSV-TRAIL at various MOIs were determined by ELISA using a TRAIL Immunoassay Kit (Biosource International, Camarillo, Calif.) using recombinant hTRAIL expressed in *E. coli* as a standard.

In Vitro Bioluminescence Assays.

To determine the effects of S-TRAIL, oHSV, and oHSV-TRAIL on GBM viability and caspase activation, GBM cells were seeded on 96-well plates ($0.5 \times 10^4$/well) and treated with different doses S-TRAIL (0-1,000 ng/ml) or different MOIs of oHSV or oHSV-TRAIL 24 hours after plating. Cell viability was measured by determining the aggregate cell metabolic activity using an ATP-dependent luminescent reagent (CellTiter-Glo; Promega, Madison, Wis.) and caspase activity was determined using a DEVD-aminoluciferin (Caspase-Glo-3/7, Promega) according to manufacturer's instructions. For dual-luciferase imaging of GBM cell viability and oHSV-Fluc distribution in the cells, Fluc and Rluc activity were measured in LN229-RmC and GBM8F-RmC cells by Dual-Glo luciferase assay system (Promega) according to manufacturer's instructions. All experiments were performed in triplicates.

Detection of Apoptosis by Flow Cytometry Using Annexin V Staining.

After a 24 hours treatment with oHSV, oHSV-TRAIL, or PBS (control), cells were stained with FITC-conjugated annexin V (Invitrogen) and propidium iodide (2 µg/ml) in accordance with the manufacturer's instructions. Cells were subjected to FACS analysis with a FACSCaliber (Becton Dickinson, Franklin Lakes, N.J.). Data acquisition and analysis were performed by CellQuest program (Becton Dickinson).

Western Blot Analysis.

Following treatment, GBM cells were lysed with NP40 buffer supplemented with protease (Roche, Indianapolis, Ind.) and phosphatase inhibitors (Sigma-Aldrich). Twenty micrograms of harvested proteins from each lysate were resolved on 10% SDS-PAGE, and immunoblotted with antibodies against caspase-8 (Cell Signaling), cleaved PARP (Cell Signaling, Danvers, Mass.), p-44/42MAPK (ERK 1/2) (Cell Signaling), phospho-p44/42MAPK (ERK 1/2) (Thr202,Thr204) (Cell Signaling), SAPK/JNK (Cell Signaling), phospho-SAPK/JNK (Thr183/Thr185) (Cell Signaling), p38-MAPK (Cell Signaling), phospho-p38 MAPK (Cell Signaling), caspase-9 (Stressgen, Pharmingdale, N.Y.), Bcl2 (Abcam, Cambridge, Mass.) or α-tubulin (Sigma-Aldrich); and blots were developed by chemiluminescence after incubation with horseradish peroxidase-conjugated secondary antibodies (Santa Cruz, Santa Cruz, Calif.). Blots were then exposed to film (3 seconds to 5 minutes) and quantification of western blot signals was performed using Image J. The data was normalized to α-tubulin expression. For inhibition studies, pan-caspase inhibitor, Z-VAD-FMK (Promega) JNK inhibitor SP600125 (Sigma-Aldrich), and the MEK inhibitor, U0126, (Promega Corporation) were used.

Intracranial GBM Cell Implantation and In Vivo Bioluminescence Imaging.

To follow viral distribution in intracranial GBMs, LN229-RmC, and GBM8F-RmC GBM ($5 \times 10^5$ cells per mouse; n=3 each GBM line) were stereotactically implanted into the brains (right striatum, 2.5-mm lateral from bregma and 2.5-mm deep) of SCID mice (6 weeks of age; Charles River Laboratories, Wilmington, Mass.). Five days later, mice-bearing intracranial GBMs were injected with oHSV-Fluc (6 µl of $2.0 \times 10^8$ plaque-forming unit/ml) intratumorally at the same coordinate as the tumor implantation, and viral distribution was followed by Fluc bioluminescence imaging over time as described previously.[33] To follow changes in tumor volume and mice survival after treatment, LN229-FmC GBM cells ($5 \times 10^5$ per mouse; n=31) were stereotactically implanted into the brains (right striatum, 2.5-mm lateral from bregma and 2.5-mm deep) of SCID mice (6 weeks of age). Mice were imaged for the presence of tumors by Fluc bioluminescence imaging and mice-bearing tumors were injected with 6 µl of $2.0 \times 10^8$ plaque-forming unit/ml of oHSV (n=10), oHSV-TRAIL (n=10), or PBS (n=11) intratumorally. Two days post-treatment, mice (n=3 in each group) were sacrificed for immunohistochemical analysis as described below. Fourteen days post-treatment, mice were again injected intratumorally with oHSV, oHSV-TRAIL, or PBS as described above. Mice were imaged for Fluc bioluminescence imaging and followed for survival and sacrificed when neurological symptoms became apparent. All in vivo procedures were approved by the Subcommittee on Research Animal Care at MGH.

Tissue Processing and Immunohistochemistry.

Mice were perfused by pumping ice-cold 4% paraformaldehyde directly into the heart and the brains were fixed in 4% paraformaldehyde and frozen sections were obtained for hematoxylin and eosin staining and immunohistochemistry. 5-Bromo-4-choloro-3-indolyl-β-D-galactopyranoside (X-gal) staining was performed to identify lacZ-expressing infected cells. For cleaved-caspase-3 staining, sections were incubated for 1 hour in a blocking solution (0.3% bovine serum albumin, 8% goat serum, and 0.3% TRITON X-100™ nonionic detergent) at room temperature, followed by incubation at 4° C. overnight with anti-cleaved-caspase-3 (Cell Signaling) diluted in blocking solution. Sections were incubated in Alexa Fluor 649 goat anti-rabbit secondary antibody (Invitrogen), and visualized using confocal microscope (LSM Pascal; Zeiss, Oberkochen, Germany). The percentage of cleaved caspase-3 positive cells was calculated by counting the positive cells in randomly selected field of views under a microscope.

In Vitro Invasion Assay.

The invasive capacity of GBM8F cells was tested using two chamber in vitro invasion assays (BD BioCoat Matrigel Invasion Chambers). GBM8F cells were seeded in the matrigel-coated upper chamber, infected with oHSV and oHSV-TRAIL at MOI=1 and 24 hours later the noninvading cells were removed from the upper surface of the invasion membrane and the cells on the lower surface were stained with Diff-Quick staining kit (IMEB Inc, San Marco, Calif.). The average number of cells/field was determined by counting the cells in 8 random fields/well in ×10 images of each well captured.

In Vivo Invasion Study.

GBM8F-FmC GBM cells ($3 \times 10^5$ per mouse; n=9) were stereotactically implanted into the brain (right striatum, 2.5-mm lateral from bregma and 2.5-mm deep) of SCID mice (6 weeks of age; Charles River Laboratories). Tumor-bearing mice were intratumorally injected with oHSV, oHSV-TRAIL, or PBS (n=3, each group) and 14 days post injection, mice were perfused and brains were removed and sectioned for hematoxylin and eosin staining and mCherry visualization. Brain sections on slides were visualized for mCherry expression and the number of GBM8F tumor invading toward adjacent normal brain tissue was counted and compared in different mice groups.

Statistical Analysis.

Data were analyzed by Student t-test when comparing two groups. Data were expressed as mean±SD and differences were considered significant at P<0.05. Kaplan-Meier analysis was used for mouse survival studies, and the groups were compared using the log-rank test.

REFERENCES

1. Wen, P Y, and Kesari, S (2008). Malignant gliomas in adults. *N Engl J Med* 359: 492-507.
2. Stupp, R, Mason, W P, van den Bent, M J, Weller, M, Fisher, B, Taphoorn, M J, et al. (2005). Radiotherapy plus concomitant and adjuvant temozolomide for glioblastoma. *N Engl J Med* 352: 987-996.
3. Stupp, R, Hegi, M E, Mason, W P, van den Bent, M J, Taphoorn, M J, Janzer, R C, et al. (2009). Effects of radiotherapy with concomitant and adjuvant temozolomide versus radiotherapy alone on survival in glioblastoma in a randomised phase III study: 5-year analysis of the EORTC-NCIC trial. *Lancet Oncol* 10: 459-466.
4. Aghi, M, and Martuza, R L (2005). Oncolytic viral therapies—the clinical experience. *Oncogene* 24: 7802-7816.
5. Corsten, M F, and Shah, K (2008). Therapeutic stem-cells for cancer treatment: hopes and hurdles in tactical warfare. *Lancet Oncol* 9: 376-384.
6. Johnstone, R W, Frew, A J, and Smyth, M J (2008). The TRAIL apoptotic pathway in cancer onset, progression and therapy. *Nat Rev Cancer* 8: 782-798.
7. Kock, N, Kasmieh, R, Weissleder, R, and Shah, K (2007). Tumor therapy mediated by lentiviral expression of shBcl-2 and S-TRAIL. *Neoplasia* 9: 435-442.
8. Liu, T C, Galanis, E, and Kirn, D (2007). Clinical trial results with oncolytic virotherapy: a century of promise, a decade of progress. *Nat Clin Pract Oncol* 4: 101-117.
9. Markert, J M, Medlock, M. D., Rabkin, S. D., Gillespie, G. Y., Todo, T., Hunter, W. D., Palmer, C. A., and Feigenbaum F, T C, Tufaro F, Martuza R L. (2000). Conditionally replicating herpes simplex virus mutant G207 for the treatment of malingnt glioma: results of a phoase I trial. *Gene Ther* 7: 867-874.
10. Sasportas, L S, Kasmieh, R, Wakimoto, H, Hingtgen, S, van de Water, J A, Mohapatra, G, et al. (2009). Assessment of therapeutic efficacy and fate of engineered human mesenchymal stem cells for cancer therapy. *Proc Natl Acad Sci USA* 106: 4822-4827.
11. Shah, K, Tung, C H, Breakefield, X O, and Weissleder, R (2005). In vivo imaging of S-TRAIL-mediated tumor regression and apoptosis. *Mol Ther* 11: 926-931.
12. Shah, K, Tung, C H, Yang, K, Weissleder, R, and Breakefield, X O (2004). Inducible release of TRAIL fusion proteins from a proapoptotic form for tumor therapy. *Cancer Res* 64: 3236-3242.
13. Wakimoto, H, Kesari, S, Farrell, C J, Curry, W T, Jr., Zaupa, C, Aghi, M, et al. (2009). Human glioblastoma-derived cancer stem cells: establishment of invasive glioma models and treatment with oncolytic herpes simplex virus vectors. *Cancer Res* 69: 3472-3481.
14. Parato, K A, Senger, D, Forsyth, P A, and Bell, J C (2005). Recent progress in the battle between oncolytic viruses and tumors. *Nat Rev Cancer* 5: 965-976.
15. Varghese, S, and Rabkin, S D (2002). Oncolytic herpes simplex virus vectors for cancer virotherapy. *Cancer Gene Ther* 9: 967-978.
16. Mineta, T, Rabkin, S D, Yazaki, T, Hunter, W D, and Martuza, R L (1995). Attenuated multi-mutated herpes simplex virus-1 for the treatment of malignant gliomas. *Nat Med* 1: 938-943.
17. Todo, T, Martuza, R L, Rabkin, S D, and Johnson, P A (2001). Oncolytic herpes simplex virus vector with enhanced MHC class I presentation and tumor cell killing. *Proc Natl Acad Sci USA* 98: 6396-6401.
18. Markert, J M, Liechty, P G, Wang, W, Gaston, S, Braz, E, Karrasch, M, et al. (2009). Phase 1b trial of mutant herpes simplex virus G207 inoculated pre- and post-tumor resection for recurrent GBM. *Mol Ther* 17: 199-207.
19. Hoffmann, D, and Wildner, O (2007). Comparison of herpes simplex virus- and conditionally replicative adenovirus-based vectors for glioblastoma treatment. *Cancer Gene Ther* 14: 627-639.
20. LeBlanc, HNaA, A. (2003). Apo2L/TRAIL and its death and decoy receptors. *Cell Death Diff* 10: 66-75.
21. Wiezorek, J, Holland, P, and Graves, J (2010). Death receptor agonists as a targeted therapy for cancer. *Clin Cancer Res* 16: 1701-1708.
22. Rozanov, D V, Savinov, A Y, Golubkov, V S, Rozanova, O L, Postnova, T I, Sergienko, E A, et al. (2009). Engineering a leucine zipper-TRAIL homotrimer with improved cytotoxicity in tumor cells. *Mol Cancer Ther* 8: 1515-1525.
23. Yip, S, and Shah, K (2008). Stem-cell based therapies for brain tumors. *Curr Opin Mol Ther* 10: 334-342.
24. Bagci-Onder, T, Wakimoto, H, Anderegg, M, Cameron, C, and Shah, K (2011). A dual PI3K/mTOR inhibitor, PI-103, cooperates with stem cell-delivered TRAIL in experimental glioma models. *Cancer Res* 71: 154-163.

25. Fukuhara, H, Ino, Y, Kuroda, T, Martuza, R L, and Todo, T (2005). Triple gene-deleted oncolytic herpes simplex virus vector double-armed with interleukin 18 and soluble B7-1 constructed by bacterial artificial chromosome-mediated system. *Cancer Res* 65: 10663-10668.

26. Kuroda, T, Martuza, R L, Todo, T, and Rabkin, S D (2006). Flip-Flop HSV-BAC: bacterial artificial chromosome based system for rapid generation of recombinant herpes simplex virus vectors using two independent site-specific recombinases. *BMC Biotechnol* 6: 40.

27. Yamamoto, S, Deckter, L A, Kasai, K, Chiocca, E A, and Saeki, Y (2006). Imaging immediate-early and strict-late promoter activity during oncolytic herpes simplex virus type 1 infection and replication in tumors. *Gene Ther* 13: 1731-1736.

28. Han, Z Q, Assenberg, M, Liu, B L, Wang, Y B, Simpson, G, Thomas, S, et al. (2007). Development of a second-generation oncolytic Herpes simplex virus expressing TNF alpha for cancer therapy. *J Gene Med* 9: 99-106.

29. Kurozumi, K, Hardcastle, J, Thakur, R, Yang, M, Christoforidis, G, Fulci, G, et al. (2007). Effect of tumor microenvironment modulation on the efficacy of oncolytic virus therapy. *J Natl Cancer Inst* 99: 1768-1781.

30. Kim, D, Martuza, R L, and Zwiebel, J (2001). Replication-selective virotherapy for cancer: Biological principles, risk management and future directions. *Nat Med* 7: 781-787.

31. Markert, E, Siebolts, U, Odenthal, M, Kreuzer, K A, and Wickenhauser, C (2009). High diagnostic value of morphologic examination and molecular analysis of bone marrow biopsies in a case of BCR-ABL+ CML with clusters of blasts. *Int J Hematol* 89: 294-297.

32. Corsten, M F, Miranda, R, Kasmieh, R, Krichevsky, A M, Weissleder, R, and Shah, K (2007). MicroRNA-21 knockdown disrupts glioma growth in vivo and displays synergistic cytotoxicity with neural precursor cell delivered S-TRAIL in human gliomas. *Cancer Res* 67: 8994-9000.

33. Shah, K, Hingtgen, S, Kasmieh, R, Figueiredo, J L, Garcia-Garcia, E, Martinez-Serrano, A, et al. (2008). Bimodal viral vectors and in vivo imaging reveal the fate of human neural stem cells in experimental glioma model. *J Neurosci* 28: 4406-4413.

34. Shah, K, Tang, Y, Breakefield, X, and Weissleder, R (2003). Real-time imaging of TRAIL-induced apoptosis of glioma tumors in vivo. *Oncogene* 22: 6865-6872.

35. Rieger, J, Frank, B, Weller, M, and Wick, W (2007). Mechanisms of resistance of human glioma cells to Apo2 ligand/TNF-related apoptosis-inducing ligand. *Cell Physiol Biochem* 20: 23-34.

36. Todo, T (2008). "Armed" oncolytic herpes simplex viruses for brain tumor therapy. *Cell Adh Mi* 2: 208-213.

37. Leopardi, R, Van Sant, C, and Roizman, B (1997). The herpes simplex virus 1 protein kinase US3 is required for protection from apoptosis induced by the virus. *Proc Natl Acad Sci USA* 94: 7891-7896.

38. Leopardi, R, and Roizman, B (1996). The herpes simplex virus major regulatory protein ICP4 blocks apoptosis induced by the virus or by hyperthermia. *Proc Natl Acad Sci USA* 93: 9583-9587.

39. Perkins, D, Gyure, K A, Pereira, E F, and Aurelian, L (2003). Herpes simplex virus type 1-induced encephalitis has an apoptotic component associated with activation of c-Jun N-terminal kinase. *Neurovirol* 9: 101-111.

40. Walsh, D, and Mohr, I (2004). Phosphorylation of eIF4E by Mnk-1 enhances HSV-1 translation and replication in quiescent cells. *Genes Dev* 18: 660-672.

41. Mebratu, Y, and Tesfaigzi, Y (2009). How ERK1/2 activation controls cell proliferation and cell death: Is subcellular localization the answer? *Cell Cycle* 8: 1168-1175.

42. Allan, L A, Morrice, N, Brady, S, Magee, G, Pathak, S, and Clarke, P R (2003). Inhibition of caspase-9 through phosphorylation at Thr 125 by ERK MAPK. *Nat Cell Biol* 5: 647-654.

43. Holmstrom, T H, Schmitz, I, Soderstrom, T S, Poukkula, M, Johnson, V L, Chow, S C, et al. (2000). MAPK/ERK signaling in activated T cells inhibits CD95/Fas-mediated apoptosis downstream of DISC assembly. *EMBO J* 19: 5418-5428.

44. Erhardt, P, Schremser, E J, and Cooper, G M (1999). B-Raf inhibits programmed cell death downstream of cytochrome c release from mitochondria by activating the MEK/Erk pathway. *Mol Cell Biol* 19: 5308-5315.

45. Jacobson, M D, Weil, M, and Raff, M C (1997). Programmed cell death in animal development. *Cell* 88: 347-354.

46. Tashker, J S, Olson, M, and Kornbluth, S (2002). Post-cytochrome C protection from apoptosis conferred by a MAPK pathway in Xenopus egg extracts. *Mol Biol Cell* 13: 393-401.

47. Xia, Z, Dickens, M, Raingeaud, J, Davis, R J, and Greenberg, M E (1995). Opposing effects of ERK and JNK-p38 MAP kinases on apoptosis. *Science* 270: 1326-1331.

48. Wohlfahrt, M E, Beard, B C, Lieber, A, and Kiem, H P (2007). A capsid-modified, conditionally replicating oncolytic adenovirus vector expressing TRAIL Leads to enhanced cancer cell killing in human glioblastoma models. *Cancer Res* 67: 8783-8790.

49. Breitbach, C J, Burke, J, Jonker, D, Stephenson, J, Haas, A R, Chow, L Q, et al. (2011). Intravenous delivery of a multi-mechanistic cancer-targeted oncolytic poxvirus in humans. *Nature* 477: 99-102.

50. Saeki, Y, Ichikawa, T, Saeki, A, Chiocca, E A, Tobler, K, Ackermann, M, et al. (1998). Herpes simplex virus type 1 DNA amplified as bacterial artificial chromosome in *Escherichia coli*: rescue of replication-competent virus progeny and packaging of amplicon vectors. *Hum Gene Ther* 9: 2787-2794.

What is claimed:

1. A method of inhibiting glioblastoma tumor progression in a subject comprising contacting a glioblastoma tumor with an effective amount of a pharmaceutical composition comprising a recombinant oncolytic herpes simplex virus comprising a nucleic acid sequence encoding, in expressible form, a secretable polypeptide comprising the extracellular domain of tumor necrosis factor-related apoptosis-inducing ligand (s-TRAIL), wherein the recombinant oncolytic herpes simplex virus induces apoptosis in tumor cells that are resistant to apoptosis induction by TRAIL and by oncolytic herpes simplex virus.

2. The method of claim 1, wherein the oHSV is selected from the group consisting of G207, G47Δ HSV-R3616, 1716, R3616, and R4009.

3. The method of claim 1, wherein the TRAIL is regulated by the HSV immediate early 4/5 promoter.

4. The method of claim 1, wherein the virus contains an additional exogenous nucleic acid in expressible form.

5. The method of claim 1, wherein the virus contains no additional exogenous nucleic acids.

6. The method of claim 1, wherein contacting is by a method of administration to the subject is by a method selected from the group consisting of intravenous administration, intraperitoneal administration, intramuscular administration, intracoronary administration, intraarterial administration, subcutaneous administration, transdermal delivery, intratracheal administration, subcutaneous administration, intraarticular administration, intraventricular administration, inhalation, intracerebral, nasal, oral, pulmonary administration, impregnation of a catheter, and direct injection into a tissue or tumor.

7. A method of treating glioblastoma in a subject comprising administering to the subject a therapeutically effective amount of a pharmaceutical composition comprising a recombinant oncolytic herpes simplex virus comprising a nucleic acid sequence-encoding, in expressible form, a secretable polypeptide comprising the extracellular domain of tumor necrosis factor-related apoptosis-inducing ligand (s-TRAIL), wherein the recombinant oncolytic herpes simplex virus induces apoptosis in glioblastoma tumor cells that are resistant to apoptosis induction by TRAIL and by oncolytic herpes simplex virus, to thereby treat the cancer.

8. The method of claim 7, wherein administration is by a method selected from the group consisting of intravenous administration, intraperitoneal administration, intramuscular administration, intracoronary administration, intraarterial administration, subcutaneous administration, transdermal delivery, intratracheal administration, subcutaneous administration, intraarticular administration, intraventricular administration, inhalation, intracerebral, nasal, oral, pulmonary administration, impregnation of a catheter, and direct injection into a tissue or tumor.

9. The method of claim 7, wherein the oncolytic virus is an oncolytic herpes simplex virus (oHSV) selected from the group consisting of G207, G47Δ HSV-R3616, 1716, R3616, and R4009.

* * * * *

SEQUENCE LISTING

<160> NUMBER OF SEQ ID NOS: 4

<210> SEQ ID NO 1
<211> LENGTH: 281
<212> TYPE: PRT
<213> ORGANISM: Homo sapiens

<400> SEQUENCE: 1

```
Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
            35                  40                  45

Tyr Ser Lys Ser Gly Ile Ala Cys Phe Leu Lys Glu Asp Ser Tyr
    50                  55                  60

Trp Asp Pro Asn Asp Glu Ser Met Asn Ser Pro Cys Trp Gln Val
65                  70                  75                  80

Lys Trp Gln Leu Arg Gln Leu Val Arg Lys Met Ile Leu Arg Thr Ser
            85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
            115                 120                 125

Thr Arg Gly Arg Ser Asn Thr Leu Ser Ser Pro Asn Ser Lys Asn Glu
130                 135                 140

Lys Ala Leu Gly Arg Lys Ile Asn Ser Trp Glu Ser Arg Ser Gly
145                 150                 155                 160

His Ser Phe Leu Ser Asn Leu His Leu Arg Asn Gly Glu Leu Val Ile
            165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
            195                 200                 205

Tyr Ile Tyr Lys Tyr Thr Ser Tyr Pro Asp Pro Ile Leu Leu Met Lys
210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
    275                 280
```

<210> SEQ ID NO 2
<211> LENGTH: 232
<212> TYPE: PRT
<213> ORGANISM: Mus musculus

<400> SEQUENCE: 2

```
Met Thr Val Leu Ala Pro Ala Trp Ser Pro Asn Ser Ser Leu Leu Leu
1               5                   10                  15

Leu Leu Leu Leu Leu Ser Pro Cys Leu Arg Gly Thr Pro Asp Cys Tyr
            20                  25                  30

Phe Ser His Ser Pro Ile Ser Ser Asn Phe Lys Val Lys Phe Arg Glu
            35                  40                  45

Leu Thr Asp His Leu Leu Lys Asp Tyr Pro Val Thr Val Ala Val Asn
            50                  55                  60

Leu Gln Asp Glu Lys His Cys Lys Ala Leu Trp Ser Leu Phe Leu Ala
65                  70                  75                  80

Gln Arg Trp Ile Glu Gln Leu Lys Thr Val Ala Gly Ser Lys Met Gln
```

```
                         85                  90                  95
Thr Leu Glu Asp Val Asn Thr Glu Ile His Phe Val Thr Ser Cys
            100                 105                 110

Thr Phe Gln Pro Leu Pro Glu Cys Leu Arg Phe Val Gln Thr Asn Ile
            115                 120                 125

Ser His Leu Leu Lys Asp Thr Cys Thr Gln Leu Leu Ala Leu Lys Pro
    130                 135                 140

Cys Ile Gly Lys Ala Cys Gln Asn Phe Ser Arg Cys Leu Glu Val Gln
145                 150                 155                 160

Cys Gln Pro Asp Ser Ser Thr Leu Leu Pro Pro Arg Ser Pro Ile Ala
                165                 170                 175

Leu Glu Ala Thr Glu Leu Pro Glu Pro Arg Pro Arg Gln Leu Leu Leu
                180                 185                 190

Leu Leu Leu Leu Leu Leu Pro Leu Thr Leu Val Leu Leu Ala Ala Ala
                195                 200                 205

Trp Gly Leu Arg Trp Gln Arg Ala Arg Arg Arg Gly Glu Leu His Pro
                210                 215                 220

Gly Val Pro Leu Pro Ser His Pro
225                 230

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Ala Ser Gly Gly Pro Glu
1               5

<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Ser Thr Gly Gly Ser Gly Lys Pro Gly Ser Gly Glu Gly Ser Thr
1               5                   10                  15

Gly Gly
```